United States Patent [19]

Roizen et al.

[11] Patent Number: 5,025,374
[45] Date of Patent: Jun. 18, 1991

[54] PORTABLE SYSTEM FOR CHOOSING PRE-OPERATIVE PATIENT TEST

[75] Inventors: Michael Roizen, Chicago; William E. Turcotte, II, Oak Park; Richard E. Pfisterer, Arlington Heights, all of Ill.

[73] Assignee: ARCH Development Corp., Chicago, Ill.

[21] Appl. No.: 130,934

[22] Filed: Dec. 9, 1987

[51] Int. Cl.$^5$ ............................................. G06F 15/42
[52] U.S. Cl. .......................... 364/413.02; 364/413.01
[58] Field of Search ................. 364/415, 401, 413.02, 364/413.01, 401

[56] References Cited

U.S. PATENT DOCUMENTS

| | | | |
|---|---|---|---|
| 3,566,370 | 2/1971 | Worthington | 364/900 |
| 3,934,226 | 1/1976 | Stone | 364/200 |
| 3,942,157 | 3/1976 | Azure | 364/900 |
| 4,092,524 | 5/1978 | Moreno | 235/419 |
| 4,130,881 | 12/1978 | Haessler | 364/900 |
| 4,290,114 | 9/1981 | Sinay | 364/415 |
| 4,365,315 | 12/1982 | Jamnik | 364/419 |
| 4,396,985 | 8/1983 | Ohara | 364/405 |
| 4,569,421 | 2/1986 | Sandstedt | 364/401 |
| 4,615,002 | 9/1986 | Innes | 364/200 |
| 4,731,725 | 3/1988 | Suto | 364/415 |

FOREIGN PATENT DOCUMENTS 2393356 2/1979 France .............................. 364/415

OTHER PUBLICATIONS

"Computer-Aided Diagnosis of Dermatologic Disorders"; *Computer in Dermatology*, William v. Stuecker.

Primary Examiner—Jerry Smith
Assistant Examiner—Gail O. Hayes
Attorney, Agent, or Firm—Laff, Whitesel, Conte & Saret

[57] ABSTRACT

An interactive medical test selector for use by a patient is about the size of a book and has a screen for displaying questions to a patient, a limited number of keys by which the patient can enter answers, and a memory device for storing the patient's answers. The test selector is battery-powered for portability and uses a low-power liquid crystal display or the like to display instructions and medical questions to the patient. Only four keys are seen or used by the patient for answering the questions: YES, NO, NOT SURE, and NEXT QUESTION. Additional control keys used by the medical staff are hidden from the patient. The device is controlled by a pre-programmed microcomputer on a chip, and a ROM-based, removable and replaceable control program which not only collects, but also analyzes the patient's answers and makes appropriate recommendations based on those answers, and drives a remote printer or computer terminal.

8 Claims, 20 Drawing Sheets

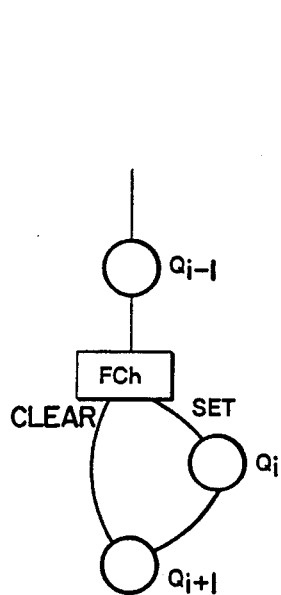
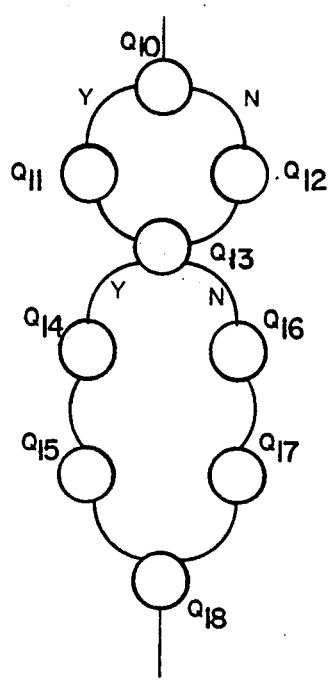
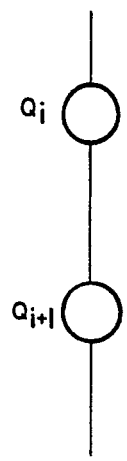
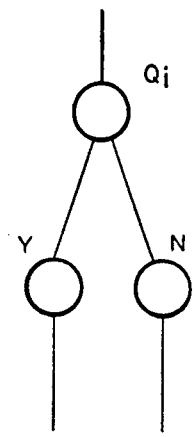
FIG. 13A  FIG. 13B  FIG. 13C  FIG. 13D
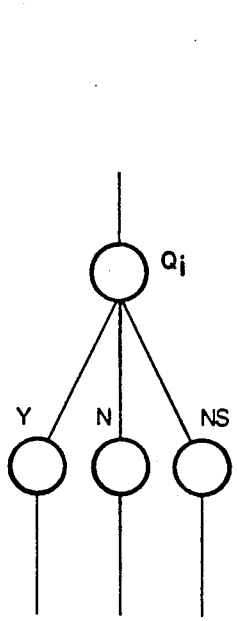
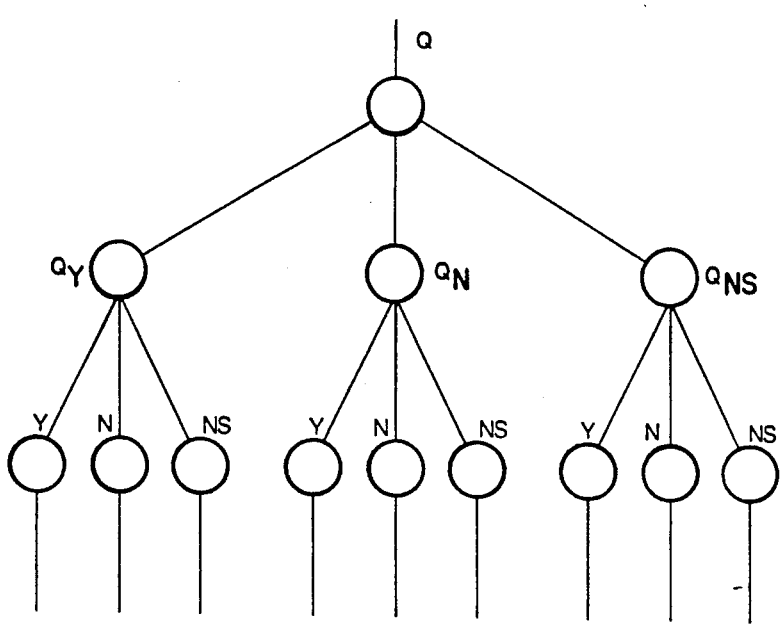
FIG. 13E  FIG. 13F

PORTABLE SYSTEM FOR CHOOSING PRE-OPERATIVE PATIENT TEST

NOTICE REGARDING COPYRIGHTS

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

This invention relates to a medical test selecting device, and more particularly to a portable computerized device which administers a questionnaire to a patient, especially a surgical patient, even if the patient is bedridden, and is capable of printing out a full report including advice to a physician as to what pre-operative or other medical tests are indicated for that patient.

BACKGROUND OF THE INVENTION

It has been estimated that of the approximately $30 billion spent each year in the United States for medical tests, as much as 60% of that amount ($18 billion) is wasted on unnecessary tests; i.e., those which, for a given patient, would not be needed if the physician had the benefit of a reliable medical history. See, for example, *Are We Hooked on Tests*, U.S. News & World Report, Nov. 23, 1987, pp. 60-65, 68-70, 72.

This problem of unnecessary testing is particularly acute in cases where a patient is about to undergo surgery and, in order to determine the proper anesthesia, the patient's general medical history is taken.

This medical history strongly influences which diagnostic tests the medical staff chooses to perform before surgery. For example, if the patient discloses that he or she has any pain or discomfort upon urination, or has noticed any blood in the urine, then a urinalysis (a chemical analysis of the urine) ought to be performed. But if those symptoms are not present, it is considered medically unnecessary to administer a urinalysis, absent some other medical indication for the test.

Under current medical practice, it requires about seventy-five or more questions to determine which, if any, of the various available pre-operative tests (urinalysis, chest x-rays, EKG, etc.) might have to be performed before determining what anesthesia ought to be used during surgery. If the physician is not sure that all these questions were properly asked, or has doubts about the care with which the patient's answers have been recorded, he or she is likely to include in the battery of pre-operative tests many that could have been excluded based on an accurate patient history.

To save the time of physicians, questionnaires have been devised that can be administered by a nurse or other trained medical worker, or even directly filled in by the patient. But the time of a trained medical worker is also too valuable to spend on such tasks, since that makes the individual unavailable to perform other, more pressing, medical tasks which require such training.

If the patient completes the questionnaire alone, he or she may overlook or ignore some of the questions. Also, if the patient usually reads in a foreign language or has vision problems, he or she may have trouble completing the questionnaire alone.

Even if a questionnaire is fully and properly filled out, tallying of the patient's answers to determine which tests are needed is a time-consuming and tedious task, in the course of which medical workers sometimes inadvertently introduce errors.

Because of these problems, all too often a reliable medical history of this type is not taken prior to surgery, in which case the patient may have to undergo a comprehensive battery of pre-operative tests, many of them unneeded. These unnecessary tests are expensive for the patient and a burden on an already overworked medical system. In addition, the more tests are done the greater is the risk of false positives and iatrogenic harm from pursuit of false positives. Therefore, there is a great need to "automate" the reliable taking and tabulating of pre-operative test questionnaires.

THE PRIOR ART

The prior art has proposed the use of computers or computer terminals to automate the taking of general-purpose medical histories. For example, in U.S. Pat. No. 3,566,370 of Worthington et al. a computer terminal which is connected by telephone lines to a mainframe computer displays questions on a CRT screen which are to be answered by the patient sitting at a full alphanumeric keyboard. After the patient answers the questions, the computer stores, formats and prints out the patient's medical history. The Worthington patent also suggests that the questions presented to the patient for the purpose of taking his medical history can be in foreign languages when necessary. U.S. Pat. No. 4,130,881 of Haessler et al. is similar to Worthington in many respects.

Published Japanese Patent Application No. 59-231676 is similar to the above-mentioned U.S. patents in its use of a computer console and full alphanumeric keyboard, except that in addition the computer there is programmed to develop recommendations. The recommendations are intended for the guidance of Japanese pharmacists, not medically trained physicians, in prescribing oral medications according to Chinese traditional folk medicine criteria. To date no computerized system has been developed which is specifically programmed to administer the particular sequence of questions which is considered appropriate for pre-operative test selection according to accepted western scientific medical criteria.

General-purpose computing machines of the type employed in the above prior art patents are much too expensive, bulky, and complicated for the task of automating the pre-operative test selection process. Moreover, the great majority of patients are not "computer literate" and find such equipment difficult to use even when they are feeling well. A patient who is about to go into surgery in the very near future is particularly likely to find a large-scale general-purpose computer system confusing and threatening. The problem is exacerbated by the fact that these computers require the patient to compose an answer on a keyboard containing the full range of alphanumeric characters and other keys.

The prior art has recognized the need in certain contexts for a simplified special-purpose data-processing device which offers the non-computer-literate person a simple choice between "yes" and "no" answers, as in published French Patent Application No. 77 17048. But the computer in that application is programmed to recommend a skin cosmetic regime rather than a medical treatment procedure.

A pre-operative patient is sometimes in such poor condition that it would be physically difficult to get out of bed and sit at the keyboard of large-scale computer system. Ideally, therefore, an automated pre-operative test recommendation device would be small enough to be portable. Here again, the prior art does have examples of portable special-purpose computers, but these too have not been adapted for use in a pre-operative test selection environment. The portable computer in U.S. Pat. No. 4,686,624 of Blum et al., for example, is dedicated to controlling the dietary habits of diabetics.

BRIEF SUMMARY OF THE INVENTION

Accordingly, one general object of the invention is to provide a automatic device for taking patient histories which is especially adapted for the selection of medical and/or pre-operative tests, and can be easily used even by bed-ridden patients. A more particular object is to provide a small, battery-powered, portable dedicated computer that automatically displays questions and enables a non-computer-literate patient to answer by means of only a few keys. A further object is to provide such a device that automatically analyzes the patient's answers to determine which tests appear to be necessary, and provides a printed report. Yet another object is to provide a device which is medically reliable, but is nevertheless relatively inexpensive. It is also desirable to provide a device of this type which can be easily be field-modified to update the questions at intervals to keep up with the progress of medical knowledge. Such a device should also be capable of communicating with either the patient or the doctor in a foreign language when necessary.

The invention provides a hand-held, battery-powered medical and/or pre-operative test selector for use by a patient which has means for displaying questions to a patient, a limited number of keys by which the patient can enter answers, and a memory device for storing the patient's answers. Alternatively, an audio jack enables the patient to listen to the questions with earphones. The device preferably uses a low-power display such as a liquid crystal or the like. In a preferred embodiment, no more than four keys are used by the patient: YES, NO, NOT SURE, and GO TO NEXT QUESTION (hereafter "NEXT QUESTION"). Additional control keys may be provided for use by the medical staff, but are hidden from the patient. The device is controlled by a pre-programmed microcomputer on a chip which stores in a memory the text of user instructions, medical or pre-operative questions, and words to be used in printed reports. The microcomputer is programmed to tally the patient's answers and, on the basis of that information, to indicate which tests are advisable. The test selector can be provided with additional prestored text so the user has the option of displaying questions in more than one language, or being asked the questions in an audio mode. The questions and the software for recommending pre-operative tests are stored in a readily removable and replaceable integrated circuit chip to facilitate updating of the questions and/or the test selection procedure at intervals, as medical knowledge advances.

BRIEF DESCRIPTION OF THE DRAWINGS

These mentioned and other features of the invention will become more apparent, and the operation of the invention will be best understood, by reference to the following detailed description of preferred embodiments of the invention, when taken in conjunction with the accompanying drawings, in which:

FIGS. 13A-13F show nodes representing questions to be asked and various arrangements of program paths linking the questions.

DETAILED DESCRIPTION OF THE PREFERRED EMBODIMENT

1. General Appearance and Functions

Figure 1:
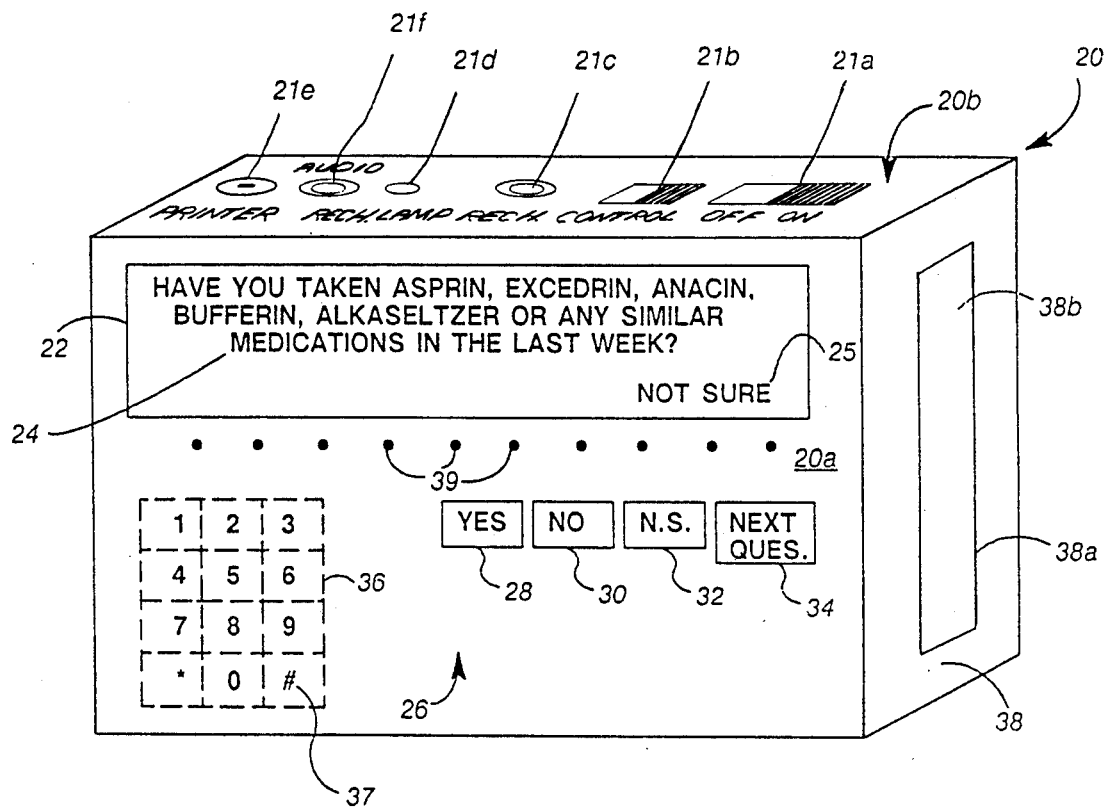
FIG. 1 is perspective view of an exemplary pre-operative test selector according to the invention.

A portable interactive test selector 20 embodying the invention is shown in FIG. 1, in the Question & Answer (Q&A) mode used by a patient. Preferably it is battery-powered and about the size of a book or calculator so that a patient can operate it on his or her lap, or at a desk or table. Built in to an operating panel 20a are a text display 22 and a patient keypad 26.

The operating panel also has a control keypad 36 which is kept inconspicuous or hidden from the patient. For example, the control keypad may be concealed by a translucent plastic sheet, but have labeled keys that can be illuminated to make the key labels visible from behind the translucent sheet. Or the control keypad can be hidden from the patient behind a sliding panel or the like.

Yet another alternative for the control keypad 36 is to provide a row of small, unlabeled, switch buttons 39 just below text display 22. When these switches 39, which can be membrane switches or nonmoving capacitance-sensitive switches, are activated by a medical staffer, numerical labels for them (not shown) can be made to appear in the bottom row of display 22.

Test selector 20 also has a back panel 20b, on which are arrayed an ON/OFF switch 21a, a control button 21b, a socket 21c for a battery recharger, a recharging lamp 21d, a printer jack 21e, and an audio output jack.

A side panel 38 of the test selector has a recess 38a for receiving a read-only memory (ROM) cartridge 38b for updating a control program and test information.

A series of prestored YES/NO questions 24 for the patient appear one at a time on text display 22, to each of which the patient responds in turn by pressing an appropriate answer key on the patient keypad 26. Alternatively, the coded sounds for these questions can be stored in a speech ROM and converted from digital to analog to give an audio reading of the questions to the patient via a speaker or headphones using audio jack 21f.

Keypad 26 has only a very limited number of keys, such as four keys 28-34 for the choices YES, NO, NOT SURE (N.S.), and NEXT QUESTION. Pressing an answer key 28, 30, 32 causes the answer chosen to be echoed in the display as input echo 25. For example, in FIG. 1, the patient has pressed the NOT SURE key, causing the text "NOT SURE" to appear in the display as input echo 25.

However, the answer echoed on the display at 25 is not considered the patient's final answer until the patient presses a NEXT QUESTION key 34, which acts like the "Enter" or "Return Key" on a microcomputer. Until Next Answer key 34 is pressed, the patient can change the echoed answer by pressing one of the other answer keys, then press the "NEXT QUESTION" key to adopt it as his or her final answer.

As will be seen below, a patient is instructed that if he or she has answered a question by pressing one of answer keys 28, 30, 32 and "NEXT QUESTION" key 34 and afterwards wants to go back to that question, the test selector should be returned to the medical staff for resetting. Then a staff person uses control key 21b to illuminate control keypad 36, and presses backup key 37 to back up the display to the prior question. This enables the patient to enter a revised answer by one of keys 28, 30, and 32, followed by NEXT QUESTION key 34.

It has been found that this very limited set of keys makes it easy for even the typical non-computer-literate patient to use the test selector with little or no instruction. To the typical patient, these keys are as easy as, or easier than, as those found in elevator controls, simple household appliances, etc.

Figure 2:
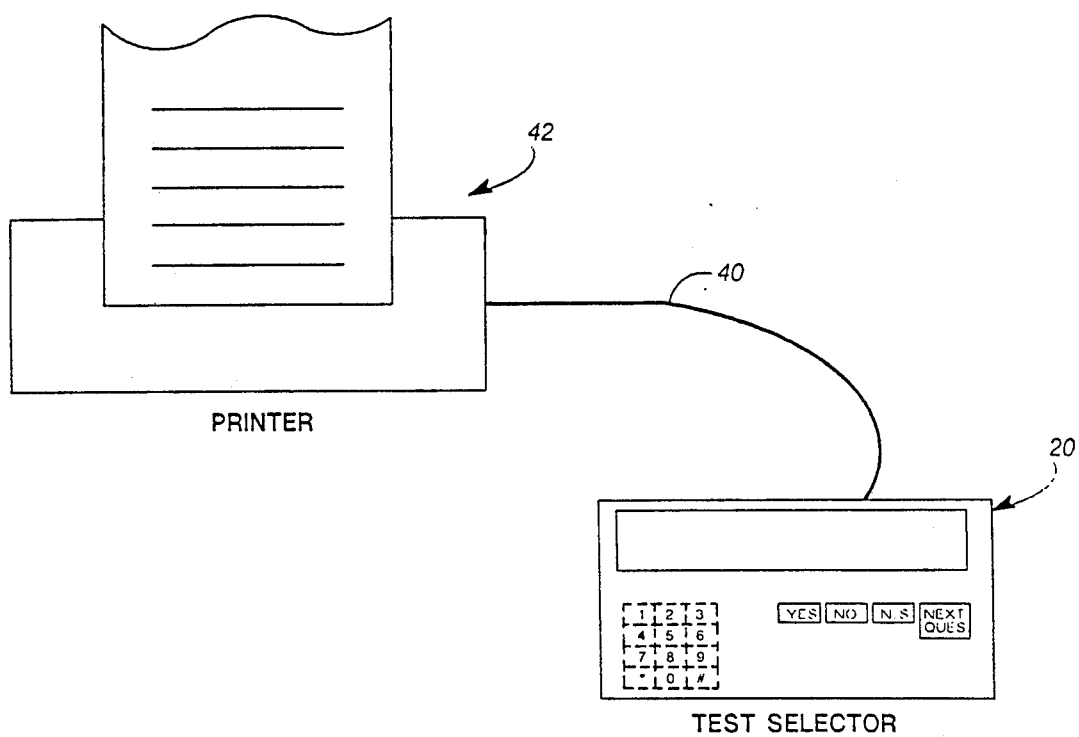
FIG. 2 is a diagram showing the test selector connected to a printer to produce printed output.

As shown in FIG. 2, when the patient has read and answered a full set of questions, test selector 20 can be attached by a printer cable 40 to a standard ASCII printer 42 to print out reports based on the patient's answers. A plug (not shown) on printer cable 40 is inserted into printer jack 21e.

Preferably, the printer has an input for serial data complying with the popular interface standard RS-232C of the Electronic Industry Association, and the handshaking between the test selector and printer is software controlled. Then cable 40 will only need three lines a line for data and control signals transmitted by the test selector and received by the printer, a line for data and control signals transmitted by the printer and received by the test selector, and a ground or common connection.

In such a case, printer jack 21e and its matching plug (not shown) can be simple miniature three wire stereo jacks, such as are found on audio equipment for connecting stereo headphones. Such jack and plug sets are compact, lightweight, and snap together and apart easily, making them much easier to use than standard 25 or 9 pin serial connectors for microcomputer equipment.

2. General Method of Operation

Figure 3A:
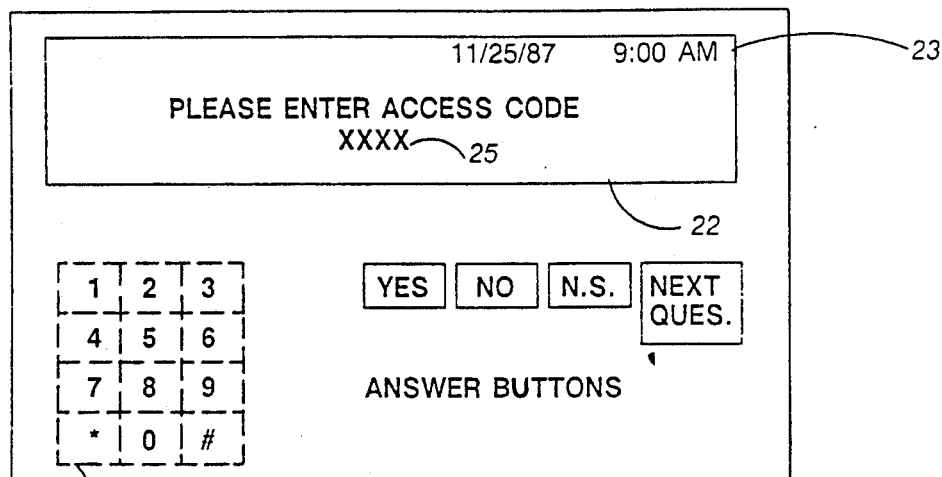
FIGS. 3A-3F are views of the display and control keys of the test selector when it is in various modes of operation.

In operation, the medical staff person administering the test (hereafter "staffer") controls the mode of the test selector by selecting from choices presented by display 22, as shown in FIGS. 3A-3F. When the test selector is first turned on, control keypad 36 is lit or otherwise made usable as shown in FIG. 3A, and display 22 prompts "PLEASE ENTER ACCESS CODE". In response, the staffer must enter a four digit secret access code (password) via control keypad 36. The four integers keyed in by the staffer are echoed on display 22 merely as X's to keep the access code secret.

Figure 3B:
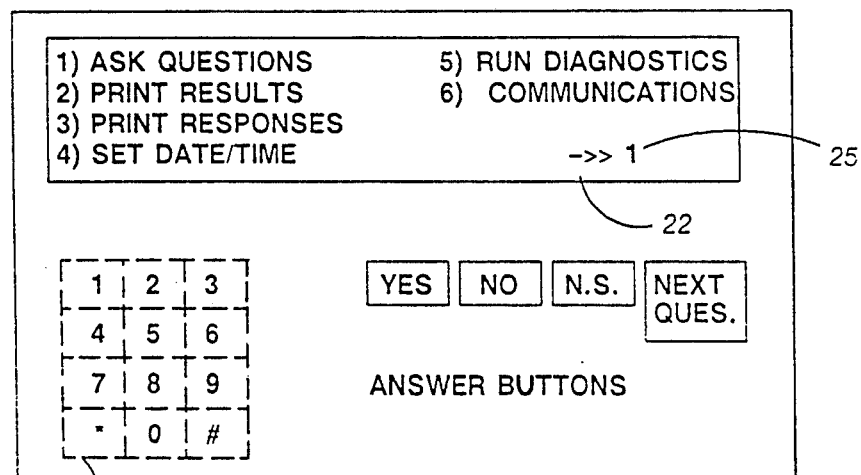

If the staffer's access code is correct, FIG. 3B, the display changes to an opening menu offering the following choices:

| | |
|---|---|
| 1) ASK QUESTIONS | 5) RUN DIAGNOSTICS |
| 2) PRINT RESULTS | 6) COMMUNICATIONS |
| 3) PRINT RESPONSES | |
| 4) SET DATE/TIME | |

The control keypad remains lit or otherwise usable for the staffer's choice, which appears as input echo 25.

Figure 3C:
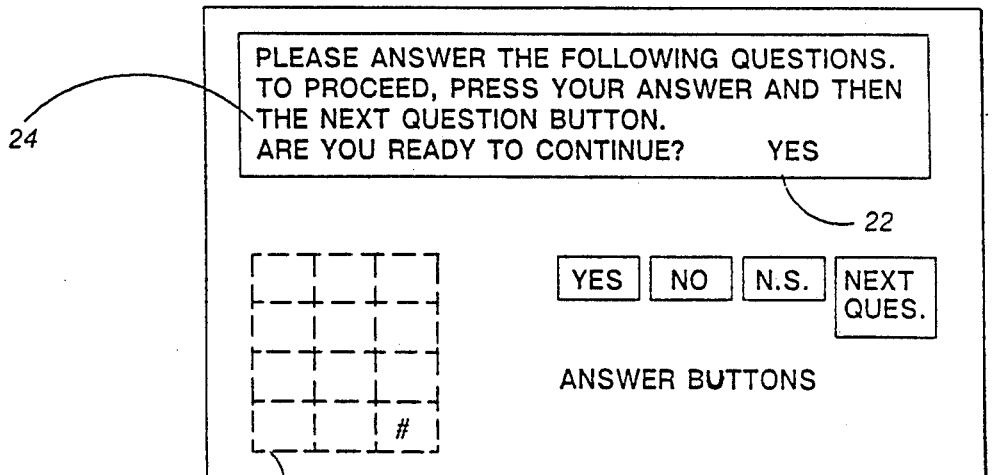

Suppose, as in FIG. 3B, that the staffer presses 1 on the control keypad for the selector to administer a questionnaire to a patient. Then as shown in FIG. 3C, the illumination of the control keypad is turned off, concealing it, and the display shows an introductory message and an initial prompt for the patient to confirm that he or she has read the message:

PLEASE ANSWER THE FOLLOWING QUESTIONS. TO PROCEED, PRESS YOUR ANSWER AND THEN THE NEXT QUESTION BUTTON. ARE YOU READY TO CONTINUE?

Then the display shows a brief series of introductory screens about the way the patient should operate the test selector. This introduction advances by one screen each time the patient presses an answer key followed by the NEXT QUESTION key to indicate that he or she is ready for the next instruction.

Figure 3D:
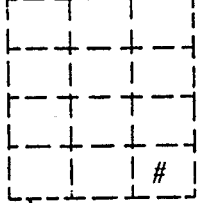
Figure 3E:
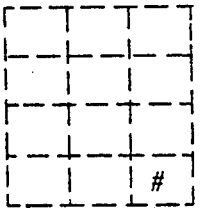
Figure 3F:
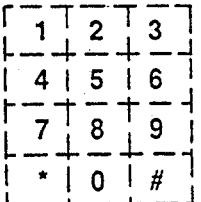

With the introductory screens completed, the first medical history question appears in display 22, as shown in FIG. 3D.

When the patient has read and responded to each of the prestored questions, a message appears in display 22 asking that the test selector be returned to the staffer for analysis. The next time any key is pressed, the test selector illuminates the control keys and displays a prompt for the staffer to enter his or her access code. If the staffer's access code is accepted, a command menu similar to that of FIG. 3B appears from which the staffer can choose the next mode of operation.

Usually the staffer's choice will be to press control key 2 to print a report for the patient's physician (see Appendix I) or control key 3 to print a "hard copy" of the patient's questions and answers for signature by the patient (see Appendix II). The printed copy for signature can include various notices and disclosures to the patient, and follow-up questions with blanks where the patient can fill in a response. For example, if the patient has answered "YES", he or she has allergies, a follow-up question will be printed at the top of the hard copy for completion:

WHAT ARE YOU ALLERGIC TO?

3. Connection to Work Station

Figure 4:
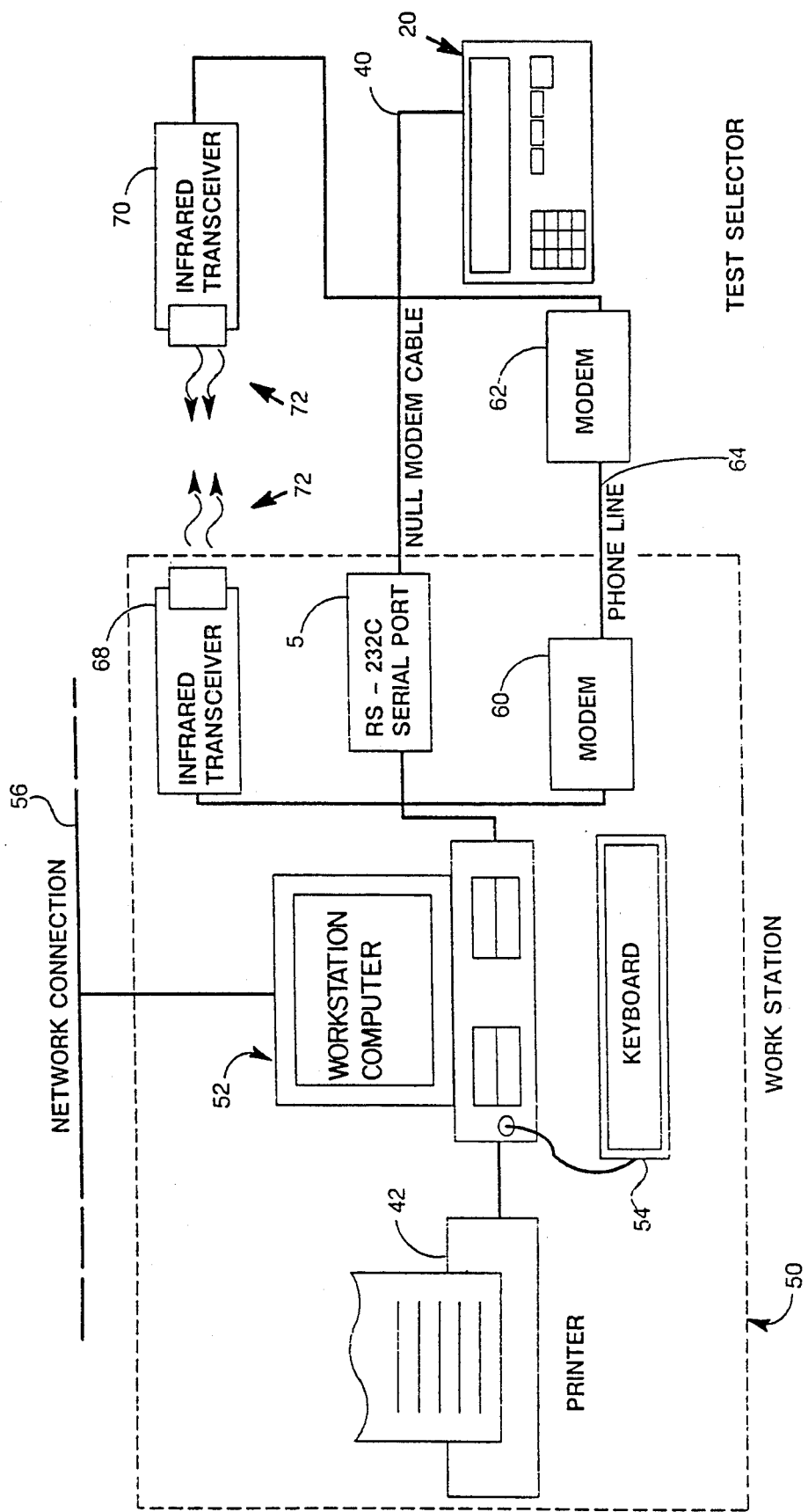
FIG. 4 is a diagram showing the test selector coupled to a computer terminal.

In addition to being printed out, the machine-readable reports and the patient's responses can be transmitted as shown in FIG. 4 to whatever computerized medical record-keeping or management system is being used by the patient's physician or hospital. For example, the physician or hospital may use a computerized workstation 50 having a microcomputer or terminal 52 with keyboard 54, a printer 42, and an RS-232C serial port 57 for data communications. The microcomputer or terminal 52 may be coupled to a larger system, such as a hospital or laboratory mainframe computer, by a network connection 56.

Test selector 20 can be directly coupled by a serial cable 40 to an RS-232C interface of the workstation for uploading of the question and answer data obtained from the patient, or downloading of data such as the patient's name, as entered on keyboard 54 of the workstation's computer 52, for use in the reports printed under direction of test selector 20.

If the test selector is being used in a location remote from the work station, each can be coupled for communication to a common phone line (external or intercom) by respective modems. In a preferred embodiment of the invention, to eliminate the need for actual mechanical coupling of electrical connectors the workstation is provided with an infrared transceiver 68 which uses infrared signals 72 to transfer data to and from a similar infrared transceiver 70 that is coupled to test selector 20.

4. Circuit Construction

Figure 5:
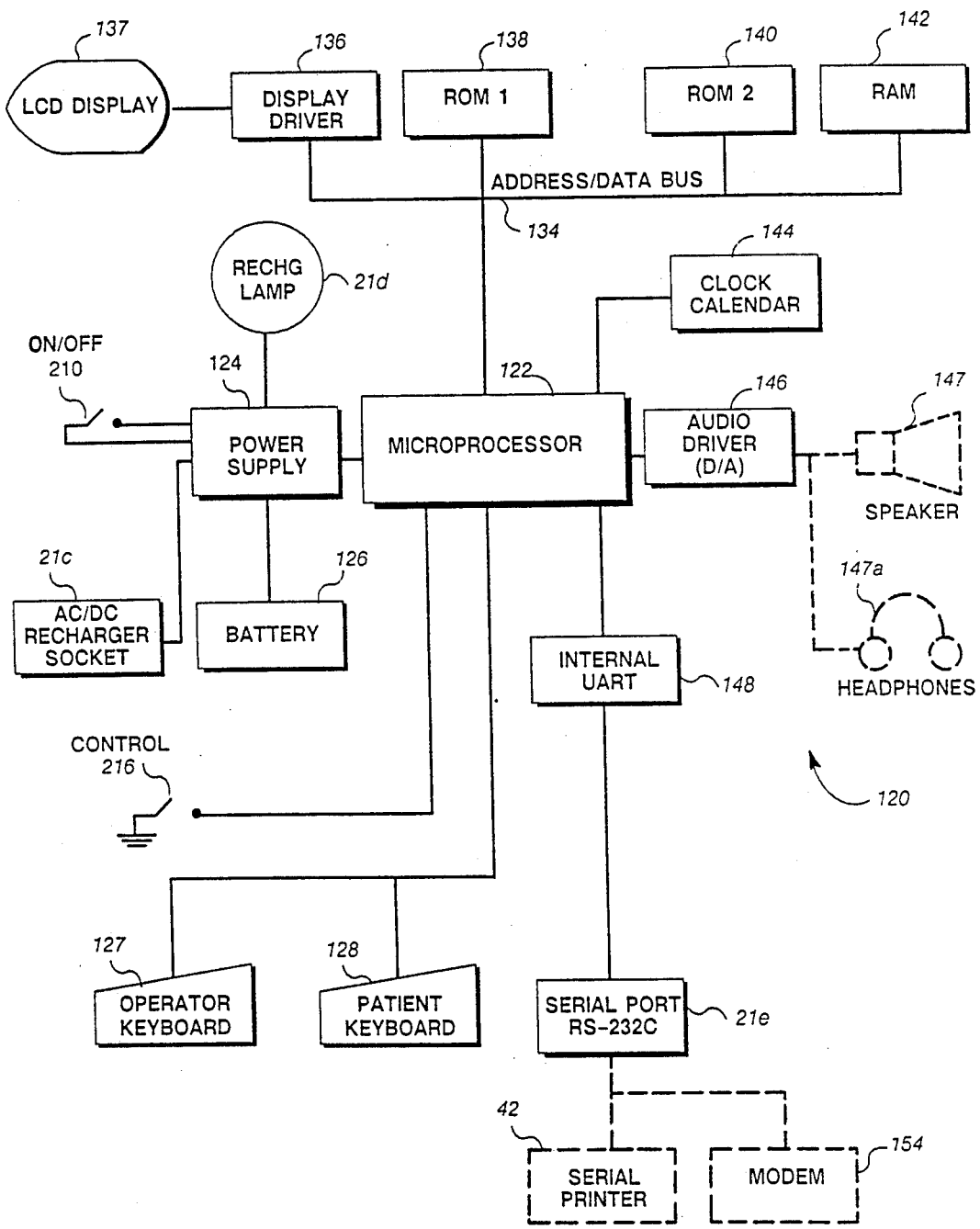
FIG. 5 is a functional block diagram of the main hardware components used in the test selector, and their interconnection.

The test selector of the present invention can be conveniently and inexpensively realized by means of the microprocessor-based circuit 120 shown in the functional block diagram of FIG. 5. A microprocessor 122 receives its operating voltage from a power supply 124 that regulates the power from a rechargeable batter 126. The power supply is controlled by the ON/OFF switch 21a of FIG. 1 and can receive external electrical power for recharging battery 126 via AC/DC recharger socket 21c. Charging lamp 21d is lit whenever power supply 124 is recharging battery 126 from the external power. When battery 126 is fully charged, the charging automatically stops and charging lamp 21d goes out.

An operator keyboard 127 and a patient keyboard 128 are each coupled to ports on the microprocessor to provide digital input data from the medical staff and patients. Control switch 21b is connected to an input terminal of the microprocessor. When the patient is answering questions, the operator keyboard 127 is not illuminated to conceal it. However, if a staffer presses control switch 21b, microcomputer 122 relights control keypad 127 so the staffer can use backup key 37 of FIG. 1 to return the display to a previous question for the patient.

The microprocessor has a multiplexed address and data bus 134 by which it is able to send data bytes to a display driver 136, read-only memories ROM 1 and ROM 2, and a scratchpad random access memory RAM 142. Display driver 136 delivers ASCII text data to a display 137, which, for example, can be a supertwist liquid crystal display (LCD) capable of displaying four lines of forty characters. Preferably the character set includes not only the usual 128 ASCII characters, but an additional 128 symbols which include the international letters and symbols needed for foreign alphabets.

ROM 138 serves as a primary read-only memory in which can be stored the operating program for the microcomputer and the text used for the test selector's questions, answers, and reports. ROM 140 is optional, and when present serves as a secondary read-only memory which stores an alternate language version of the text data for the test selector's questions, answers, and reports. Thus, ROM 2 makes it possible for the questions, answers, and/or reports to be displayed by display 137 and/or printed out in a second language.

It is an important feature of the invention that ROMS 1 and 2 can be easily replaced by an untrained medical staffer. For example, they can be combined in ROM cartridge 38b for easy removal and insertion into recess 38a of side 38 of the test selector. This enables the control program, the questions asked, and the recommendations to the doctor to be easily updated to the latest version.

Suppose ROM 1 holds English text because the physician's office primarily uses English, but the patient primarily reads Spanish. If ROM 2 stores a Spanish version of the text of the questions, answers, and reports, by a software selection portions of ROM 2 can be addressed in place of those in ROM 1 to display the questions and answers in Spanish. The questions and answers, and follow-up questions can also be printed in Spanish. However, the staff can revert back to ROM 1 for an English version of the questions and answers and an English report of results to the physician.

A clock/calendar chip 144 is provided so that the time and date 23 can appear in the display (FIG. 3A) and be stamped on the printed reports and questionnaires. Moreover, since medical information and practice are constantly being updated, if desired the time and date information can be used to automatically check an expiration or date stored with the medical data in ROM 1. If the data in ROM 1 becomes older than this date, a notice can be included in the display or in the printouts, or the test selector can be prevented from functioning until the ROM is updated.

If desired, an audio driver 146 can be coupled to an output port of microprocessor 122, to enable the microprocessor to send tones, sounds, or voice information to users via an external speaker 147 or headphones 147a via the audio jack 21f of FIG. 1.

To convert the microprocessor's parallel data into serial signals, microprocessor 122 includes an internal universal asynchronous receiver/transmitter (UART) 148 which is coupled to an output RS-232C-compatible serial connector 21e. To print connector 21e.

In the embodiment of the example, microprocessor 122 can be an eight-bit Hitachi Ltd. HD6303 chip of low power CMOS construction. Mode 3 of this single chip processor configures it to run as a microprocessor with a sixteen-bit (64K) address bus and a eight-bit data bus. An external crystal is used to maintain a clock frequency of about 4 MHz. The relatively large 64 kilobyte (KB) external address space easily enables external RAM 142 to be a two-KB scratchpad memory, and the external ROM 138 to be provided with about 8 KB of program code and 24 KB of text and related data for the questions, answers, and reports. Moreover, there is still plenty of room for second language ROM 140.

The program for this microprocessor, was written in Microtext Assembler language, which is compatible with the assembler language produced by Motorola. A source code listing for a first embodiment is attached to this application as Appendix III, and a source code listing for a second embodiment of the invention is attached as Appendix IV.

5. Software Construction a. Generally

Figure 6:
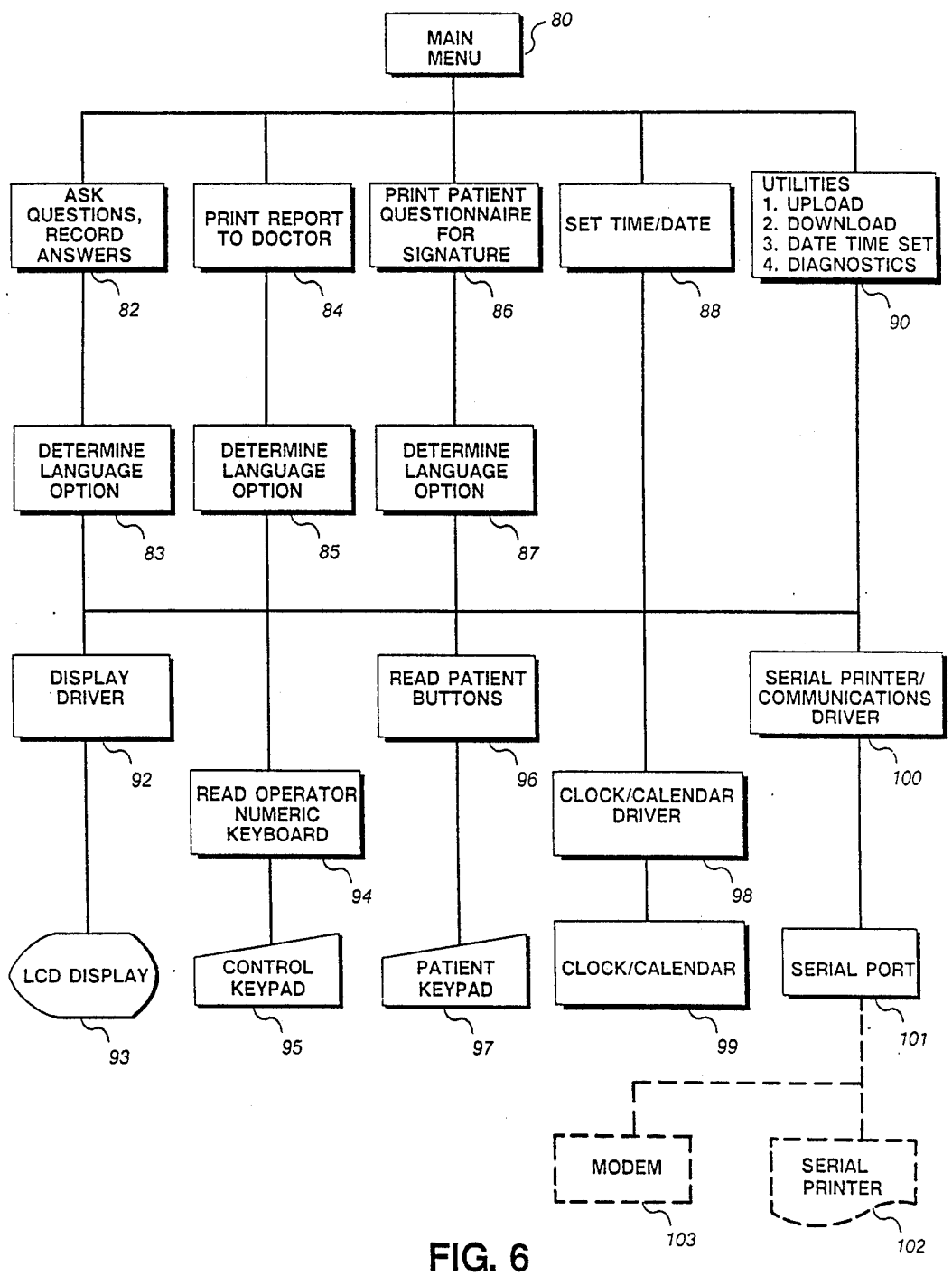
FIG. 6 is a diagrammatic representation of a program used to control the test selector, showing a functional representation of the systems software.

The various operations carried out by the microprocessor-based circuit of FIG. 5 are represented in the functional block diagram of FIG. 6. The main operating routine displays the Main Menu 80 (see FIG. 3B), prompting the medical staff to choose one of the main subroutines by entering a menu number via the control keypad.

The main subroutines are those for Asking Questions and Recording Answers 82, Printing a Report for the Doctor, Printing the Patient's Questions and Answers for Signature, Setting the Time and Date 88, and various Utilities 90. If optional language ROM 2 is installed, whenever 82, 84, or 86 is selected, the language that should be used is next determined by a corresponding language option routine 83, 85 or 87.

An important feature of the invention is that reports and questionnaires can be automatically date stamped, and the medical information in ROM 1 can be automatically checked to see if it should be renewed. However, this requires that subroutine 88 be provided to enable the clock/calendar chip 144 to be properly set by the medical staff or at the factory prior to shipping.

Subroutine 90 includes various utilities, such as dedicated communication programs for uploading or downloading data to workstation 50 of FIG. 4 or running diagnostics to check circuit and data integrity.

Supporting the above-mentioned high-level subroutines ar various lower-level input/output routines that interface with the hardware. Display driver 92 manages the data flow to LCD display 93. The subroutines 94 and 96 respectively get staffer and patient input from the control and patient keypads. Clock/calendar driver 98 makes clock/calendar 99 software accessible, and drivers 100 for the serial printer 102 and serial communications control input/output to serial port 101 or an external modem 103.

b. Main Menu Routine

Figure 7:
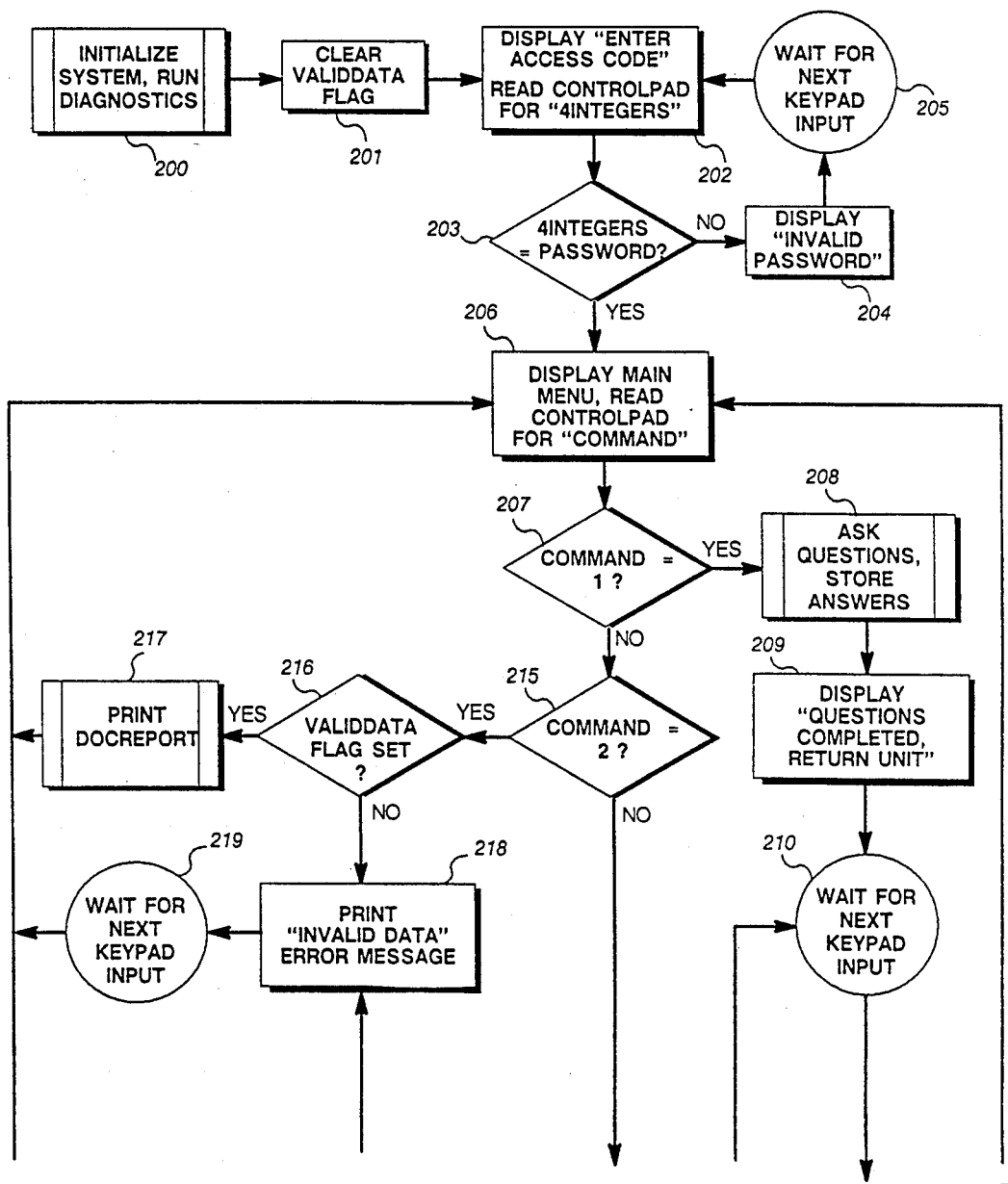
FIG. 7 is a flowchart of the Main Menu program shown in FIG. 6.
Figure 7:
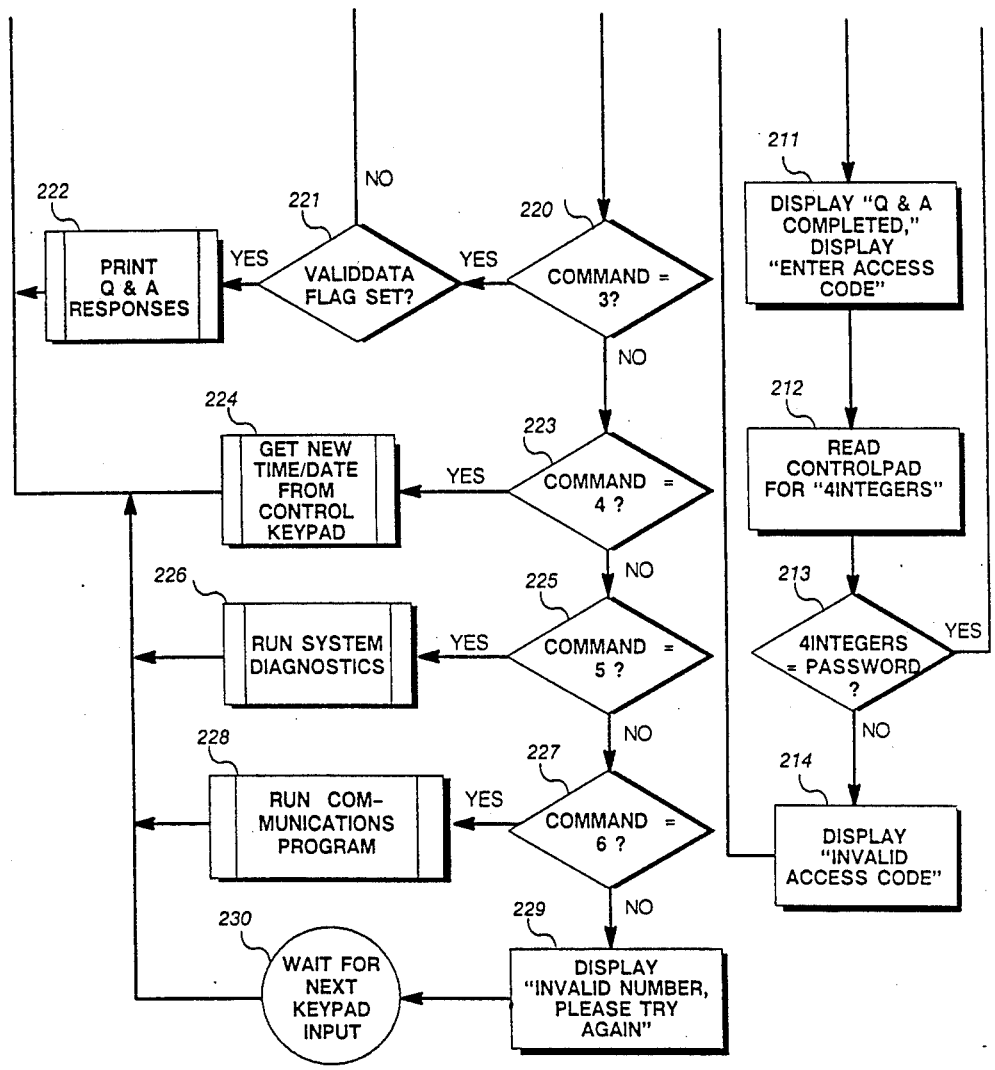

As shown in FIG. 7, Main Menu routine is the first routine called when power is provided to the microprocessor system. At Step 200 the system is initialized and diagnostics run, after which at Step 201 a flag called VALIDDATA is cleared. The message "ENTER ACCESS CODE" shown on display 22 by STEP 202, and the control pad read for the secret four-integer access code entered by the medical staffer. If Step 203 determines that the four integers read are not a valid access code, Step 204 puts "INVALID PASSWORD" on display 22, and at Step 205 this error message is left in place until there a further input is read from the control keypad at Step 202.

When Step 203 finds that a valid access code has been input, at Step 206 the Main Menu of FIG. 3B is displayed, and the medical staffer asked to enter a command integer 1-6. If the command integer is 1, Step 207 calls a subroutine ASK QUESTIONS, STORE ANSWERS at Step 208. This subroutine administers the prestored medical questionnaire to the patient and stores his or her answers. As subroutine 208 is completed, it sets the VALIDDATA flag (step not shown). Next at Step 209 "QUESTIONS COMPLETED, RETURN UNIT" is displayed to the patient. Step 210 keeps this message on the display until the next keyboard input.

When the patient returns the test selector to the medical staffer, and a key of the control pad is touched, the wait at Step 210 ends and "Q&A COMPLETED, ENTER ACCESS CODE" is displayed to the medical staffer. When Step 213 find that the staffer again enters a valid four-integer access code, a jump is made at Step 214 back to the main menu display of Step 206. But if the code is wrong, a jump is made back to Step 210 to request the access code again.

Suppose that a set of valid question and answer data has been taken, a proper access code entered by the medical staffer at Step 212, and a jump made back to the Main Menu of Step 206. The medical staffer will probably now select a printout option, either command integer 2 (prints a report for the doctor) or 3 (prints the questionnaire with follow-up questions, etc.). If command integer 2 is selected, Step 207 will be a "NO" and Step 215 will be a "YES". Step 216 then checks to see if the VALIDDATA flag is set to avoid printing partial, meaningless, or corrupted data. If VALIDDATA flag is set, at Step 217 a subroutine PRINT DOCREPORT prints a report with test recommendations for the doctor. An example of such a report appears as Appendix I.

If at Step 216 the VALIDDATA flag is found not to be sent, a jump is made to Step 218, which prints an error message "INVALID DATA", after which Step 219 waits for the next keypad input and then causes a jump back to the Main Menu 206.

When the command integer selected by the staffer at Step 206 is a 3, Steps 207 and 215 both "NO", and Step 220 is "YES". This causes Step 221 to check if the VALIDDATA is set: if it is, the PRINT Q&A RESPONSES subroutine of Step 222 prints the questions and the patient's answers, and then jumps back to the main menu. But if Step 221 finds that the VALIDDATA flag is not set, a jump is made to print the error message of Step 218, pause until the next key input at step 219, and jump back to the main menu of Step 206.

Of course, the staffer may select a housekeeping function at Step 206, such as command integer 4, which passes as a "NO" through steps 207, 215, and 220, but is a "YES" for Step 223. This causes the subroutine of Step 224 to get a new time or date from the control keypad, i.e., let the medical staffer set the clock/calendar.

Or the staffer may select command integer 6, which at Step 227 causes a communications subroutine 228 to run so that data or patient information, such as medications, birthdate, or responses to questions, can be transferred to or from the test selector to a work station or the like.

If the command integer is other than 1-6, the program will pass to Step 229, which puts "INVALID NUMBER, PLEASE TRY AGAIN" on the display. After a wait at Step for 230 for keypad input, the routine jumps back to the Main Menu. Note that, barring a crash of a subroutine, the Main Menu routine runs in an endless loop.

c. Accommodating A Second Language

Figure 8A:
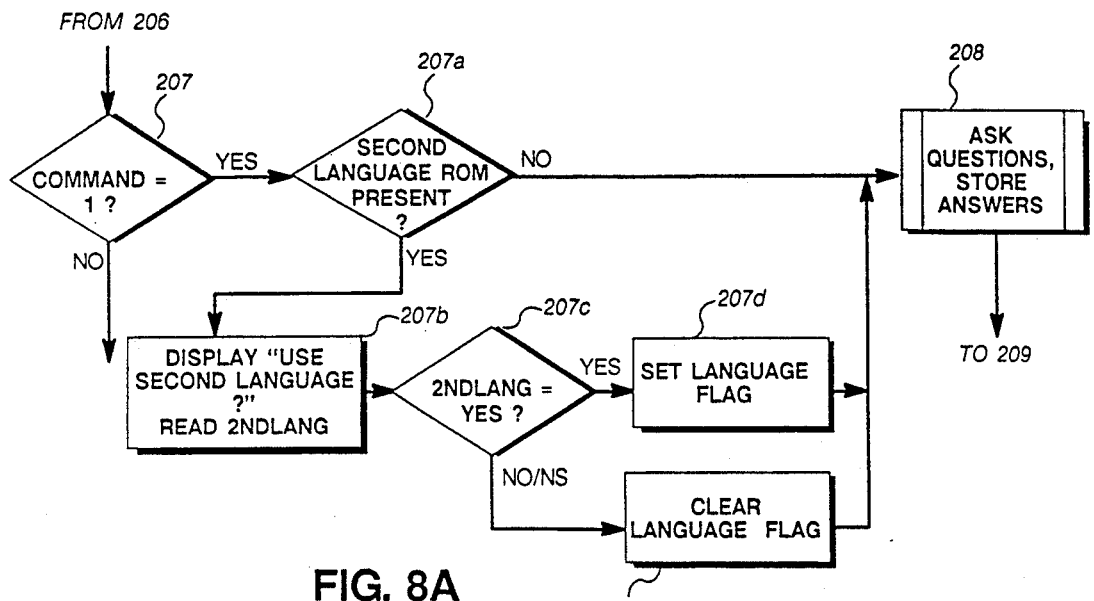
FIGS. 8A, 8B, and 8C are partial flowcharts showing how portions of the program of FIG. 7 can be modified to give the option of a second language for the display and printed reports of the test selector.

If the second language ROM 2 of FIG. 5 is present, there must be additional steps added to the Main Menu routine to allow the option of using the second language. For example, the partial flowchart of FIG. 8A adds such steps in FIG. 7 between steps 207 and 208. If in FIG. 7 command integer 1 is selected, Step 207 of FIG. 8A is "YES", transferring control to Step 207a, which checks to see if an additional language ROM 2 is present. If it isn't, Step 207a is a "NO" and the normal path to the subroutine of Step 208 is followed.

But if the second language ROM 2 is present, a "YES" at Step 207a causes Step 207b to put "USE SECOND LANGUAGE?" on display 22. The staffer's response is either "YES", "NO", or "NOT SURE" read from the Patient Keypad, which is stored as 2NDLANG. If 2NDLANG is a "YES" at Step 207c, a LANGUAGE flag is set at Step 207d, and the program moves on to subroutine 208. Subroutine 208 can then check to see if the LANGUAGE flag is set, and if it is, get text for display 22 from locations in ROM 2 rather than in ROM1, causing the second language to be displayed to the patient.

Even if the second language ROM 2 is present, the staffer may have decided to use the primary language, in which case 2NDLANG will be a "NO" or NOT SURE at Step 207c, and the LANGUAGE flag will be cleared at Step 207e before a branch to subroutine 208.

Figure 8B:
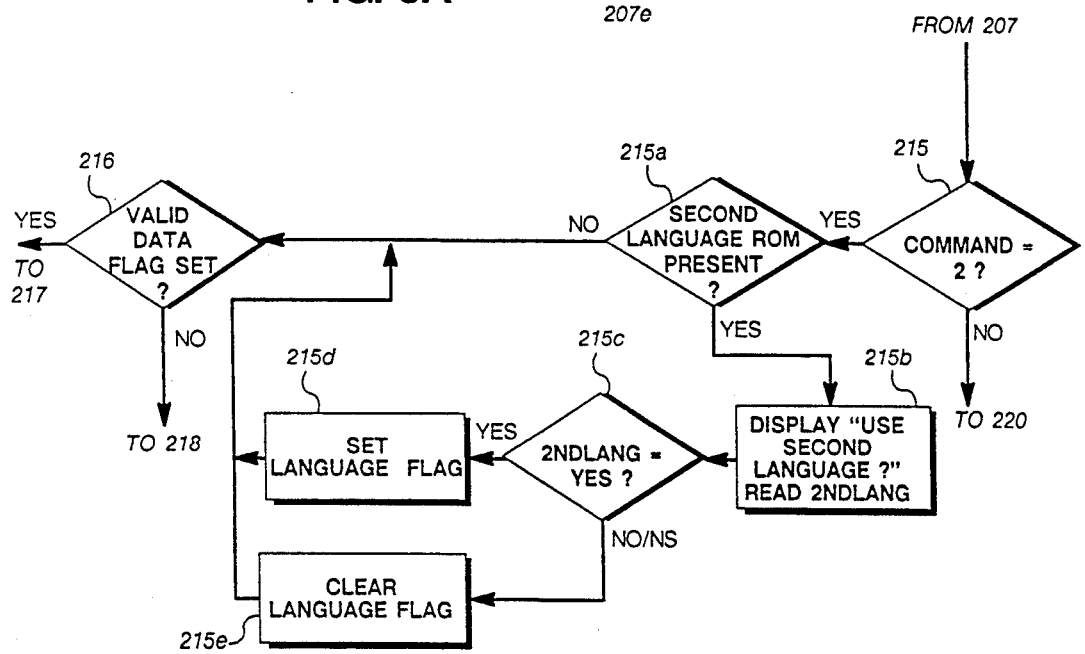
Figure 8C:
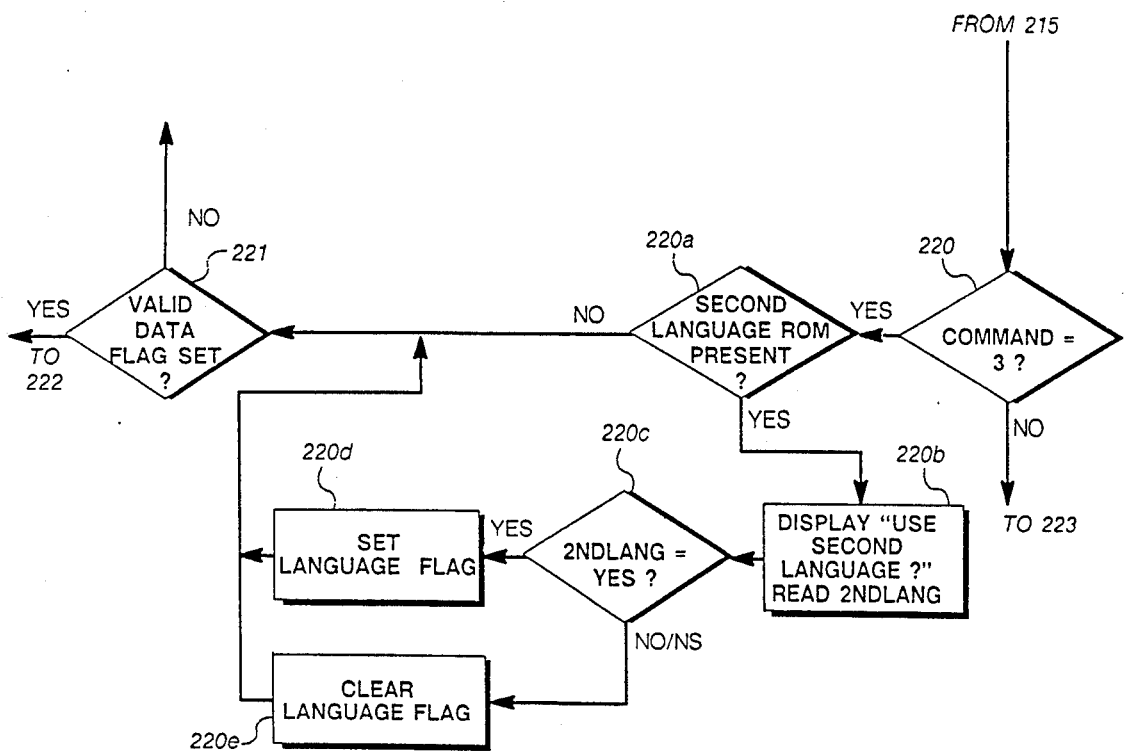

In a similar manner, as shown in FIG. 8B, second language steps can be inserted between Steps 215 and 216 of FIG. 7 to affect the language in which the Doctor's Report is printed. If Step 215a finds that ROM 2 is not present, the usual transfer to Step 216 to check the VALIDDATA flag is made. But if ROM 2 is present, Step 215b puts the question "USE SECOND LANGUAGE?" on the display. If the staffer enters "YES" on the patient keyboard, this is detected by STEP 215c, and the LANGUAGE flag is set at Step 215d. Subroutine 217 of FIG. 7 can check to see if the LANGUAGE flag is set, and if it is, get text for printing from locations in ROM 2 rather than in ROM 1, causing the second language to be used for the Doctor's Report.

If the staffer instead enters "NO" or "NOT SURE", Step 215e clears the LANGUAGE flag and jumps to Step 216.

The additional steps of FIG. 368C work in a manner similar to those of FIG. 8B, except that they are inserted between Steps 220 and 221 of FIG. 7 and it is the PRINT Q&A Responses subroutine 222 that must use the 2d language text in ROM 2 if the LANGUAGE is set.

d. Ask Questions and Store Answers

Figure 9:
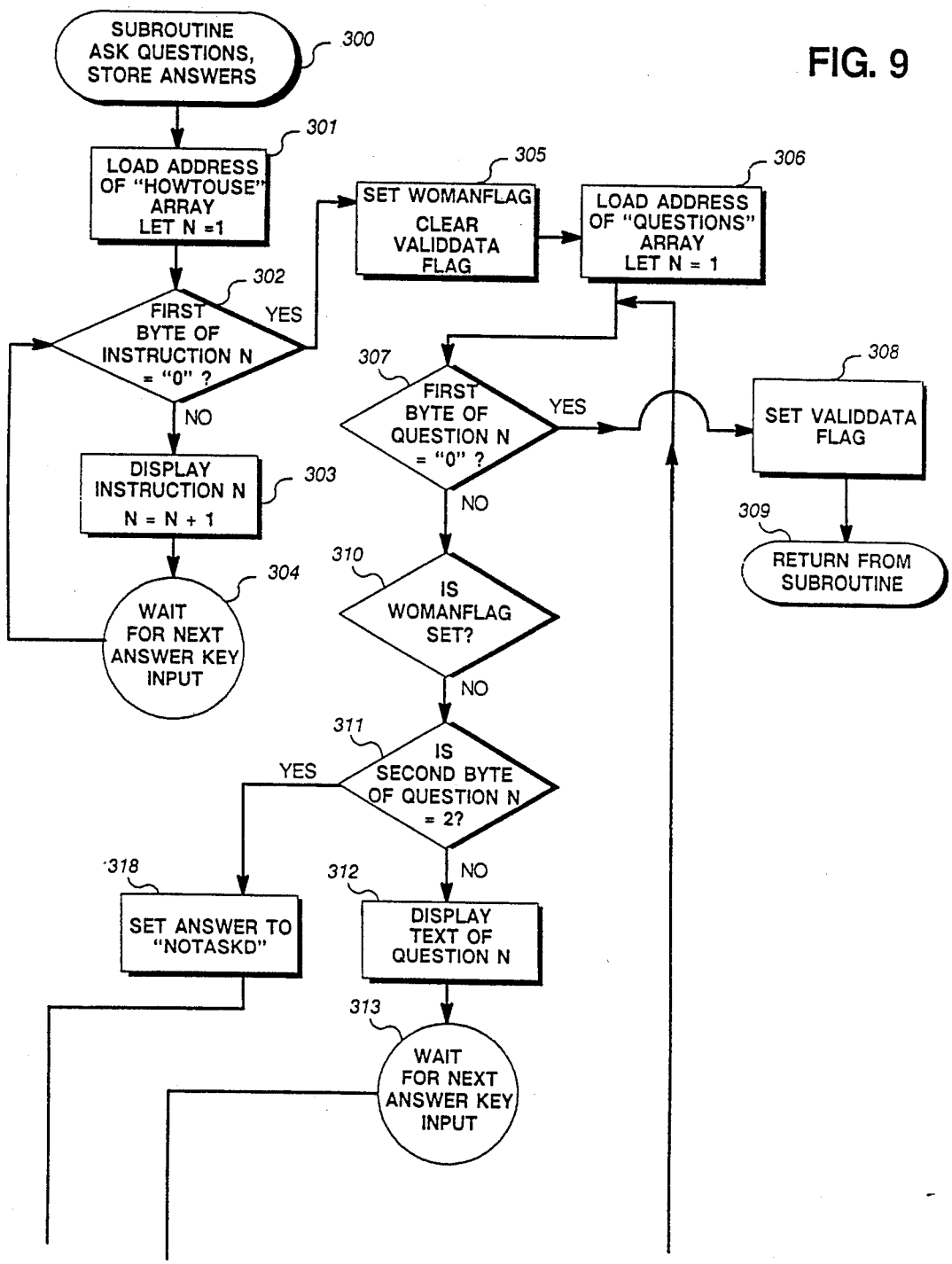
FIG. 9 is a flowchart of a first embodiment of the "Ask Questions, Store Answers" subroutine of FIG. 7.
Figure 9:
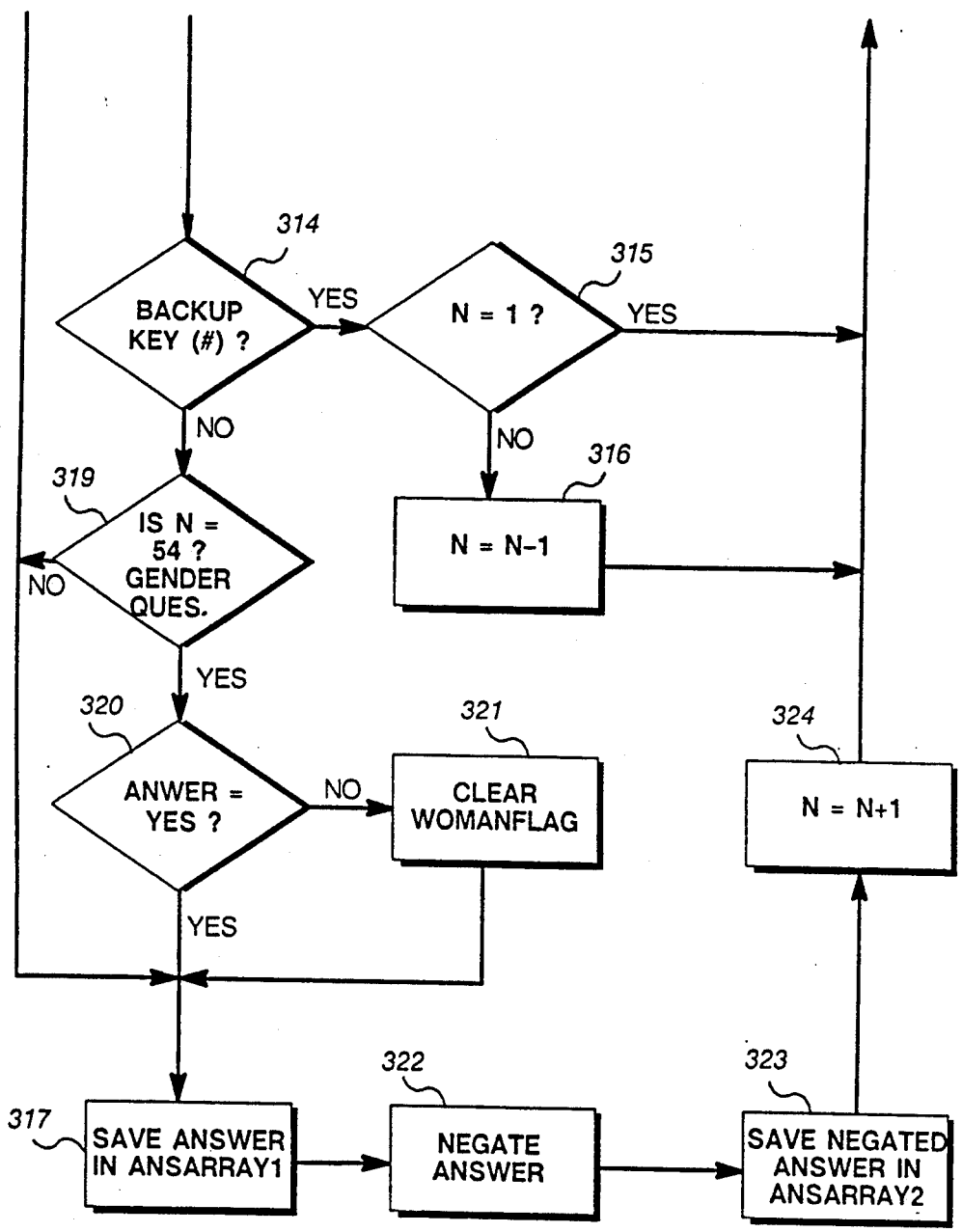

Next, FIG. 9 shows in some detail how the ASK QUESTIONS, STORE ANSWERS subroutine 208 of FIG. 7 is effected. Beginning at Step 300, the address of the array "HOWTOUSE" is loaded and saved for reference. This array has the instruction screens for the patient explaining how the test selector keys are used to answer questions. The data for the instruction screens are saved as character strings in memory, each starting at a known location. The last screen is a dummy which only contains one byte of data, hexadecimal 0 (0h).

Thus, Step 302 tests the first byte of Instruction N for 0h. The Instruction screens have some other hexadecimal number in the first byte, so Step 303 causes Instruction screen N to be displayed and N incremented. Then Step 304 causes a pause until the next answer keypad input, after which there is a jump to Step 302 to begin to check the first byte the next Instruction Screen.

Finally, the first byte in the last (dummy) screen is detected, indicating that all the Instruction Screens have appeared to the patient on display 22. A jump is made to Step 305 where the sex or WOMANFLAG is set as a default and the VALIDDATA flag cleared as a default.

The address of the QUESTIONS array is found and stored at Step 306, and the index N is restarted at N=1.

Before proceeding further, it is necessary to explain the format and contents related to each question stored in the read-only memory ROM 1. Each question for the patient is stored in memory as part of a Question Structure of the form:

<Question Number> <Assoc Flag> <Question Class> <Text String>

This formatting can be understood as follows:

<Question Number> is the number of the question, except in the case of the last or dummy question, which is given a Question Number of 0h to indicate the end of the questions.

<Assoc Flag> is a code in which "0" indicates a default or ordinary question A "1" indicates that the question has an associated text string, such as a follow-up question or a comment. A "2" indicates a question that should only be asked of females.

<Question Class> is a sorting code for identifying the type of question, as follows: 1=Lab Test Question, 2=Anesthesia Question, 3=General Heath Question.

<Text String> is a string of ASCII characters making up the text of the question, including any characters reserved to represent carriage returns and line feeds, with the last byte being a 0h to indicate that the string has ended.

If <Assoc Flag> is 1, the Question Structure further includes from one to three more character strings, identified as:

<Follow-up Question String>
<YES Comment String>
<NO Comment String>

The follow-up question is necessary when the patient indicates some complication. For example, if the patient says he or she had an EKG test in the last two months, the follow-up asks where, providing a blank line to be filled in the printout of Questions and Answers.

The YES or NO comment strings put short statements in the report to the doctor of points to be noticed because of a YES or NO reply. For example, "Patient has loose teeth". "Patient may not have had an EKG in the last 2 months."

Returning to the ASK QUESTION, STORE ANSWERS subroutine of FIG. 9, at Step 307 the first byte of the Nth Question Structure in the Array is examined to see if it is 0. If it is, we must have reached the dummy question that indicates the end of the questions. A branch is made to Step 308, which sets the VALIDDATA flag and at Step 309 a Return From Subroutine is made.

However, at first N=1 and the answer at Step 307 is "NO". Although Step 310 checks to see if the WOMANFLAG is set, which initially it always is because of Step 305. Later, Question 54 will ask if the patient is a woman, clearing the WOMANFLAG if the patient answers that he is a man. Questions that follow Question 54 can then be omitted, depending on the patient's sex.

Therefore, at first the program will always jump to Step 312, which puts the text of the Nth question on the display and waits for an answer at the patient's keyboard. Assuming there is no backup to an earlier question, and the gender question (N=54) has not been reached, Step 317 saves the patient's YES, NO or NOT SURE answer as distinguishable binary codes in the Nth entry of an answer array ANSARRAY1. At Step 322 the two's complement of the answer code is saved in a second answer array ANSARRAY2, N is incremented by Step 324 and a jump is made back to Step 307.

The reason for having a second answer array that is the negative (two's complement) of the first array is for checking against loss or corruption of data. The codes in ANSARRAY1 can be added to yield some number D. The codes in ANSARRAY2 can be added to yield some number D*, which should be the complement of D. Therefore, only if the data is not corrupted $D+D^*=0$. That is, array ANSARRAY2 enables a simple integrity check of the data before using or printing the stored data.

Now suppose the gender question 54 "ARE YOU A FEMALE?" is reached at Step 319. The answer at both Steps 319 and 320 will be "YES" for a female, leaving the WOMANFLAG set. A male will answer "NO" at Step 320, causing Step 321 to clear the WOMAN-FLAG.

With the patient's sex determinable by WOMAN-FLAG, Step 310 becomes meaningful. As previously explained, if the second byte of a Question Structure is 2h, the question is only to be asked of females. Therefore, suppose Step 310 determines that "NO", the WOMANFLAG is not set (patient is a male), and Step 311 determines that the question's second byte indicates that it is for women only. A branch is made to Step 318, which sets the answer to "NOTASKD" (not asked). By contrast, if Step 312 does not find a 2 in the second byte of a Question Structure, the question is displayed to both males and females by Step 312.

We turn next to the backup steps 314, 315, and 316 in FIG. 9. Step 314 determines if the key pressed was the backup key on the control pad. If it was, Step 315 checks to determine if the current value of N is 1, the lowest it can be. If it is, N is not decremented, i.e. there is no backup because we are already at Question 1. But if N is greater than 1, it is decremented by Step 316, which backs up the display to the previous question. Logic for the backup mode to skip over questions that were not asked due to gender, is also built in.

As explained above, the ASK QUESTIONS, STORE ANSWERS routine ends when at Step 307 a question is encountered whose question number is 0. A branch is then made to Step 308 to set the VALID-DATA flag, after which Step 309 executes a Return From Subroutine.

e. Printing A Doctor's Report

Once a set of valid answers has been taken from the patient, from the main menu (FIG. 3B) the medical staffer can choose to print a report for the doctor, including suggested tests. The staffer takes back test selector 20 from the patient, and using printer port 21e of FIG. 1, connects it to a standard serial printer 42 as shown in FIG. 2.

To print the report for the doctor, at the main menu (FIG. 3B, FIG. 7, Step 206) the staffer selects command 2. Because Step 207 is "NO" and Step 215 is "YES", next Step 216 checks to see if the VALIDDATA flag is set. If it is, there is a valid set of data to print, and subroutine PRINT DOCREPORT is called at Step 217.

Figure 10:
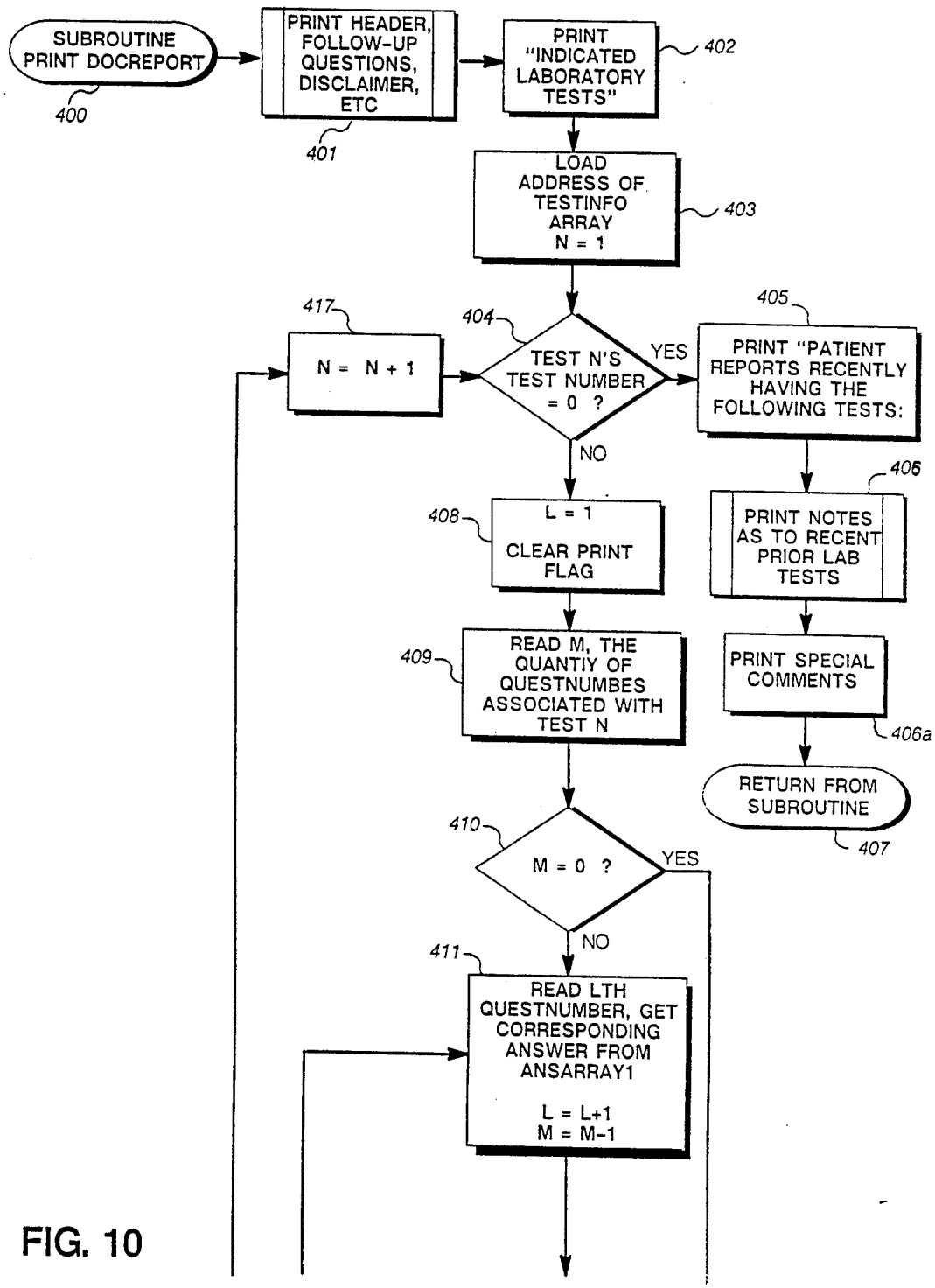
FIG. 10 is a flowchart of the "Print Docreport" subroutine of FIG. 7, which prints a report for a doctor.
Figure 10:
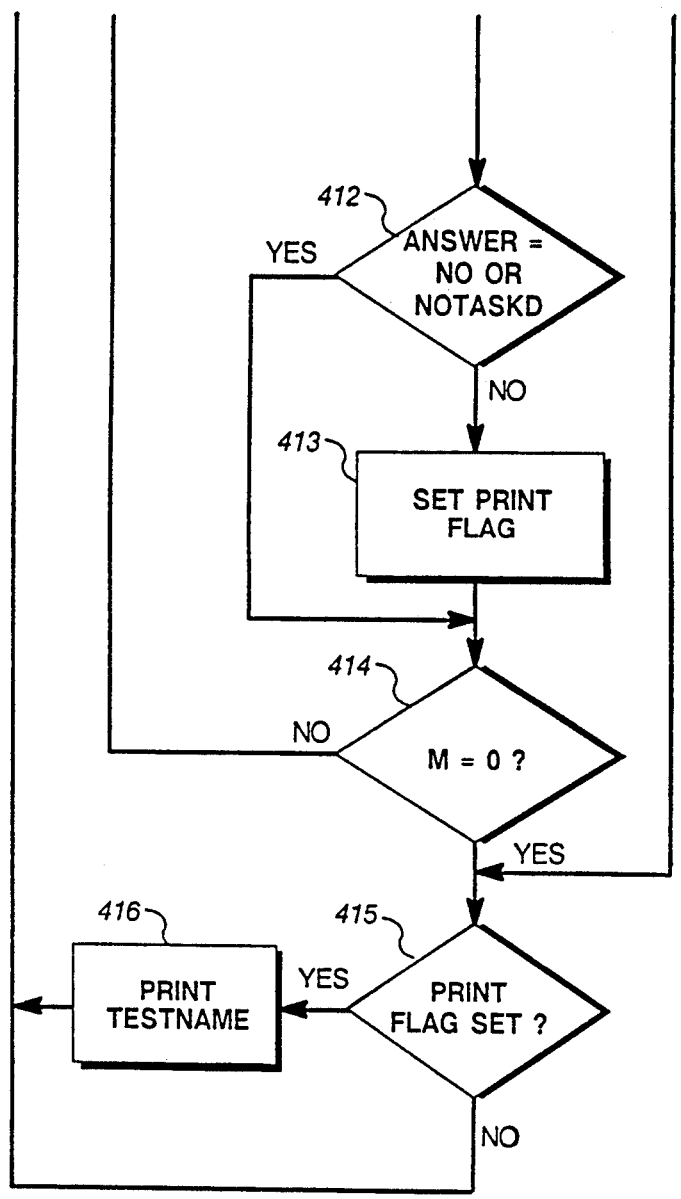

The PRINT DOCREPORT subroutine is shown in more detail in FIG. 10. The subroutine begins at Step 400 and moves to Step 401, where a header for the report is printed (see Appendix I) that includes blanks for handwritten insertion of patient information.

Next, any Follow-Up Questions associated with questions to which the patient has answered YES are printed. For example, if the patient has answered "YES", he or she has allergies, the follow-up question printed will be:

WHAT ARE YOU ALLERGIC TO?

The text of a Follow-Up Question is stored in memory in the previously mentioned Question Structure after the question to which it is associated. Also stored in memory is an array called SPCQST which tells STEP 401 which YES/NO questions have associated Follow-Up Questions, which answers (YES, NO, NOT SURE) should cause a Follow-Up Question to be printed, and the address of each Follow-Up Question.

Next, Step 401 prints a disclaimer (see Appendix I) that includes information as to the basis for the test recommendations and a cutoff date beyond which the test guidelines stored in the ROM memory should not be regarded as valid because they may need updating.

Step 402 then prints a heading "INDICATED LABORATORY TESTS" Then at Step 403 an indexing number N is set equal to 1, and the address of an array TESTINFO, which stores information about each test, is loaded.

For each test, there is an information entry in TESTINFO according to the following format:

<TESTNO> The number of the test.
<QUESCOUNT> A number indicating how many Question Numbers are stored in <QUESADDS>
<QUESADDS> A series of address pointers, each indicating the address of a question that might give rise to an order for this test.
<TESTNAME> The name of the test (ASCII string).

The last test entered in TESTINFO is a dummy, the TESTNO of which is 0 to indicate there are no more tests.

Therefore, at Step 404 the TESTNO of the Nth item in TESTINFO is checked to see if it is zero. If it is, the program has reached the final or dummy test and can proceed to Step 405. However, usually the TESTNO of the Nth item in TESTINFO is not zero, and the program proceeds to Step 408, where an indexing variable L is set to 1 and a flag called PRINT is cleared.

Then at Step 409 the variable M is set equal to the QUESCOUNT associated with the Nth item in TESTINFO. If $M=QUESCOUNT=0$, there is no question that could give rise to an order for the Nth test, and a jump is made to Step 415. Since the PRINT flag was cleared in Step 408, the result at Step 415 will be a "NO", causing a jump to Step 417, which increments indexing variable N.

However, usually M=QUESCOUNT >0 because one or more questions could give rise to an order for the Nth test. At Step 411 the Lth question address pointer stored in the field <QUESADDS> is read, and the patient's corresponding answer for this question pointed to is read from the array ANSARRAY1.

For example, suppose N=1, so that the printing program is computing whether to set the PRINT flag to print the name of the 1st TEST under the heading "INDICATED LABORATORY TESTS". Step 409 goes to item 1 of the array TESTINFO, where it finds the entries:

```
<TESTNO>
<QUESCOUNT> 13
<QUESADDS> Q01, Q02, Q03, Q04, Q05, Q06,
    Q07, Q08, Q10, Q11, Q12, Q54, Q65
<TESTNAME> The name of the test (ASCII
    string).
```

Suppose the current value of L=1. Then the first (L=1) question pointer Q01 is read from the field QUESADDS, and used to access the information about the indicated question in the QUESTIONS array. In particular, the indicated Question Number is found to be "1", which allows the corresponding answer to be read from ANSARRAY1.

If at Step 412, the answer is found not to be "NO" (i.e. found to be YES or NOT SURE), Step 413 will set the PRINT flag. Later, when the program reaches Step 415, the set PRINT flag will cause the test's name to be printed by Step 416.

If at step 412 the answer "NO", there is a jump to Step 414 so the PRINT flag will not be set. Step 414 checks to see if M=0, which would indicate that there are no more question address pointers to be read from field QUESADDS. If M≠0, there is a jump to Step 411 where the index variable L is incremented and the index variable M is decremented.

Thus, any of the question numbers associated with a test can, for a YES or NOT SURE answer, cause the PRINT flag to be set at Step 413. When Step 414 finds that M=0, the PRINT flag is checked by Step 415, and if it is set, the TESTNAME is printed at Step 416. Then the program proceeds to Step 417 where the indexing integer N is incremented to proceed to the next test.

If none of the answers to the questions associated with the Nth Test has set the PRINT flag, at Step 415 the answer is "NO", and there is a jump to Step 417 where N is incremented to the next test in TESTINFO.

As mentioned above, as N is incremented, eventually the final or dummy test whose TESTNUMBER is "0" is reached. Then the result of Step 404 is a YES, and Step 405 prints a heading "PATIENT REPORTS RECENTLY HAVING THE FOLLOWING TESTS:". To determine what comments should be printed about past tests, reference is then made to the array STATEMENTS. This array gives pointers to any YES Comment String, NO Comment String, or NOT SURE Comment String which follows a Lab Test Question. The patient's stored answers determine which of these three comment strings is printed.

For example, question 67 asks if the patient has had a blood test in the last six months. The YES Comment String to be printed at Step 406 is "PATIENT HAS HAD A BLOOD TEST IN THE LAST 6 MONTHS.", and the NO and NOT SURE Comment Strings are "PATIENT MAY NOT HAVE HAD A BLOOD TEST IN THE LAST 6 MONTHS."

After these lab test comments are printed at the end of the doctor's report, Step 406A prints Comment Strings about the patient that will be helpful to the doctor's selection of tests. For example, if the patient answered "YES" that he or she wears dentures, a YES Comment String "PATIENT WEARS DENTURES" will be printed. A table of which questions have a printable associated YES Comment String or NO Comment String is stored in an array STATEMENTS.

After these special comments are printed, Step 407 executes a Return From Subroutine f. Printing Questions & Answers If a set of valid answers has been taken from the patient, from the main menu (FIG. 3B) the medical staffer can also choose to print out the questions together with the patient's answers, including follow-up questions with blanks for handwritten answers. As in the case of the Doctor's Report, test selector 20 is connected to a standard serial printer 42 as shown in FIG. 2 via printer port 21e.

To print the questions and answers, at the main menu (FIG. 3B, FIG. 7, Step 206) the staffer selects command 3. Because Steps 207 and 215 are "NO" and Step 220 is "YES", next Step 221 checks to see if the VALIDDATA flag is set. If it is, there is a valid set of data to print, and the subroutine PRINT Q&A RESPONSES is called at Step 222.

Figure 11:
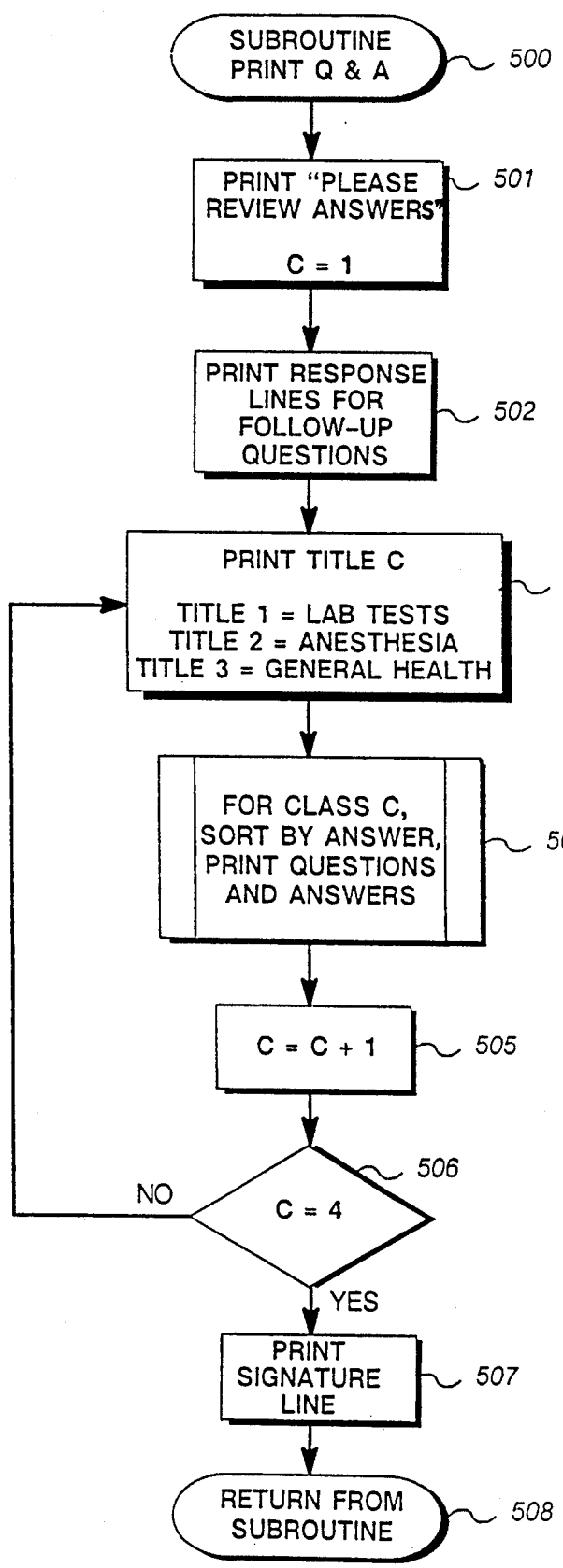
FIG. 11 is a flowchart of the "PrintQ&A" subroutine of FIG. 7, which prints a list of questions presented and the patient's answers, sorted by answer and question type.

The PRINT Q&A RESPONSES subroutine is shown in more detail in FIG. 11. The subroutine begins at Step 500 and moves to Step 501, where a header for the report is printed (see Appendix II). A line is printed that instructs the patient, "PLEASE REVIEW YOUR ANSWERS". An indexing variable C is set equal to 1.

Next, any Follow-Up Questions associated with questions to which the patient has answered YES ar printed with blanks to be completed by the patient. This is done in a manner similar to that described for Step 401 of the subroutine PRINT DOCREPORT of FIG. 10. The Follow-Up Question is stored in memory in the Question Structure after the question to which it is associated. The array called SPCQST tells STEP 502 which YES/NO questions have associated Follow-Up Questions, which answers (YES, NO, NOT SURE) should cause a Follow-Up Question to be printed, and the address of each Follow-Up Question.

The questions are divided into groups separated by titles printed at Step 503. The title printed at Step 503 depends on the current value of the variable C: 1=LAB TESTS, 2=ANESTHESIA, 3=GENERAL HEALTH. For each value of C (1, 2, 3), Step 504 calls the subroutine SORT AND PRINT QUESTIONS AND ANSWERS of FIG. 12 to print the questions and answers having the Question Class which corresponds to the current title Within a title, the order of printing is questions answered "YES" questions answered "NOT SURE", and questions answered "NO". For example, when C=1, calling the subroutine of FIG. 12 will only cause the questions and answers related to LAB TESTS to be sorted out and printed in this order.

Then at Step 505, the variable C is incremented so, questions and answers under the next title can be printed Assuming that there are just three titles, a check is made at Step 506 to see if C=4. If it does not, there is a jump back to Step 503 for the next title. But if C=4 at Step 507, there are no more titles and a signature line for the patient is printed under the words "THE ABOVE ANSWERS ARE CORRECT AS TYPED". After the signature line is printed, there is a Return From Subroutine at Step 508.

Figure 12:
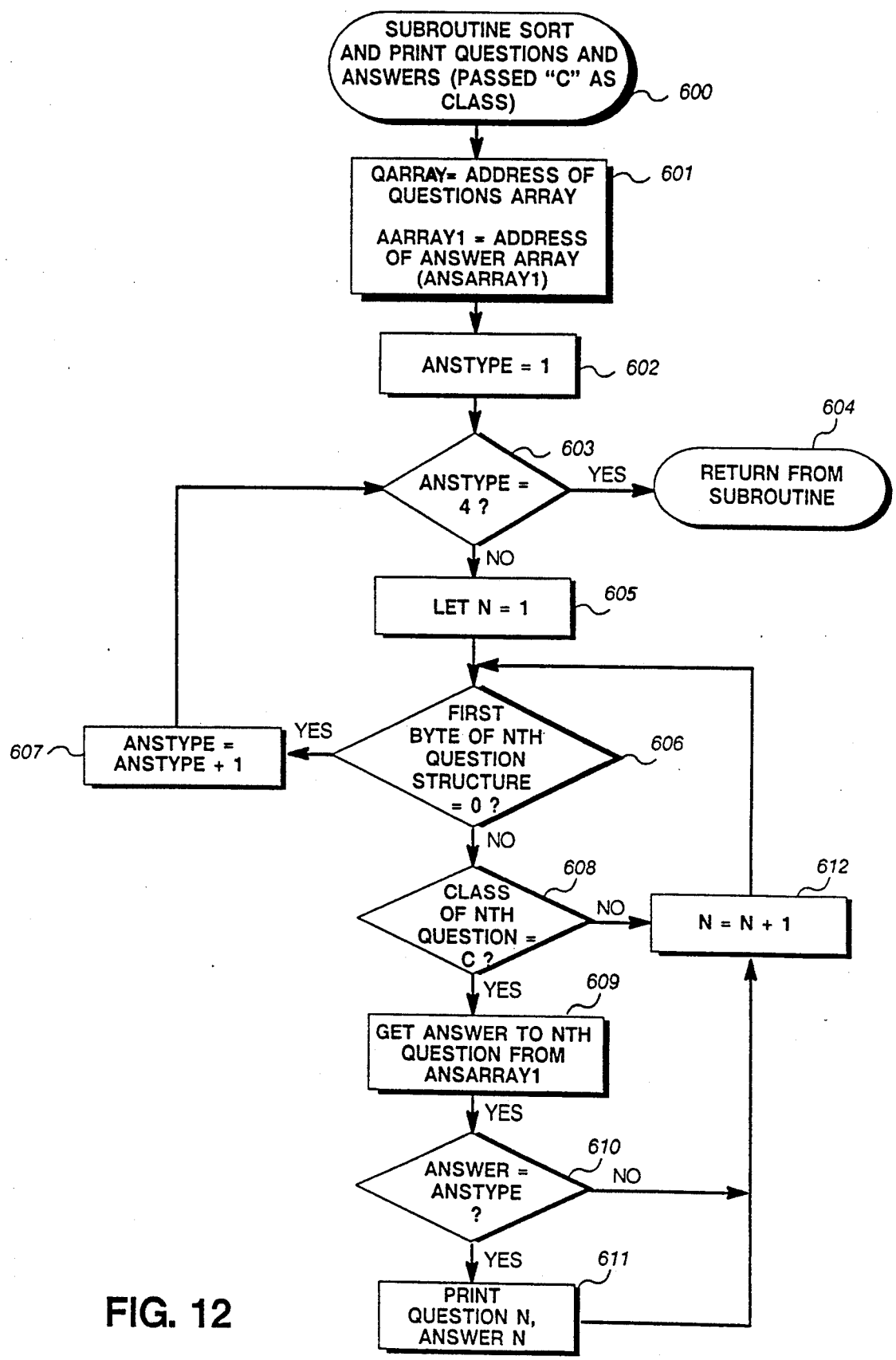
FIG. 12; is a flowchart of the "SORT AND PRINT QUESTIONS AND ANSWERS" subroutine used in the PrintQ&A subroutine of FIG. 11.

The SORT AND PRINT QUESTIONS AND ANSWERS subroutine is shown in more detail in FIG. 12. The routine begins at Step 600 with some given value of C (1, 2, or 3) from the calling subroutine of FIG. 11. At Step 601 the respective addresses of the QUESTIONS ARRAY and first ANSWER ARRAY are noted. At Step 602 an indexing variable ANSTYPE is initially set to 1.

The variable ANSTYPE has the following meanings 1=YES answer, 2=NOT SURE answer, 3=NO answer, 4=NOTASKD (end of printed answers). Therefore, at Step 603 a check is made to see if the indexing variable ANSTYPE equals four. If it does, there is a Return From Subroutine at Step 604.

However, initially ANSTYPE is one because of Step 602, and the program proceeds to Step 605 where an indexing integer N is set to 1. Then at Step 606, the first byte of the Nth Question Structure stored in the questions array QARRAY is read. If it equals zero, the dummy Question Structure has been reached that indicates there are no more questions to process.

However, usually the first byte is not zero, in which case Step 608 compares the Question Class of the Nth Question Structure with the value of C input to the subroutine. If the Question Class does not match C, a jump is made to Step 612, where N is incremented and a jump made back to Step 606 to check the first byte of the next Question Structure.

When the Question Class of the Nth Question Structure matches the value of C at Step 608, the corresponding answer is obtained from answer array ANSARRAY1 by Step 609. If the answer matches the current value of ANSTYPE, the Question and its corresponding Answer are printed at Step 611. Otherwise, the Question and Answer are skipped by jumping to Step 612, where the variable N is incremented Then there is a return to Step 606 to read the first byte of the next question structure.

For each value of ANSTYPE, eventually N is incremented at Step 612 until the dummy Question Structure is reached, causing a "YES" at Step 606. Then Step 607 increments ANSTYPE to the next type of answer. Eventually, Step 607 causes ANSTYPE to equal four, which is detected by Step 603 to cause a Return From Subroutine at Step 604 as mentioned above.

Thus, for a given category of question C, the subroutine of FIG. 12 first prints all the questions answered "YES", then all those answered "NOT SURE", and then all those answered "NO". Within a category, the answer given to a question determines its order in the printout.

In the first embodiment of the invention so far described, the subroutine ASK QUESTIONS, STORE ANSWERS of FIG. 9 processes each question in sequence (FIG. 13C), but if the WOMANFLAG is CLEAR certain questions only for females are not displayed (FIG. 9, Step 311) and automatically answered "NOTASKD" (not asked) by Step 318 As shown in FIG. 13A, the flag check FCh causes question $Q_i$ to be skipped when the WOMANFLAG is CLEAR and instead processing proceeds to question $Q_{i+1}$.

For a male patient, if the program has to be backed up from question $Q_{i+1}$, logic is built in so that backup key 37 skips question $Q_i$ and returns to previous question $Q_{i-1}$, here assumed to be a general question for both men and women. Thus, this simple automatic skipping of certain questions irrelevant to the particular patient does not greatly complicate use of backup key 37.

In the subroutine PRINT DOCREPORT, which prints a report to the doctor, questions whose answer is "NO" or "NOTASKD" do not cause the associated test to be printed (Step 412). The subroutine SORT AND PRINT QUESTIONS AND ANSWERS of FIG. 12 treats questions having the answer "NOTASKD" as a forth type whose printing is skipped by the action of Step 603.

A second embodiment of the invention allows for more general branching to further questions in accordance with the patient's answers and provides a means for storing the return path needed to support backup key 37. A source code listing of the control program for the second embodiment is attached as Appendix IV.

As shown in FIG. 13D, in the second embodiment the next step of the control program after displaying question $Q_i$ depends on whether the answer to question $Q_i$ is YES (Y) or NO (N). In the general case, as shown in FIG. 13B, we must also allow for the alternative paths to converge at certain questions, such as $Q_{13}$ and $Q_{18}$. To move backwards to previous questions along the correct alternative paths requires special support for backup key 37.

As shown even more generally in FIG. 13E, each question $Q_i$ can be followed by a branch to one of three different paths Y, N, NS, corresponding to YES, NO, and NOT SURE. FIG. 13F shows the tree-like structure of the possible paths of the program when the next question to be asked depends on whether the answer is YES, NO, or NOT SURE.

To enable such branching, the previously mentioned Question Structure stored for each question in the QUESTIONS array is augmented as follows:

<Question Number> <Assoc Flag> <Question Class>
<Text String>
<Branchflag> <Next/Yes Question Pointer>
[<No Question Pointer>]

The additional parts of the Question Structure which enable branching are a BRANCHFLAG, a NEXT/YES QUESTION POINTER and a NO QUESTION POINTER. If a particular question does not need branching, such as question $Q_i$ of FIG. 13C, the BRANCHFLAG is CLEAR, the NEXT/YES QUESTION POINTER is used as a pointer to the next question $Q_{i+1}$, and the NO QUESTION POINTER is not present.

A question leading to a YES or NO alternative (see FIG. 13D) has its BRANCHFLAG SET. The NEXT/YES QUESTION POINTER points to the next question that should follow a "YES", and the No Pointer points to the next question that should follow a "NO". For purposes of branching, the test selector can be designed to always treat an answer of "NOT SURE" as either a "YES" or a "NO". Alternatively, the test selector's Question Structure can be further augmented to add a separate pointer [<Not Sure>] for a third alternative as shown in FIG. 13E.

Figure 14:
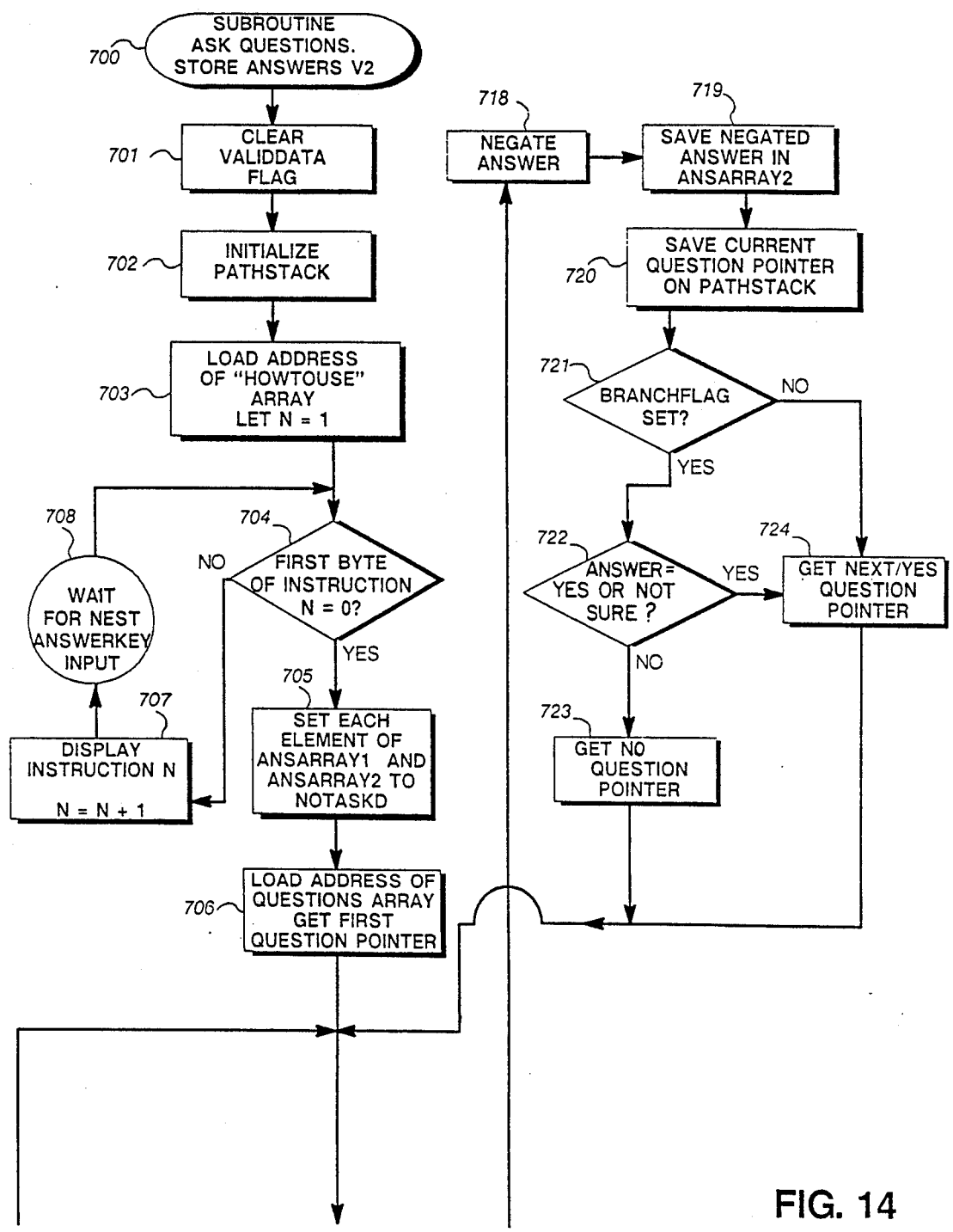
FIG. 14 is a flowchart of a second embodiment of the "Ask Questions, Store Answers" subroutine of FIG. 7.
Figure 14:
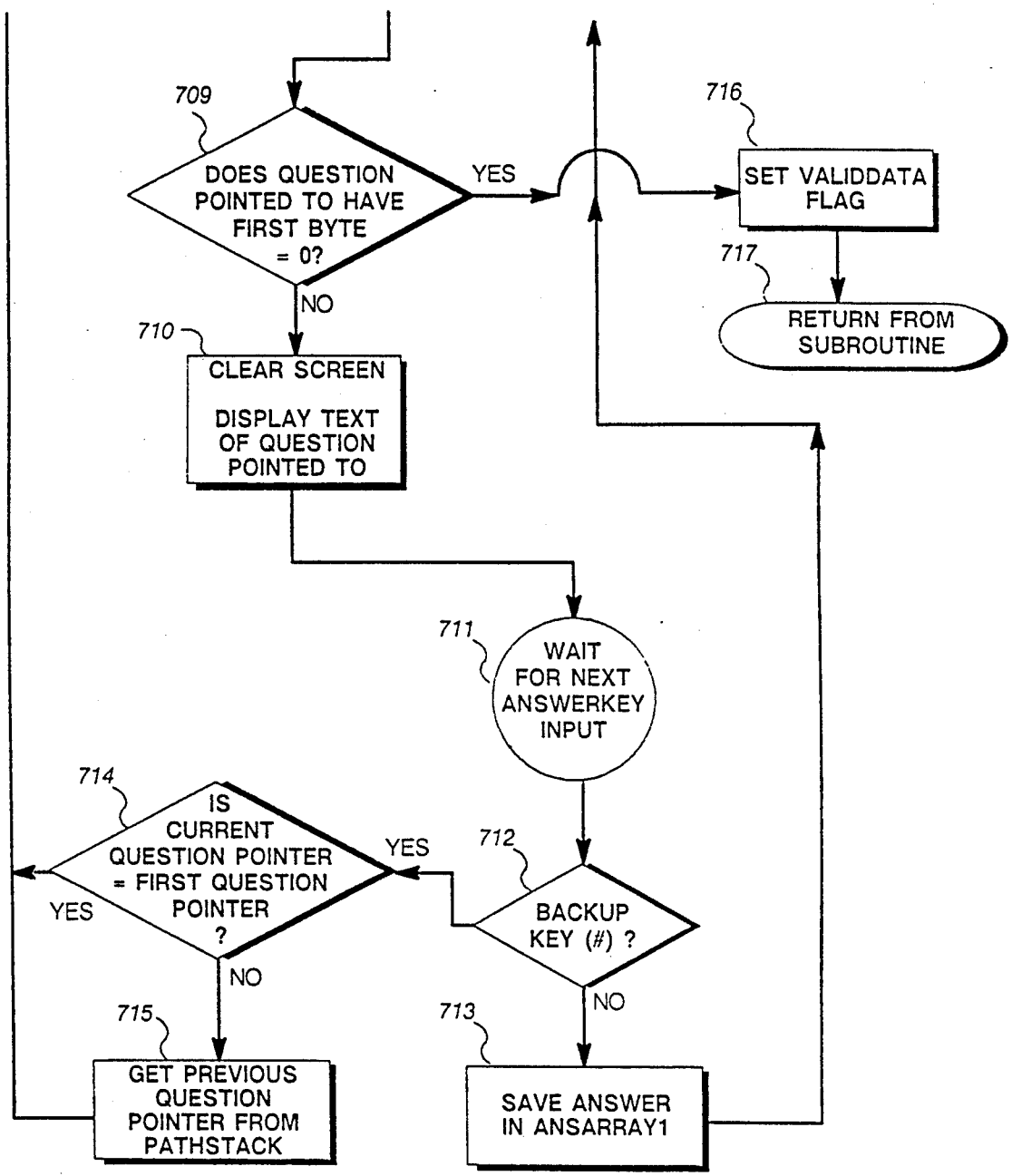

For example, to enable branching which treats an answer of "NOT SURE" like a "YES", FIG. 14 shows a subroutine ASK QUESTIONS, STORE ANSWERS V2 to be substituted for the first embodiment's ASK QUESTIONS, STORE ANSWERS subroutine of FIG. 9. Beginning at Step 700, the VALIDDATA flag is cleared at Step 701 and a portion of RAM memory 142 (FIG. 5) is initialized as a first-in-last-out stack called PATHSTACK for question address pointers Then the address of the array "HOWTOUSE" is loaded at Step 703, and an index integer N set initially to 1.

Step 704 tests the first byte of Instruction N for 0h. Since the Instruction screens have some other hexadecimal number in the first byte, a jump is made to Step 707, which causes Instruction screen N to be displayed and N incremented. Then Step 708 causes a pause until the next answer keypad input, after which there is a jump to Step 704 to check the first byte of the next Instruction Screen. Finally, a first byte of 0h in the last (dummy) screen is detected, indicating that all the Instruction Screens have appeared to the patient on display 22. The program proceeds to Step 705 where each element of the two answer arrays ANSARRAY1 and ANSARRAY2 is initialized to "NOTASKD" (not asked).

The address of the QUESTIONS array is loaded at Step 706, and the first question pointer used to obtain the address of the Question Structure for the first question. The first byte of this Question Structure is examined at Step 709 to see if it is 0. Usually it is not, so the program proceeds to Step 710 which clears the screen and displays the text of the question pointed to. Then Step 711 waits for an answer to be input at the patient's keyboard.

Assuming at Step 712 that the backup key # has not been pressed, Step 713 saves the patient's YES, NO, or NOT SURE answer as distinguishable binary codes in an corresponding entry of an answer array ANSARRAY1. Then Step 718 determines the two's complement of the answer code, and Step 719 saves this in a second answer array ANSARRAY2.

If instead Step 712 finds that the backup key on the control pad was pressed, Step 714 determines if the current question pointer is that pointing to the first question. If it is, there is no backup because we are already at Question 1. But if Step 714 determines that the question currently pointed to is greater than 1, Step 715 pops the pointer for the previously asked question off the PATHSTACK. Then a jump is made back to Step 709 to process the previously asked question.

After Step 719 has saved the two's complement of an answer in ANSARRAY2, Step 720 pushes the current question pointer onto the PATHSTACK. If Step 721 finds that the BRANCHFLAG is SET, Step 722 determines if the patient's answer is NO. If it is, Step 723 uses the NO QUESTION POINTER of the current question for the address of the next question to be asked, and a branch is made back to Step 709.

If instead the patient's answer is "YES" or "NOT SURE", Step 724 uses the NEXT/YES QUESTION POINTER of the current question for the address of the next question, followed by a branch back to Step 709.

If Step 721 finds that the BRANCHFLAG is CLEAR, the answer to the current question does not cause branching into alternate paths NEXT/YES QUESTION POINTER of the current question for the address of the next question to be asked, and there is a branch back to Step 709.

The ASK QUESTIONS, STORE ANSWERS V2 routine ends when at Step 709 a question is encountered whose question number is 0. A branch is then made to Step 716 to set the VALIDDATA flag, after which Step 717 executes a Return From Subroutine.

In this manner, the PATHSTACK, BRANCHFLAG, NEXT/YES QUESTION POINTER, and NO QUESTION POINTER of the second embodiment enable more general branching to further questions in accordance with the patient's answers, without sacrificing the function of backup key 37. This enables the questions asked to be highly relevant and detailed with respect to the patient's age, sex, history and condition, and facilitates the asking of follow-up questions. Since the answer arrays are initialized to "NOTASKED", it is easy for the subroutines DOCREPORT and PRINTQ&A to ignore unasked questions.

The invention provides a compact, portable automatic test selector for taking patient histories which is easily used, even by bed-ridden patients, and especially adapted for the selection of medical and pre-operative tests. The test selector is easily connected to a printer to print out a report to the doctor of recommended medical and/or pre-operative tests and a sorted list of the questions and the patient's answers. It can also be attached to a suitable computerized work station. In addition, there is provision for the patient to review and supplement the answers.

While the principles of the invention have been described above in connection with specific apparatus and applications, it is to be understood that this description is intended only by way of example and not as a limitation on the scope of the invention. Therefore, the following claims are to be construed to cover all equivalent structures.

LIST OF APPENDICES

I. Appendix I—Report to Doctor
II. Appendix II—Printout of Questions and Answers
III. Appendix III—Source Code for Embodiment 1
IV. Appendix IV—Source Code for Embodiment 2

APPENDIX I

*Ault Development Corp. 1985,*

PATIENT- NAME:                                                      DATE:

BIRTHDATE:

PERSON ADMINISTERING:

PHYSICIAN:

When did you previously have anesthesia? _____

What are you allergic too? _____

Based on the response of the patient to the questions, the following laboratory tests would be indicated considering the likelihood of the test finding disease or optimizing patient care, versus the result of that test leading to false positive tests and subsequent hazard to the patient. This guideline is valid to JUNE 30, 1988, and is based on literature and reviews published by Roizen in Miller's ANESTHESIA, 1986 edition; by Robins and Rose in MEDICAL CLINICS OF NORTH AMERICA, 1979 and 1986; by Blepyetal in LANNCET, January 1986; by numerous authors in ANNALS OF INTERNAL MEDICINE (May 1985 through December 1986). Similar guidelines for radiology studies have been endorsed by an FDA panel (1984), the American College of Surgeons, and American College of Physicians (not an all inclusive list). Guidelines for all tests are similar to those presented at an NIH consensus panel on Anesthesia for Dental Patients endorsed in the Blue Cross-Blue Shield Medical Necessity Guidelines by the American College of Physicians (and published in ANNALS OF INTERNAL MEDICINE), and by the American Society of Anesthesiology.

These responses to the questionnaire are to be an aid to the physician and should be supplemented and should NOT be considered as a substitute to the physician's history, physical, and any test(s) the physician deem(s) clinically indicated. Such routine screening tests as stool, Pap smears, guiacorhemocult, etcetera are not suggested as indicated. Such may be indicated based on the physician's judgment of them; the indicated laboratory tests below are only tests thought appropriate for the perioperative care of the patient.

INDICATED LABORATORY TESTS

CBC
CALCIUM
MAGNESIUM
PHOSPHORUS
·ALBUMIN
CHEST XRAY PA/LAT
EKG

THE PATIENT REPORTS THAT HE/SHE HAS HAD THE FOLLOWING
TESTS RECENTLY:

Patient may not have had a blood test in the last 6 months.
Patient may not have had a chest X-RAY in the last 2 months.
Patient may not have had an EKG in the last 2 months.
Patients stool may not have been checked for blood in the last year.
Patient may not have had a pap smear in the last year.
Patient may not have had a mammogram in the last year.

© ARCH Development Corp. 1988.

APPENDIX II

PATIENT NAME:                                                              DATE:

BIRTHDATE:

PERSON ADMINISTERING:

PHYSICIAN:

******* LAB TEST QUESTIONS ******

Have you taken Asprin, Excedrin, Anacin,                                    YES
Bufferin, Alka Seltzer or any similar
medications in the last week?

| | |
|---|---|
| Have you lost more than 5% of your usual body weight in the last year? | YES |
| Do you suffer from shortness of breath, chest pain, emphysema, asthma, or bronchitis? | YES |
| Do you have muscle cramps or spasms in your legs more than three times per year? | YES |
| Are you older than 39? | YES |
| Do you currently take drugs to suppress your immune system such as cyclosporin, azathioprine, imuran, cyclophosphamide, or 6-mercaptopurine? | NO |
| Have you ever been treated for cancer with chemotherapy or x-ray radiation therapy? | NO |
| Do you have or have you had problems with your blood such as anemia, leukemia, or sickle cell disease? | NO |
| Have you ever had a bleeding problem or a blood clotting problem? | NO |
| Are your stools ever bloody or black and tarry? | NO |
| Have you vomited blood or material that looks like coffee grounds in the last 6 months? | NO |
| Did you receive a blood transfusion within the last six months? | NO |
| Did you receive a blood transfusion after 1979? | NO |
| Have you ever required a blood transfusion for excessive bleeding? | NO |
| Have you ever smoked half a pack or more cigarettes per day on a regular basis? | NO |
| Have you smoked half a pack or more cigarettes per day within the last two weeks? | NO |
| Have you quit smoking and continued without cigarettes for 4 weeks? | NO |
| Have you quit smoking and continued without cigarettes for 5 years? | NO |
| Do you cough regulary or frequently? | NO |
| Do you cough up sputum? | NO |
| In the last month have you noticed a change in the color or consistency of the sputum? | NO. |
| In the last 4 weeks have you had a fever, chills, cold, or flu? | NO |
| Have you ever had a heart attack or been treated for a possible heart attack? | NO |

| | |
|---|---|
| Do you have heart problems such as skipped heart beats, angina or chest pain? | NO |
| Do you currently take quinidine, inderal diltiazem, verapramil, nifedipine, nitroglycerine, or propranolol, digoxin lanoxin, digitoxin or digitalis? | NO |
| Do you currently take any medication for high blood pressure? | NO |
| Have you been told by your doctor to exercise and diet to control high blood pressure? | NO |
| Have you ever woken up at night and felt short of breath? | NO |
| Do you become short of breath after climbing one flight of stairs or after walking a short distance? | NO |
| Do you currently take water pills or diuretics? | NO |
| Do you currently take potassium pills or powder? | NO |
| Do you have any problems with your kidneys? | NO |
| Have you ever been told you have diabetes or sugar diabetes? | NO |
| Do you often wake up to urinate more than once a night? | NO |
| Do you currently take anti-coagulents or blood thinning medicine? | NO |
| Have you ever had prolonged or unusual bleeding from nosebleeds, tooth extractions, cuts or surgery? | NO |
| Do you bleed from your gums when you brush your teeth? | NO |
| Have you ever been diagnosed as having a serious bleeding problem? | NO |
| Has a family member or blood relative ever been diagnosed as having a serious bleeding disorder? | NO |
| Have you ever had kidney stones, kidney failure, dialysis, or infection of the kidney? | NO |
| Have you ever had hepatitis, yellow jaundice, liver disease or malaria? | NO |
| Have you ever been exposed to anyone with yellow jaundice or hepatitis? | NO |
| Have you ever been exposed to anyone with yellow jaundice or hepatitis within the last 6 months? | NO |
| Do you often drink more than three alcoholic drinks per day? (Three shots, three beers, or three glasses of wine?) | NO |

| | |
|---|---|
| Within the last 2 years have you taken, injected or smoked any non-prescription drugs such as cocaine, marijuana, LSD, herion, etc. | NO |
| Have you been exposed to the body secretions (blood, urine, saliva, etc.) of anyone likely to have the AIDS virus? | NO |
| Are you in a high risk group for AIDS? (Homosexual, Bisexual, had sex with a prostitute in the last 6 years or have Hemophelia.) | NO |
| Would you like to receive a test to find out if you have been exposed to the AIDS virus? | NO |
| Do you have any pain or discomfort with urination, or have you noticed any blood in your urine? | NO |
| Are you female? | NO |
| Do you have any reason to believe you are pregnant or that you may possably be pregnant? | NO |
| Are you going to have an operation? | NO |
| Are you older than 59? | NO |
| Have you had blood tests in the last 6 months? | NO |
| Have you had a chest X-ray in the last 2 months? | NO |
| Have you had an EKG in the last 2 months? | NO |
| Has your stool been checked for blood in the last year? | NO |
| Have you had a pap smear in the last year? | NO |
| Have you had a mammogram (X-Rays of your breasts) in the last year? | NO |

****** ANETHESIA QUESTIONS ******

| | |
|---|---|
| Do you have any allergies? | YES |
| Have you had anesthesia in the past? | YES |
| Do you wear dentures, partial or a bridge? | NO |
| Do you have any capped teeth? | NO |
| Do you wear contact lenses? | NO |
| Do you have any teeth loose? | NO |
| Have you or any other member of your family or blood relatives had any problems with anesthesia in the past? | NO |

**** GENERAL HEALTH QUESTIONS ***

| | |
|---|---|
| Have you engaged in sex (intercourse) within the last 2 weeks? | YES |
| Is your level of sexual desire and activity normal for you? | YES |
| Has your appetite for food changed in the last year? | NO |
| Are you eating the same foods as you were a year ago? | NO |
| Are you able to walk up stairs at the same rate you could 5 years ago? | NO |
| Have your bowel or bladder functions changed in the last year? | NO |
| Have you been diagnosed as having a hiatus hernia? | NO |
| Have you had heartburn within the last month? | NO |
| Have you had heartburn within the last month? | NO |
| Do you take Cimetidine, Ranitidine Tagamet, or Zantac? | NO |

APPENDIX III
© ARCH Development Corp. 1988.

```
        TITLE   'MAIN'
************************************************************************
*
* THIS PROGRAM WILL SCAN THE KEY BOARD AND THEN OUTPUT TO THE DISPLAY
*
*
        NAME    MAIN
        LIST    1
*
        XDEF    MAIN
*
        XREF    CLR.SC,ASKQ,STRDSP,GETANS,GETK16,KY.HAN
        XREF    HEADER,ENTER,QVALID,RPTPRT,PRTQST,OUTCHR
*
        PSCT
*
ALT1:   FCC     /$            ENTER ACCESS CODE$/
        FCC     /                    /
        FCB     0
ALT2:   FCC     / 1) ASK QUESTIONS    4) SET TIME$/
        FCC     / 2) PRINT RESULTS    5) RUN DIAGNOSTICS$/
        FCC     / 3) PRINT RESPONSES  ->> /
        FCB     0
MES1:   FCC     /$  -- FUNCTION NOT YET IMPLEMENTED --$/
        FCC     /$      ENTER ANY KEY TO CONTINUE/
        FCB     0
MES2:   FCC     /$  -- PRINTING ANALYSIS RESULTS --/
        FCB     0
MES3:   FCC     /$  -- PRINTING PATIENT RESPONSES --/
        FCB     0
MES4:   FCC     /    THIS COMPLETES THE QUESTIONAIRE.$/
        FCC     /         THANK YOU FOR YOUR TIME$$/
        FCC     /  PLEASE RETURN THIS UNIT FOR ANALYSIS/
```

```
         FCB   0
MES5:    FCC   /$QUESTIONARE COMPLETED ENTER ACCESS CODE$/
         FCC   /                        /
         FCB   0
ERROR1:  FCC   /$    ERROR: THERE IS NO DATA TO PRINT.$/
         FCC   /$         ENTER ANY KEY TO CONTINUE/
         FCB   0
ERROR2:  FCC   /$    ERROR: INVALID ACCESS CODE.$/
         FCC   /$         ENTER ANY KEY TO CONTINUE/
         FCB   0
ERROR3:  FCC   /$    ERROR: INVALID COMMAND.$/
         FCC   /$         ENTER ANY KEY TO CONTINUE/
         FCB   0
*
MAIN:    CLR A
         STA A  QVALID
*        JSR    GETK16
*        BRA    MAIN
*
AGAIN:   JSR    CLR.SC
         LDX    #ALT1          *Prompt for access code
         JSR    STRDSP
*
         LDA B  #2             *Echo X for password entry
         STA B  ECOFLG
*
         JSR    GETVAL         *Get Integer input (ACC-X)
         CPX    #9360          *Check against password
         BEQ    OPTION         *Valid display options
*
         JSR    CLR.SC         *Invalid display error message
         LDX    #ERROR2
         JSR    STRDSP
         JSR    DBKEY
         BRA    AGAIN
*
OPTION:  JSR    CLR.SC         *Display user options
         LDX    #ALT2
         JSR    STRDSP
         LDA A  #1
         STA A  ECOFLG         *Enable echo.
         JSR    GETVAL         *Read option (ACC-X)
         CPX    #1
         BEQ    OPT1           *ASK QUESTIONS
         CPX    #2
         BEQ    OPT2           *PRINT REPORT
         CPX    #3
         BEQ    OPT3           *PRINT PATIENT RESPONSES
         CPX    #4
         BNE    OP5            *SET TIME/DATE
         JMP    OPT4
OP5:     CPX    #5
         BNE    OPE            *RUN DIAGNOSTICS
         JMP    OPT5
*
OPE:     LDX    #ERROR3        *Invalid command
         JSR    CLR.SC
         JSR    STRDSP
         JSR    DBKEY
         BRA    OPTION
*
OPT1:    JSR    ASKQ
         JSR    CLR.SC
         LDX    #MES4
         JSR    STRDSP
         JSR    GETANS
*
AG1:     JSR    CLR.SC
         LDX    #MES5          *Prompt for access code
         JSR    STRDSP
*
```

```
          LDA B    #2              *Echo X for password entry
          STA B    ECOFLG
*
          JSR      GETVAL             *Get Integer input (ACC-X)
          CPX      #9360           *Check against password
          BEQ      OPTION             *Valid display options
*
          JSR      CLR.SC             *Invalid display error message
          LDX      #ERROR2
          JSR      STRDSP
          JSR      DBKEY
          BRA      AG1
*
OPT2:     LDA A    QVALID             *Check if valid patient data
          CMP A    #44H
          BNE      NODATA             *Invalid print error message
          JSR      CLR.SC          *Clear the screen
          LDX      #MES2           *Print current operation message
          JSR      STRDSP
          JSR      RPTPRT
          JMP      OPTION
*
OPT3:     LDA A    QVALID             *Check if valid patient data
          CMP A    #44H
          BNE      NODATA             *Invalid print error message
          JSR      CLR.SC          *Clear the screen
          LDX      #MES3           *Print current operation message
          JSR      STRDSP
          JSR      HEADER
          JSR      PRTQST
          JMP      OPTION
*
NODATA:   JSR      CLR.SC             *Print invalid data mesage
          LDX      #ERROR1
          JSR      STRDSP
          JSR      DBKEY
          JMP      OPTION
*
OPT4:     JSR      CLR.SC             *NOT IMPLEMENTED
          LDX      #MES1
          JSR      STRDSP
          JSR      DBKEY
          JMP      OPTION
*
OPT5:     JSR      CLR.SC             *NOT IMPLEMENTED
          LDX      #MES1
          JSR      STRDSP
          JSR      DBKEY
          JMP      OPTION
*
*
          DSCT
*
NUMBER:   RMB      2
NVAL1:    RMB      1
NVAL2:    RMB      1
NVAL3:    RMB      1
ECOFLG:   RMB      1
*
* This routine accepts numeric input and will echo the input on the screen
* if the echo flag is set. The input is converted to an integer and returned
* in the INDEX register.
*
          PSCT
*
GETVAL:   PSH A
          PSH B
          LDD      #0
          STD      NUMBER          *Clear the integer accumulator
          STD      NVAL1
*
```

```
NXTNUM: JSR     DBKEY           *Get input
        CMP B   ENTER           *Input terminated?
        BEQ     FIN
        SUB B   #48             *Convert from ASCI to Integer
        CMP B   #0              *Make sure input is a valid number
        BLT     NXTNUM
        CMP B   #9
        BGT     NXTNUM
*
        STA B   NVAL2           *Save the number
        TST     ECOFLG          *Echo flag on?
        BEQ     NOECO
        ADD B   #48             *Yes, convert to ASCI and display it
        LDA A   #2
        CMP A   ECOFLG          *Special password echo
        BNE     OV1
        LDA B   #'X'
*
OV1:    JSR     OUTCHR          *Echo input
*
NOECO:  LDD     NUMBER          *Get the previous value
        ASLD                    *Multiply by 10
        ASLD
        ADDD    NUMBER
        ASLD
        ADDD    NVAL1           *Add in the new value (16 bit)
        STD     NUMBER          *Save new sum
        BRA     NXTNUM          *Get next character
*
FIN:    LDX     NUMBER          *Load result in ACC-X
        PUL B
        PUL A
        RTS
*
* This routine is used to debounce the user input. The value will not be
* returned until the user releases the key.
*
DBKEY:  JSR     KY.HAN          *Get input
        TST B                   *Wait for some input > 0
        BEQ     DBKEY
        STA B   NVAL3           *Save the key
*
DEB:    JSR     KY.HAN          *Debounce by waiting for change
        CMP B   NVAL3
        BEQ     DEB
*
        LDA B   NVAL3
        RTS
*
        END NAME    ASKQ
*
        LIST    1               *Use the 6801 Instruction set
*
        XDEF    ASKQ,STRDSP,GETANS,ANS1,ANS2,QAPTR
        XDEF    YES,NO,IDNO,ENTER,NOANS,QVALID
*
* This routine is called to ask the questions and save the answers in
* the two answer arrays (normal and complemented). A valid flag is used
* to ensure that all of the questions were answered and that the routine
* was terminated normally.
*
*List the externally used functions
*
        XREF CLR.SC,KY.HAN,OUTCHR
*
*List the externally defined memmory locations
*
        XREF    IARRAY,QARRAY
*
```

```
            DSCT
QVALID      RMB     1
ANS1        RMB     76
ANS2        RMB     76
QAPTR       RMB     2
WOMAN       RMB     1
*
            PSCT
*
ASKQ:       PSH A                       *Save the A, B and X registers
            PSH B
            PSHX
*
* This loop will display instruction messages in the address array
* IARRAY until the first character to display is 0.
*
            LDX     #IARRAY             *Get address of instruction array
IMSG:       JSR     CLR.SC              *Clear the display
            PSHX
            LDX     0,X                 *Get address of string to display
            LDA B   0,X                 *First byte = 0? Done.
            BEQ     IDONE
            JSR     STRDSP              *Display the message
            JSR     GETANS              *Wait for input
            PULX
            INX
            INX
            BRA     IMSG
*
IDONE:      PULX                        *Clean up the stack
*
            LDA A   #4
            STA A   QVALID              *Set first half of valid flag
*
            LDA A   #1
            STA A   WOMAN               *Set the woman flag
*
* This loop will display the questions and save the users answer in
* the two answer arrays. As above 0 is the terminator.
*
            LDX     #QARRAY             *Get question address array
NXTQ:       STX     QAPTR               *Save array address
            LDX     0,X                 *Get address of question
            LDA B   0,X                 *Read the question index (ACC-B)
            BEQ     DONE                *End of questions? Exit.
            INX                         *Advance to question flag
            TST     WOMAN               *Is the woman flag set
            BNE     ASKALL              *Yes, ask all questions
            LDA A   0,X                 *No, get question flag
            CMP A   #2                  *Is this a womans question
            BNE     ASKALL              *No, ask the question
            LDA A   NOANS               *Yes, set to NO ANSWER
            BRA     SKIPQ               *Do not ask the question
*
ASKALL:     INX                         *Set to address of question string
            INX
            JSR     CLR.SC              *Clear display screen
            JSR     STRDSP              *Display the question
            JSR     GETANS              *Get the users answer (Returned in ACC-A)
*
            CMP A   BKUP                *BACKUP command?
            BNE     SKIPQ
            LDX     QAPTR
            CMP B   #1                  *Are we at the first question?
            BEQ     NXTQ                *Yes, Ignore command
            DEX                         *Backup to previous question
            DEX
            BRA     NXTQ
*
SKIPQ:      LDX     #ANS1               *Load address of first answer array
            ABX                         *Add question offset (Offset is in ACC-A)
```

```
        STA A    0,X           *Save the answer
*
        CMP B    #54           *Is this the gender question
        BNE      NOTIT         *No? Branch
        CMP A    YES
        BEQ      NOTIT         *Already set
        CLR A
        STA A    WOMAN         *Clear the gender flag.
*
NOTIT:  NEG A                  *Complement the answer
        LDX      #ANS2         *Load address of second answer array
        ABX                    *Add question offset (Offset is in ACC-A)
        STA A    0,X           *Save the complemented answer
*
        LDX      QAPTR         *Pop the question array address
        LDA B    #2
        ABX                    *Increment to next element
        BRA      NXTQ          *Ask next question
*
DONE:   LDA A    QVALID
        ADD A    #40H          *And in second half of valid flag
        STA A    QVALID        *Set the valid flag
        PULX                   *Restore the A, B, and X registers
        PUL B
        PUL A
        RTS
*
* This routine accepts a string pointed to by the X register. The
* string is output to the screen until an EOL is found. The
* "$" character is used to indicate CRLF and is replaced by those
* characters.
*
STRDSP: PSH B
        PSHX
STR1:   LDA B    0,X
        BEQ      OUT
        CMP B    #'$'
        BNE      OV1
        LDA B    #13
        JSR      OUTCHR
        LDA B    #10
        JSR      OUTCHR
        INX
        BRA      STR1
*
OV1:    PSHX
        CMP B    #$61          *Convert to upper case
        BLO      OV2
        CMP B    #$7A
        BHI      OV2
        SUB B    #$20
*
OV2:    JSR      OUTCHR
        PULX
        INX
        BRA      STR1
*
OUT:    PULX
        PUL B
        RTS
*
* This routine will accept input from the 4 keys and will echo
* the users response on the display. The response will not be
* returned until the user presses ENTER. The users response
* is returned in ACC A.
*
        DSCT
DVAL:   RMB      1
*
        PSCT
*
```

```
YESSTR: FCC     /   YES  /
        FCB     0
NOSTR:  FCC     /   NO   /
        FCB     0
IDNSTR: FCC     /NOT SURE/
        FCB     0
BKPSTR: FCC     / BACKUP /
        FCB     0
*
*****************
* NOTE: If the declarations below are changed make sure you change PRTQST.ASM
*****************
*
YES:    FCB     12
NO:     FCB     13
IDNO:   FCB     14
ENTER:  FCB     15
BKUP:   FCB     11
NOANS   FCB     20
*
*
GETANS: PSH B
        PSHX
        CLR A
        STA A   DVAL
*
GETCH:  JSR     KY.HAN                  *Get input in ACC-B
        TST B
        BEQ     GETCH
        TBA
        CMP A   DVAL                    *Same key (debounce)
        BEQ     GETCH                   *Yes ignore the input
        CMP A   YES                     *YES Key?
        BEQ     YESHAN
        CMP A   NO                      *NO Key?
        BEQ     NOHAN
        CMP A   IDNO                    *NOT SURE Key?
        BEQ     IDNHAN
        CMP A   BKUP                    *BACKUP key?
        BEQ     BUPHAN
        CMP A   ENTER                   *ENTER or NEXT QUESTION Key?
        BEQ     ENTHAN
        BRA     GETCH
*
YESHAN: LDX     #YESSTR                 *Display YES
        BRA     DISP
*
NOHAN:  LDX     #NOSTR                  *Display NO
        BRA     DISP
*
IDNHAN: LDX     #IDNSTR                 *Display NOT SURE
        BRA     DISP
*
BUPHAN: LDX     #BKPSTR                 *Display BACKUP
*
DISP:   STA A   DVAL                    *Save input
        JSR     POSCRS                  *Position the cursor
        JSR     STRDSP                  *Display the key stroke
        BRA     GETCH
*
ENTHAN: TST     DVAL                    *Check for valid input
        BEQ     GETCH                   *NO, Ignore input
*
        LDA A   DVAL                    *YES, Return input in ACC-A
        PULX
        PUL B
        RTS
*
* This routine positions the cursor to line 4 column 30
*
POSREP  FCB     27,61,35,64,0
```

```
*
POSCRS: PSHX
        LDX     #POSREP
        JSR     STRDSP
        PULX
        RTS
*
        END

NAME    HEADER
*
        LIST    1
*
        XDEF    HEADER,DISCLM,SPCHN1,SPCHN2
        XREF    PRTCHR,PRTSTR,ANS1,NO,YES,IDNO,NOANS
        XREF    W55,W57
        XREF    W62,W63,W64,W67,W68,W69
        XREF    Q58,Q59
        XREF    Q60,Q61,Q62,Q63,Q64,Q67,Q68,Q69
        XREF    Q70,Q71,Q72,Q73,Q74,Q75
        XREF    W58Y,W59Y
        XREF    W60Y,W61Y,W67Y,W67N,W68Y,W68N,W69Y,W69N
        XREF    W70Y,W70N,W71Y,W71N,W72Y,W72N,W73Y,W74Y,W75Y

*
        PSCT
*
FF:     FCB     12
LINE1:  FCC     /$$/
        FCC     /PATIENT NAME:                                          DATE:$$
LINE2:  FCC     /BIRTHDATE:$$/
LINE3:  FCC     /PERSON ADMINISTERING:$$/
LINE4:  FCC     /PHYSICIAN:$$$/
        FCB     0
*
*This routine prints the above header.
*
HEADER: PSHX
        PSH B
        LDA B   FF              *Send a form feed to align the paper
        JSR     PRTCHR
        LDX     #LINE1          *Print out the header
        JSR     PRTSTR
        PUL B
        PULX
        RTS
*
*
DISC:   FCC     /$ Based on the response of the patient to the questions, the
        FCC     /following  laboratory tests  would  be indicated considering
        FCC     /the likelihood  of  the  test finding  disease or  optimizing
        FCC     /patient  care, versus  the   result of  that test  leading to
        FCC     /false  positive tests and subsequent hazard  to the patient.
        FCC     /This guideline is  valid to  JUNE 30, 1988,  and is based on
        FCC     /literature  and  reviews published  by  Roizen  in  Miller's
        FCC     /ANESTHESIA,  1986 edition;  by Robins  and  Rose  in  MEDICAL
        FCC     /CLINICS OF NORTH AMERICA,  1979 and 1986;  by Blery et al in
        FCC     /LANCET,  January 1986;  by  numerous  authors  in ANNALS OF
        FCC     /INTERNAL MEDICINE (May 1985 through December 1986).  Similar
        FCC     /guidelines for radiology  studies have  been  endorsed by an
        FCC     /FDA panel  (1984),  the  American College  of  Surgeons, and
        FCC     /American College of Physicians  (not an all inclusive list).
        FCC     /Guidelines  for all  tests are similar to those presented at
        FCC     /an NIH consensus  panel  on  Anesthesia  for  Dental Patients
        FCC     /endorsed  in  the  Blue Cross-Blue Shield  Medical Necessity
        FCC     /Guidelines  by  the  American  College  of  Physicians  (and
        FCC     /published  in  ANNALS  OF  INTERNAL MEDICINE),  and  by  the
        FCC     /American Society of Anesthesiology.$$/
        FCC     /   These responses  to  the questionnaire are to be an aid to
        FCC     /the physician and should  be supplemented and should NOT  be
```

```
          FCC     /considered as a substitute to the physician's history,
          FCC     /physical, and any test(s) the physician deem(s) clinically
          FCC     /indicated. Such routine screening tests as stool guiac or
          FCC     /hemoccult, Pap smears, etcetera are not suggested as
          FCC     /indicated. Such may be indicated based on the physician's
          FCC     /judgement of them; the indicated laboratory tests below are
          FCC     /only tests thought appropriate for the perioperative care
          FCC     /of the patient.$$/
          FCB     0
*
DISCLM:   PSHX
          LDX     #DISC
          JSR     PRTSTR
          PULX
          RTS
*
CRLF:     FCC     /$/
          FCB     0
LINE:     FCC     /$_____$$/
          FCB     0
*
*
*This routine handles all of the special questions, those which require
*additional output. If the answer to the question is YES or NOT SURE the
*string associated with that question is printed. There are two entry
*points SPCHN1 is for printing the general health statements while SPCHN2
*is used to print the additional questions.
*
SPCHN1:   PSH A
          PSH B
          PSHX
          LDX     #STATMT
          CLR A
          STA A   LFLAG
          JMP     NXTTST
*
SPCHN2:   PSH A
          PSH B
          PSHX
          LDA A   #1                      *Enable the line flag
          STA A   LFLAG
*
          LDX     #CRLF
          JSR     PRTSTR
          LDX     #ANS1                   *Check answer 54
          LDA A   54,X
          CMP A   NO
          BNE     PRTIT
          LDA A   55,X                    *Check answer 55
          CMP A   NO
          BNE     SPOV1
          JMP     NXTO
SPOV1:    CMP A   NOANS
          BNE     PRTIT
          JMP     NXTO PRTIT:    LDX     #W55
          JSR     PRTSTR
          LDX     #LINE
          JSR     PRTSTR
          JMP     NXTO
*
*Process the pairs of values to check if any of the additional questions
*need to be printed. The array SPCQST contains a pointer to the question
*followed by a pointer to the additional question. If the answer to the
*question is a YES print the first additional question, if the answer is
*NO print the second string if the answer is NOT SURE print the third string.
*
          DSCT
*
```

```
LFLAG:    RMB       1
TSTPTR:   RMB       2
*
          PSCT
NPRT:     FCB       0
DONE      FCB       0
*
*Data Format:      <Question> <YES string> <NO string> <NOT SURE string>
*                                 *                          *
SPCQST:   FDB       Q63,W63,NPRT,W63,Q64,W64,NPRT,W64,Q62,W62,NPRT,W62
          FDB       Q67,W67,NPRT,W67,Q68,W68,NPRT,W67,Q69,W69,NPRT,W69
          FDB       DONE
*                                   *                          *
STATMT:   FDB       Q67,W67Y,W67N,W67N,Q68,W68Y,W68N,W68N,Q69,W69Y,W69N,W69N
          FDB       Q70,W70Y,W70N,W70N,Q71,W71Y,W71N,W71N,Q72,W72Y,W72N,W72N
          FDB       Q73,W73Y,NPRT,NPRT,Q74,W74Y,NPRT,NPRT,Q75,W75Y,NPRT,NPRT
          FDB       Q58,W58Y,NPRT,NPRT,Q59,W59Y,NPRT,NPRT,Q60,W60Y,NPRT,NPRT
          FDB       Q61,W61Y,NPRT,NPRT
          FDB       DONE
*
NXT0:     LDX       #SPCQST             *Get address of special questions
*
NXTTST:   STX       TSTPTR              *Save pointer to structure
          PSHX                          *Save copy of pointer on stack
          LDX       0,X                 *Get address of question
          LDA B     0,X                 *Load the offset index
          BEQ       OUT                 *Done? branch to end
          LDX       #ANS1               *Get address of answer array
          ABX                           *Add offset to base address
          LDA B     0,X                 *Get a copy of the answer
          CMP B     NOANS               *No answer don't print
          BEQ       NOPRNT
          CMP B     NO                  *If the answer is NO add 2
          BNE       OV1
          LDA B     #2
          PULX
          ABX
          PSHX
          BRA       OV2
*
OV1:      CMP B     IDNO                *If the answer is NOT SURE add 4
          BNE       OV2
          LDA B     #4
          PULX
          ABX
          PSHX
*
OV2:      PULX                          *Get pointer address
          PSHX
          INX                           *Add two to the pointer
          INX
          LDX       0,X                 *Load the address of the string
          LDA B     0,X                 *Print the string?
          BEQ       NOPRNT
          JSR       PRTSTR              *Print the string
          TST       LFLAG               *Line flag set? print the line.
          BEQ       NOPRNT
          LDX       #LINE
          JSR       PRTSTR
*
*Add 8 to the current pointer to advance to the next test trio and branch
*back to the top to process the pair.
*
NOPRNT:   PULX                          *Clean up stack
          LDA B     #8
          LDX       TSTPTR
          ABX                           *Add offset and get next structure
          BRA       NXTTST
*
OUT:      PULX                          *Clean up the stack
          PULX                          *Restore environment
```

```
        PUL B
        PUL A
        RTS
*
        END

NAME    PRTQST
*
        LIST    1                       *Use the 6801 Instruction set
*
        XDEF    PRTQST,CHKQST
*
*List the externally defined memmory locations
*
        XREF    QARRAY,QAPTR,ANS1,PRTCHR,PRTSTR,SPCHN2
*
        DSCT
*
CLASS:  RMB     1
ANSWR:  RMB     1
PFLAG:  RMB     1
CNTR:   RMB     1
*
        PSCT
*
*
* NOTE: If the declarations below are changed make sure you change ASKQ.ASM
*
YES:    FCB     12
EQYES:  EQU     12
*
NO:     FCB     13
EQNO    EQU     13
*
IDNO:   FCB     14
EQIDNO: EQU     14
*
NOTE1:  FCC     /$Please review your answers to make sure that /
        FCC     /they are correct.$$/
        FCB     0
NOTE2:  FCC     /$$The above answers are correct as typed$$$/
        FCC     /Signed _____/
        FCC     / Date _____$/
        FCB     0
TITLE1: FCC     /$$      ******** LAB TEST QUESTIONS ********$$/
        FCB     0
TITLE2: FCC     /$$      ******** ANETHESIA QUESTIONS ********$$/
        FCB     0
TITLE3: FCC     /$$      ****** GENERAL HEALTH QUESTIONS *****$$/
        FCB     0
*
CKARY1: FCB     1,EQYES,1,EQIDNO,1,EQNO,0       *Lab Test Questions
CKARY2: FCB     2,EQYES,2,EQIDNO,2,EQNO,0       *Anethesia Questions
CKARY3: FCB     3,EQYES,3,EQIDNO,3,EQNO,0       *General Health Questions
*
* This subroutine is used to print out the questions and the patients answers
* The report is sorted by class and answer. The sorting is controlled by the
* data array CHKARY above.
*
PRTQST: PSH A                           *Save environment
        PSH B
        PSHX
*
        LDX     #NOTE1                  *Print the review string
        JSR     PRTSTR
*
        JSR     SPCHN2                  *Print special questions
*
        LDX     #TITLE1                 *Print title for section
        JSR     PRTSTR
        LDX     #CKARY1                 *Get data array
        JSR     DOLIST                  *Sort and print Q&A
```

```
*
        LDX     #TITLE2                 *Print title for section
        JSR     PRTSTR
        LDX     #CKARY2                 *Get data array
        JSR     DOLIST                  *Sort and print Q&A
*
        LDX     #TITLE3                 *Print title for section
        JSR     PRTSTR
        LDX     #CKARY3                 *Get data array
        JSR     DOLIST                  *Sort and print Q&A
*
        LDX     #NOTE2                  *Print signature line
        JSR     PRTSTR PULX                            *Restore environment
        PUL B
        PUL A
        RTS
*
*
DOLIST: LDA A   0,X                     *Get the class
        BEQ     FIN                     *Data exhausted?
        INX
        LDA B   0,X                     *Get answer
        INX
        JSR     CHKQST                  *Check and print the Q&A
        BRA     DOLIST                  *Process next pair
*
FIN:    RTS
*
* This routine scans the question array searching for a particular class
* of question (ACC-A). If the class matches and the answer (ACC-B) is a
* match the question and answer are printed.
*
* THIS ROUTINE USES THE A AND B ACCUMULATORS:
*
*    ACC-A = CLASS
*    ACC-B = ANSWER
*
CHKQST: STA A   CLASS
        STA B   ANSWR
        PSHX
        LDX     #QARRAY
*
NXTONE: STX     QAPTR                   *Save the question arry pointer
        LDX     0,X                     *Get question pointer
        LDA B   0,X                     *Get the question offset
        BEQ     DONE                    *Finished?
        INX                             *Position to class
        INX
        LDA A   0,X                     *Load the question class
        CMP A   CLASS                   *Is it the right class
        BNE     NOTONE
        INX                             *Save string address on stack
        PSHX
        LDX     #ANS1                   *Get answer array
        ABX                             *Add in the offset
        LDA A   0,X                     *Read the patient answer
        CMP A   ANSWR                   *Does it match?
        BNE     NOTANS
        PULX                            *Yes, get address of string
        JSR     SPPRT                   *Print the question
        BRA     NOTONE
*
NOTANS: PULX                            *Clean up stack
*
NOTONE: LDX     #QAPTR                  *Get question pointer
        LDX     0,X
        LDA B   #2                      *Set to next question
        ABX
        BRA     NXTONE                  *Process next question
```

```
*
DONE:    PULX                          *Restore index register
         RTS
*
*
* *
YESSTR:  FCC     /YES/
         FCB     0
NOSTR:   FCC     /NO/
         FCB     0
IDNSTR:  FCC     /NOT SURE/
         FCB     0
ERROR:   FCC     /** ERROR **/
         FCB     0
*
* This is a special print routine used to print out the questions and
* associated answers. The first line is extended to include the patients
* answer. The address of the question string is expected in the INDEX
* register while the patients answer is in ACC-A
*
SPPRT:   PSH B
         CLR B
         STA B   PFLAG              *Clear the print flag
         STA B   CNTR                    *Clear the char counter
*
NXTCHR:  LDA B   0,X                *Get next character to print
         INX
         TST     PFLAG                   *If print flag set branch
         BNE     PRTCH
         INC     CNTR                    *Increment char counter
         CMP B   #'$'                    *Is char reserved character
         BEQ     PRTANS                  *Yes, print answer
         TST B                           *Is char EOS
         BNE     PRTCH                   *Yes, print answer
*
PRTANS:  INC     PFLAG                   *Set the print flag
         PSH B                           *Save Accumulators
         PSH A
         LDA A   #60                     *Calculate blank pads
         SUB A   CNTR
         LDA B   #' '
BLANK:   JSR     PRTCHR                  *Pad out to column 60
         DEC A
         BNE     BLANK
*
         PUL A                           *Get paitents answer
         PSHX
         CMP A   YES                     *YES, Print string
         BNE     OV1
         LDX     #YESSTR
         BRA     OV4
*
OV1:     CMP A   NO                      *NO, Print string
         BNE     OV2
         LDX     #NOSTR
         BRA     OV4
*
OV2:     CMP A   IDNO                    *NOT SURE, Print string
         BNE     OV3
         LDX     #IDNSTR
         BRA     OV4
*
OV3:     LDX     #ERROR                  *ERROR, Print string
OV4:     JSR     PRTSTR
         PULX
         PULB
*
PRTCH:   TST B                           *EOS?
         BEQ     STDONE                  *Yes, branch to exit
         CMP B   #'$'                    *Special character?
         BNE     OV5                     *No, branch and print
```

```
            LDA B   #13                     *CR
            JSR     PRTCHR
            LDA B   #10                     *LF
OV5:        JSR     PRTCHR                  *Print the character
            BRA     NXTCHR
*
STDONE:     LDA B   #13                     *CR
            JSR     PRTCHR
            LDA B   #10                     *LF
            JSR     PRTCHR
            LDA B   #10                     *LF
            JSR     PRTCHR                  *Print the character
*
            PUL B
            RTS
*
            END NAME    RPTPRT
            LIST    1
*
            XDEF    RPTPRT,PRTSTR
            XREF    HEADER,DISCLM,SPCHN1,SPCHN2
            XREF    TARRAY,NO,NOANS,ANS1
*
            DSCT
*
NXTTST:     RMB     2
OFFSET:     RMB     2
NUMIDX:     RMB     1
PFLAG:      RMB     1
*
            PSCT
*
TITLE1:     FCC     /$            INDICATED LABORATORY TESTS$$/
            FCB     0
TITLE2:     FCC     \$$THE PATIENT REPORTS THAT HE/SHE HAS HAD THE \
            FCC     /FOLLOWING $TESTS RECENTLY:$$/
            FCB     0
*
* This routine is responsible for printing the primary report generated by
* this device. A header is printed along with the special additional
* questions. This routine also determines if one of the tests is called
* for, if it is, it is printed. This routine also calls another routine
* which prints out the anethesia results and patient history info.
*
RPTPRT:     PSH A                   *Save the environment
            PSH B
            PSHX
*
            JSR     HEADER          *Print the header
            JSR     SPCHN2          *Process special case questions
            JSR     DISCLM          *Print the disclaimer
*
            LDX     #TITLE1         *Print the title
            JSR     PRTSTR
*
            LDX     #TARRAY         *Get address of test array
            STX     NXTTST
*
NXTQ:       LDX     0,X             *Get address of question data
            CLR A
            STA A   PFLAG           *Clear the print flag
            LDA A   0,X             *Get the test number
            BEQ     DONE
            INX                     *Advance to index count
            LDA A   0,X             *Get the number of indexes
            BEQ     NOQST           *No indexes? branch.
            STA A   NUMIDX          *Save the index count
            INX                     *Position to first entry
```

```
*
NXTANS: STX     OFFSET          *Save the index address
        LDX     0,X
        LDA B   0,X             *Get the index value
        LDX     #ANS1           *Get base address of answer array
        ABX                     *Add the index to the base
        LDA A   0,X             *Get question answer
        CMP A   NOANS           *NO ANSWER do not print
        BEQ     OV1
        CMP A   NO              *If no, do not print test
        BEQ     OV1
        INC     PFLAG           *Yes or Don't know? Set print flag
OV1:    LDA A   NUMIDX          *Get index counter
        DEC A                   *Decrement counter
        BEQ     NOQST           *Testing done? Branch.
        STA A   NUMIDX          *Save counter value
        LDX     OFFSET          *Get index address
        LDA B   #2              *Move pointer to next entry
        ABX
        BRA     NXTANS          *Check next answer
*
NOQST:  LDX     OFFSET
        INX                     *Advance to test string
        INX
        TST     PFLAG           *If print flag set print test
        BEQ     OV2
        JSR     PRTSTR
OV2:    LDX     NXTTST          *Get the address of the array
        INX                     *Advance to next element
        INX
        STX     NXTTST          *Save address of new element
        BRA     NXTQ            *Check the new entry
*
DONE:   LDX     #TITLE2
        JSR     PRTSTR
        JSR     SPCHN1
*
        PULX                    *Restore the environment
        PUL B
        PUL A
        RTS
*
        XREF    PRTCHR
*
PRTSTR: PSH B
LOOP:   LDA B   0,X
        BEQ     OUT
        CMP B   #'$'
        BNE     PCHR
        LDA B   #13
        JSR     PRTCHR
        LDA B   #10
*
        NAM     LABTESTS
        LIST    1                               *Use 6801 Instruction Set
*
        XDEF    IARRAY,QARRAY,QCOUNT,TARRAY
        XDEF    W55,W57
        XDEF    W62,W63,W64,W67,W68,W69
        XDEF    Q58,Q59
        XDEF    Q60,Q61,Q62,Q63,Q64,Q67,Q68,Q69
        XDEF    Q70,Q71,Q72,Q73,Q74,Q75
        XDEF    W58Y,W59Y
        XDEF    W60Y,W61Y,W67Y,W67N,W68Y,W68N,W69Y,W69N
        XDEF    W70Y,W70N,W71Y,W71N,W72Y,W72N,W73Y,W74Y,W75Y
*
        PSCT
*
INTRO1: FCC     /Please answer the following questions.$/
        FCC     /To proceed, press your answer and then$/
        FCC     /the next question button.$/
```

```
            FCC     /Are you ready to continue?/
            FCB     0
INTRO2:     FCC     /Your answers to the following questions$/
            FCC     /will be used to assist your doctor in$/
            FCC     /taking care of you.$/
            FCC     /Are you ready to continue?/
            FCB     0
INTRO3:     FCC     /If you make a mistake you can change$/
            FCC     /your answer until you press the next$/
            FCC     /question button. Try it - Press yes then$/
            FCC     /no then yes then next question./
            FCB     0
INTRO4:     FCC     /If you make a mistake and have already$/
            FCC     /pressed the next question button. Please$/
            FCC     /return this machine so it may be reset.$/
            FCC     /Are you ready to continue?/
            FCB     0
INTRO5:     FCC     /Some of these questions are to let your$/
            FCC     /surgeon and anesthesiologist know more$/
            FCC     /about you should you need surgery.$/
            FCC     /Are you ready to continue./
            FCB     0
INTRO6:     FCC     /Take your time and answer each question$/
            FCC     /to the best of your knowledge.$/
            FCC     /There are 75 questions.$/
            FCC     /Are you ready to begin?/
            FCB     0
*
IARRAY:     FDB     INTRO1,INTRO2,INTRO3,INTRO4,INTRO5,INTRO6,QEND
*
*The following data is a list of the questions which will be asked to
*each person using the device. If there is additional output in the form
*of another question or a statement associated with the question that data
*will appear after the question. The format of each question is as follows:
*
*<label> <index><flag><class> <string> [<string>[<yes string>[<no string>]]]
*
*label : The label is the reference to the question entry. Lables begin with
*         either a Q for question of W for associated string. The number is
*         the question number. If the label is an associated string (begins
*         with a W) the last character will be either a Y for the yes response
*         a N for the no response or a blank indicating a question to be
*         printed for additional information.
*
*index : This value is the question number and the offset into the answer
*         array.
*
*flag  : This is a general purpose flag an currently has 3 possible values.
*            0 is the default (no meaning)
*            1 indicates the question has an associated string
*            2 indicates the question should only be asked to females
*
*class : This value classifies the question into one of the three classes
*            1 questions for lab tests
*            2 questions for anesthesia
*            3 questions for general health
*
*string: The string is the text of the question. Each line may be no longer
*         than 40 characters (excluding the $ symbol). Only 4 lines are
*         allowed and the fourth line may only be 30 characters. The $ symbol
*         is used to indicate a CRLF to the output routine and is not displaye
*
*                   /----------1---------2---------3---------4/
*
Q01:        FCB     1,0,1    ****** LAB TEST QUESTION ******
*
            FCC     /Have you taken Asprin, Excedrin, Anacin,$/
            FCC     /Bufferin, Alka Seltzer or any similar$/
            FCC     /medications in the last week?/
            FCB     0
Q02:        FCB     2,0,1    ****** LAB TEST QUESTION ******
```

```
         FCC   /Do you currently take drugs to suppress$/
         FCC   /your immune system such as cyclosporin,$/
         FCC   /azathioprine, imuran, cyclophosphamide,$/
         FCC   /or 6-mercaptopurine?/
         FCB   0
Q03:     FCB   3,0,1    ****** LAB TEST QUESTION ******
*
         FCC   /Have you ever been treated for cancer$/
         FCC   /with chemotherapy or x-ray radiation$/
         FCC   /therapy?/
         FCB   0
Q04:     FCB   4,0,1    ****** LAB TEST QUESTION ******
*
         FCC   /Do you have or have you had problems$/
         FCC   /with your blood such as anemia,$/
         FCC   /leukemia, or sickle cell disease?/
         FCB   0
Q05:     FCB   5,0,1    ****** LAB TEST QUESTION ******
*
         FCC   /Have you ever had a bleeding problem or$/
         FCC   /a blood clotting problem?/
         FCB   0
Q06:     FCB   6,0,1    ****** LAB TEST QUESTION ******
*
         FCC   /Are your stools ever bloody or black$/
         FCC   /and tarry?/
         FCB   0
Q07:     FCB   7,0,1    ****** LAB TEST QUESTION ******
*
         FCC   /Have you vomited blood or material that$/
         FCC   /looks like coffee grounds in the last$/
         FCC   /6 months?/
         FCB   0
Q08:     FCB   8,0,1    ****** LAB TEST QUESTION ******
*
         FCC   /Did you receive a blood transfusion$/
         FCC   /within the last six months?/
         FCB   0
Q09:     FCB   9,0,1    ****** LAB TEST QUESTION ******
*
         FCC   /Did you receive a blood transfusion$/
         FCC   /after 1979?/
         FCB   0
Q10:     FCB   10,0,1   ****** LAB TEST QUESTION ******
*
         FCC   /Have you ever required a blood$/
         FCC   /transfusion for excessive bleeding?/
         FCB   0
Q11:     FCB   11,0,1   ****** LAB TEST QUESTION ******
*
         FCC   /Have you lost more than 5% of your usual$/
         FCC   /body weight in the last year?/
         FCB   0
Q12:     FCB   12,0,3   *** GENERAL HEALTH QUESTION ***
*
         FCC   /Has your appetite for food changed in$/
         FCC   /the last year?/
         FCB   0
Q13:     FCB   13,0,3   *** GENERAL HEALTH QUESTION ***
*
         FCC   /Are you eating the same foods as you$/
         FCC   /were a year ago?/
         FCB   0
Q14:     FCB   14,0,1   ****** LAB TEST QUESTION ******
*
         FCC   /Have you ever smoked half a pack or more$/
         FCC   /cigarettes per day on a regular basis?/
         FCB   0
Q15:     FCB   15,0,1   ****** LAB TEST QUESTION ******
*
```

```
            FCC    /Have you smoked half a pack or more$/
            FCC    /cigarettes per day within the last$/
            FCC    /two weeks?/
            FCB    0
Q16:        FCB    16,0,1      ****** LAB TEST QUESTION ******
  *
            FCC    /Have you quit smoking and continued$/
            FCC    /without cigarettes for 4 weeks?/
            FCB    0
Q17:        FCB    17,0,1      ****** LAB TEST QUESTION ******
  *
            FCC    /Have you quit smoking and continued$/
            FCC    /without cigarettes for 5 years?/
            FCB    0
Q18:        FCB    18,0,1      ****** LAB TEST QUESTION ******
  *
            FCC    /Do you suffer from shortness of breath,$/
            FCC    /chest pain, emphysema, asthma, or$/
            FCC    /bronchitis?/
            FCB    0
Q19:        FCB    19,0,1      ****** LAB TEST QUESTION ******
  *
            FCC    /Do you cough regulary or frequently?/
            FCB    0
Q20:        FCB    20,0,1      ****** LAB TEST QUESTION ******
  *
            FCC    /Do you cough up sputum?/
            FCB    0
Q21:        FCB    21,0,1      ****** LAB TEST QUESTION ******
  *
            FCC    /In the last month have you noticed a$/
            FCC    /change in the color or consistency of$/
            FCC    /the sputum?/
            FCB    0
Q22:        FCB    22,0,1      ****** LAB TEST QUESTION ******
  *
            FCC    /In the last 4 weeks have you had a$/
            FCC    /fever, chills, cold, or flu?/
            FCB    0
Q23:        FCB    23,0,1      ****** LAB TEST QUESTION ******
  *
            FCC    /Have you ever had a heart attack or been$/
            FCC    /treated for a possible heart attack?/
            FCB    0
Q24:        FCB    24,0,1      ****** LAB TEST QUESTION ******
  *
            FCC    /Do you have heart problems such as$/
            FCC    /skipped heart beats, angina or$/
            FCC    /chest pain?/
            FCB    0
Q25:        FCB    25,0,1      ****** LAB TEST QUESTION ******
  *
            FCC    /Do you currently take quinidine, inderal$/
            FCC    /diltiazem, verapramil, nifedipine,$/
            FCC    /nitroglycerine, or propranolol, digoxin$/
            FCC    /lanoxin, digitoxin or digitalis?/
            FCB    0
Q26:        FCB    26,0,1      ****** LAB TEST QUESTION ******
  *
            FCC    /Do you currently take any medication$/
            FCC    /for high blood pressure?/
            FCB    0
Q27:        FCB    27,0,1      ****** LAB TEST QUESTION ******
  *
            FCC    /Have you been told by your doctor to$/
            FCC    /exercise and diet to control high blood$/
            FCC    /pressure?/
            FCB    0
Q28:        FCB    28,0,1      ****** LAB TEST QUESTION ******
  *
            FCC    /Have you ever woken up at night and felt$/
```

```
            FCC    /short of breath?/
            FCB    0
Q29:        FCB    29,0,1    ****** LAB TEST QUESTION ******
 *
            FCC    /Do you become short of breath after$/
            FCC    /climbing one flight of stairs or after$/
            FCC    /walking a short distance?/
            FCB    0
Q30:        FCB    30,0,3    *** GENERAL HEALTH QUESTION ***
 *
            FCC    /Are you able to walk up stairs at the$/
            FCC    /same rate you could 5 years ago?/
            FCB    0
Q31:        FCB    31,0,1    ****** LAB TEST QUESTION ******
 *
            FCC    /Do you currently take water pills or$/
            FCC    /diuretics?/
            FCB    0
Q32:        FCB    32,0,1    ****** LAB TEST QUESTION ******
 *
            FCC    /Do you currently take potassium pills$/
            FCC    /or powder?/
            FCB    0
Q33:        FCB    33,0,3    *** GENERAL HEALTH QUESTION ***
 *
            FCC    /Have your bowel or bladder functions$/
            FCC    /changed in the last year?/
            FCB    0
Q34:        FCB    34,0,1    ****** LAB TEST QUESTION ******
 *
            FCC    /Do you have any problems with your$/
            FCC    /kidneys?/
            FCB    0
Q35:        FCB    35,0,1    ****** LAB TEST QUESTION ******
 *
            FCC    /Have you ever been told you have$/
            FCC    /diabetes or sugar diabetes?/
            FCB    0
Q36:        FCB    36,0,1    ****** LAB TEST QUESTION ******
 *
            FCC    /Do you often wake up to urinate more$/
            FCC    /than once a night?/
            FCB    0
Q37:        FCB    37,0,3    *** GENERAL HEALTH QUESTION ***
 *
            FCC    /Have you engaged in sex (intercourse)$/
            FCC    /within the last 2 weeks?/
            FCB    0
Q38:        FCB    38,0,3    *** GENERAL HEALTH QUESTION ***
 *
            FCC    /Is your level of sexual desire and$/
            FCC    /activity normal for you?/
            FCB    0
Q39:        FCB    39,0,1    ****** LAB TEST QUESTION ******
 *
            FCC    /Do you currently take anti-coagulents or$/
            FCC    /blood thinning medicine?/
            FCB    0
Q40:        FCB    40,0,1    ****** LAB TEST QUESTION ******
 *
            FCC    /Have you ever had prolonged or unusual$/
            FCC    /bleeding from nosebleeds, tooth$/
            FCC    /extractions, cuts or surgery?/
            FCB    0
Q41:        FCB    41,0,1    ****** LAB TEST QUESTION ******
 *
            FCC    /Do you bleed from your gums when you$/
            FCC    /brush your teeth?/
            FCB    0
Q42:        FCB    42,0,1    ****** LAB TEST QUESTION ******
 *
```

```
          FCC    /Have you ever been diagnosed as having a$/
          FCC    /serious bleeding problem?/
          FCB    0
Q43:      FCB    43,0,1      ****** LAB TEST QUESTION ******
*
          FCC    /Has a family member or blood relative$/
          FCC    /ever been diagnosed as having a serious$/
          FCC    /bleeding disorder?/
          FCB    0
Q44:      FCB    44,0,1      ****** LAB TEST QUESTION ******
*
          FCC    /Have you ever had kidney stones, kidney$/
          FCC    /failure, dialysis, or infection of the$/
          FCC    /kidney?/
          FCB    0
Q45:      FCB    45,0,1      ****** LAB TEST QUESTION ******
*
          FCC    /Have you ever had hepatitis, yellow$/
          FCC    /jaundice, liver disease or malaria?/
          FCB    0
Q46:      FCB    46,0,1      ****** LAB TEST QUESTION ******
*
          FCC    /Have you ever been exposed to anyone$/
          FCC    /with yellow jaundice or hepatitis?/
          FCB    0
Q47:      FCB    47,0,1      ****** LAB TEST QUESTION ******
*
          FCC    /Have you ever been exposed to anyone$/
          FCC    /with yellow jaundice or hepatitis within$/
          FCC    /the last 6 months?/
          FCB    0
Q48:      FCB    48,0,1      ****** LAB TEST QUESTION ******
*
          FCC    /Do you often drink more than three$/
          FCC    /alcoholic drinks per day? (Three shots,$/
          FCC    /three beers, or three glasses of wine?)/
          FCB    0
Q49:      FCB    49,0,1      ****** LAB TEST QUESTION ******
*
          FCC    /Within the last 2 years have you taken,$/
          FCC    /injected or smoked any non-prescription$/
          FCC    /drugs such as cocaine, marijuana, LSD,$/
          FCC    /herion, etc./
          FCB    0
Q50:      FCB    50,0,1      ****** LAB TEST QUESTION ******
*
          FCC    /Have you been exposed to the body$/
          FCC    /secretions (blood, urine, saliva, etc.)$/
          FCC    /of anyone likely to have the AIDS virus?/
          FCB    0
Q51:      FCB    51,0,1      ****** LAB TEST QUESTION ******
*
          FCC    /Are you in a high risk group for AIDS?$/
          FCC    /(Homosexual, Bisexual, had sex with a$/
          FCC    /prostitute in the last 6 years or have$/
          FCC    /Hemophilia.)/
          FCB    0
Q52:      FCB    52,0,1      ****** LAB TEST QUESTION ******
*
          FCC    /Would you like to receive a test to find$/
          FCC    /out if you have been exposed to the$/
          FCC    /AIDS virus?/
          FCB    0
Q53:      FCB    53,0,1      ****** LAB TEST QUESTION ******
*
          FCC    /Do you have any pain or discomfort with$/
          FCC    /urination, or have you noticed any$/
          FCC    /blood in your urine?/
          FCB    0
Q54:      FCB    54,0,1      ****** LAB TEST QUESTION ******
*
```

|       | FCC | /Are you female?/ |
|       | FCB | 0 |
| Q55:  | FCB | 55,2,1     ****** LAB TEST QUESTION ****** |
|       | FCC | /Do you have any reason to believe you$/ |
|       | FCC | /are pregnant or that you may possably$/ |
|       | FCC | /be pregnant?/ |
|       | FCB | 0 |
| W55:  | FCC | /Date of your last normal menstrual period?$/ |
|       | FCB | 0 |
| Q56:  | FCB | 56,0,1     ****** LAB TEST QUESTION ****** |
|       | FCC | /Do you have muscle cramps or spasms in$/ |
|       | FCC | /your legs more than three times$/ |
|       | FCC | /per year?/ |
|       | FCB | 0 |
| Q57:  | FCB | 57,1,1     ****** LAB TEST QUESTION ****** |
|       | FCC | /Are you going to have an operation?/ |
|       | FCB | 0 |
| W57:  | FCC | /What operation are you going to have?$/ |
|       | FCB | 0 |
| Q58:  | FCB | 58,0,2     ***** ANESTHESIA QUESTION ***** |
|       | FCC | /Do you wear dentures, partial or a$/ |
|       | FCC | /bridge?/ |
|       | FCB | 0 |
| W58Y: | FCC | /Patient wears dentures.$/ |
|       | FCB | 0 |
| Q59:  | FCB | 59,0,2     ***** ANESTHESIA QUESTION ***** |
|       | FCC | /Do you have any capped teeth?/ |
|       | FCB | 0 |
| W59Y: | FCC | /Patient has capped teeth.$/ |
|       | FCB | 0 |
| Q60:  | FCB | 60,0,2     ***** ANESTHESIA QUESTION ***** |
|       | FCC | /Do you wear contact lenses?/ |
|       | FCB | 0 |
| W60Y: | FCC | /Patient wears contact lenses.$/ |
|       | FCB | 0 |
| Q61:  | FCB | 61,0,2     ***** ANESTHESIA QUESTION ***** |
|       | FCC | /Do you have any teeth loose?/ |
|       | FCB | 0 |
| W61Y: | FCC | /Patient has loose teeth.$/ |
|       | FCB | 0 |
| Q62:  | FCB | 62,1,2     ***** ANESTHESIA QUESTION ***** |
|       | FCC | /Do you have any allergies?/ |
|       | FCB | 0 |
| W62:  | FCC | /What are you allergic too?$/ |
|       | FCB | 0 |
| Q63:  | FCB | 63,1,2     ***** ANESTHESIA QUESTION ***** |
|       | FCC | /Have you had anesthesia in the past?/ |
|       | FCB | 0 |

```
*
W63:    FCC     /When did you previously have anesthesia?$/
        FCB     0
*
Q64:    FCB     64,1,2      ***** ANESTHESIA QUESTION *****
*
        FCC     /Have you or any other member of your$/
        FCC     /family or blood relatives had any$/
        FCC     /problems with anesthesia in the past?/
        FCB     0
*
W64:    FCC     /What problems have you or any member of your family had$/
        FCC     /with anesthesia?$/
        FCB     0
*
Q65:    FCB     65,0,1      ****** LAB TEST QUESTION ******
*
        FCC     /Are you older than 59?/
        FCB     0
Q66:    FCB     66,0,1      ****** LAB TEST QUESTION ******
*
        FCC     /Are you older than 39?/
        FCB     0
Q67:    FCB     67,0,1      ****** LAB TEST QUESTION ******
*
        FCC     /Have you had blood tests in the last$/
        FCC     /6 months?/
        FCB     0
*
W67:    FCC     /Where did you have a blood test in the /
        FCC     /last 6 months?$/
        FCB     0
W67Y:   FCC     /Patient has had a blood test in the last 6 months.$/
        FCB     0
W67N:   FCC     /Patient may not have had a blood test in the last 6 months.$
        FCB     0
*
Q68:    FCB     68,0,1      ****** LAB TEST QUESTION ******
*
        FCC     /Have you had a chest X-ray in the last$/
        FCC     /2 months?/
        FCB     0
*
W68:    FCC     /Where did you have a chest X-RAY in the /
        FCC     /last 2 months?$/
        FCB     0
W68Y:   FCC     /Patient has had a chest X-RAY in the last 2 months.$/
        FCB     0
W68N:   FCC     /Patient may not have had a chest X-RAY in the last 2 months.
        FCB     0
*
Q69:    FCB     69,0,1      ****** LAB TEST QUESTION ******
*
        FCC     /Have you had an EKG in the last$/
        FCC     /2 months?/
        FCB     0
*
W69:    FCC     /Where did you have an EKG in the last 2 months?$/
        FCB     0
W69Y:   FCC     /Patient has had an EKG in the last 2 months.$/
        FCB     0
W69N:   FCC     /Patient may not have had an EKG in the last 2 months.$/
        FCB     0
*
Q70:    FCB     70,0,1      ****** LAB TEST QUESTION ******
*
        FCC     /Has your stool been checked for blood in$/
        FCC     /the last year?/
        FCB     0
*
```

```
W70Y:   FCC     /Patients stool has been checked for /
        FCC     /blood in the last year.$/
        FCB     0
W70N:   FCC     /Patients stool may not have been checked /
        FCC     /for blood in the last year.$/
        FCB     0
*
Q71:    FCB     71,2,1      ****** LAB TEST QUESTION ******
*
        FCC     /Have you had a pap smear in the last$/
        FCC     /year?/
        FCB     0
*
W71Y:   FCC     /Patient has had a pap smear in the last year.$/
        FCB     0
W71N    FCC     /Patient may not have had a pap smear in the last year.$/
        FCB     0
*
Q72:    FCB     72,2,1      ****** LAB TEST QUESTION ******
*
        FCC     /Have you had a mammogram (X-Rays of your$/
        FCC     /breasts) in the last year?/
        FCB     0
*
W72Y:   FCC     /Patient has had a mammogram in the last year.$/
        FCB     0
W72N    FCC     /Patient may not have had a mammogram in the last year.$/
        FCB     0
*
Q73:    FCB     73,0,3      *** GENERAL HEALTH QUESTION ***
*
        FCC     /Have you been diagnosed as having a$/
        FCC     /hiatus hernia?/
        FCB     0
*
W73Y:   FCC     /Patient has been diagnosed as having a hiatus hernia.$/
        FCB     0
*
Q74:    FCB     74,0,3      *** GENERAL HEALTH QUESTION ***
*
        FCC     /Have you had heartburn within the last$/
        FCC     /month?/
        FCB     0
*
W74Y:   FCC     /Patient has heartburn.$/
        FCB     0
*
Q75:    FCB     75,0,3      *** GENERAL HEALTH QUESTION ***
*
        FCC     /Do you take Cimetidine, Ranitidine$/
        FCC     /Tagamet, or Zantac?/
        FCB     0
*
W75Y:   FCC     /Patient takes Cimetidine.$/
        FCB     0
*
QEND:   FCB     0
*
*
QCOUNT: FCB     75
*
* The following array of pointers contains the address of the first
* character in each of the question strings.
*
QARRAY: FDB     Q01,Q02,Q03,Q04,Q05,Q06,Q07,Q08,Q09
        FDB     Q10,Q11,Q12,Q13,Q14,Q15,Q16,Q17,Q18,Q19
        FDB     Q20,Q21,Q22,Q23,Q24,Q25,Q26,Q27,Q28,Q29
        FDB     Q30,Q31,Q32,Q33,Q34,Q35,Q36,Q37,Q38,Q39
        FDB     Q40,Q41,Q42,Q43,Q44,Q45,Q46,Q47,Q48,Q49
        FDB     Q50,Q51,Q52,Q53,Q54,Q55,Q56,Q57,Q58,Q59
```

```
         FDB     Q60,Q61,Q62,Q63,Q64,Q65,Q66,Q67,Q68,Q69
         FDB     Q70,Q71,Q72,Q73,Q74,Q75
         FDB     QEND
*
* This section of the data contains the various tests. An array of question
* pointers corresponding to the question number is stored here. A positive
* or don't know will result in the associated test being performed.
* The data format is:
*
*        byte 1    <tval> test index
*        byte 2    <icnt> Number of pointers in the following array
*        byte 3    <idx1>
*        byte N    <idxN> N = 3 + idx1
*        byte N+1         Test name string
*
TEST01:  FCB     1,13
         FDB     Q01,Q02,Q03,Q04,Q05,Q06,Q07,Q08,Q10,Q11,Q12,Q54,Q65
TSTR01:  FCC     /CBC$/
         FCB     0
*
TEST02:  FCB     2,2
         FDB     Q21,Q22
TSTR02:  FCC     /DIFF$/
         FCB     0
*
TEST03:  FCB     3,5
         FDB     Q39,Q40,Q41,Q42,Q43
TSTR03:  FCC     /PLATELETS$/
         FCB     0
*
TEST04:  FCB     4,1
         FDB     Q53
TSTR04:  FCC     /URINALYSIS$/
         FCB     0
*
TEST05:  FCB     5,1
         FDB     Q55
TSTR05:  FCC     /BHCG$/
         FCB     0
*
TEST06:  FCB     6,5
         FDB     Q39,Q40,Q41,Q42,Q43
TSTR06:  FCC     /PT$/
         FCB     0
*
TEST07:  FCB     7,5
         FDB     Q39,Q40,Q41,Q42,Q43
TSTR07:  FCC     /PTT$/
         FCB     0
*
TEST08:  FCB     8,4
         FDB     Q11,Q12,Q48,Q56
TSTR08:  FCC     /CALCIUM$/
         FCB     0
*
TEST09:  FCB     9,3
         FDB     Q11,Q12,Q48
TSTR09:  FCC     /MAGNESIUM$/
         FCB     0
*
TEST10:  FCB     10,1
         FDB     Q65
TSTR10:  FCC     /CHEM 17$/
         FCB     0
*
TEST11:  FCB     11,6
         FDB     Q12,Q25,Q31,Q32,Q34,Q44
TSTR11:  FCC     /POTASSIUM$/
         FCB     0
*
TEST12:  FCB     12,3
```

```
           FDB      Q11,Q12,Q48
TSTR12:    FCC      /PHOSPHORUS$/
           FCB      0
*
TEST13:    FCB      13,6
           FDB      Q12,Q45,Q46,Q47,Q48,Q49
TSTR13:    FCC      /SGPT$/
           FCB      0
*
TEST14:    FCB      14,3
           FDB      Q11,Q12,Q48
TSTR14:    FCC      /ALBUMIN$/
           FCB      0
*
TEST15:    FCB      15,3
           FDB      Q12,Q34,Q44
TSTR15:    FCC      /BUN$/
           FCB      0
*
TEST16:    FCB      16,3
           FDB      Q12,Q34,Q44
TSTR16:    FCC      /CREAT$/
           FCB      0
*
TEST17:    FCB      17,2
           FDB      Q35,Q36
TSTR17:    FCC      /GLUCOSE$/
           FCB      0
*
TEST18:    FCB      18,6
           FDB      Q15,Q18,Q19,Q20,Q21,Q65
TSTR18:    FCC      \CHEST XRAY PA/LAT$\
           FCB      0
*
TEST19:    FCB      19,10
           FDB      Q23,Q24,Q25,Q26,Q27,Q28,Q29,Q31,Q65,Q66
TSTR19:    FCC      /EKG$/
           FCB      0
*
TEST20:    FCB      20,5
           FDB      Q09,Q49,Q50,Q51,Q52
TSTR20:    FCC      /Suggest HIV$/
           FCB      0
*
TEND:      FCB      0
*
*
TARRAY FDB         TEST01,TEST02,TEST03,TEST04,TEST05
       FDB          TEST06,TEST07,TEST08,TEST09,TEST10
       FDB          TEST11,TEST12,TEST13,TEST14,TEST15
       FDB          TEST16,TEST17,TEST18,TEST19,TEST20
       FDB          TEND
*
           END

* These routines are the system software. All drivers and setup code
* is included here SYSINT.ASM
SERDRV.ASM
EQULIB.ASM
TERMHAN.ASM
DISDRV.ASM
TERUTL.ASM
CNTHAN.ASM
ESCHAN.ASM
CNTSUB.ASM
ESCSUB.ASM
DISHAN.ASM
QUEHAN.ASM
RAMSCT.ASM
```

TERHAN.ASM
LCD.ASM
SYSINT1.ASM
KEYHAN.ASM
KEYHAN1.ASM

*APPENDIX IV*
*© ARCH Development Corp. 1985,*

```
        NAME    ASKQ
*
        LIST    1                       *Use the 6801 Instruction set
*
        XDEF    ASKQ,STRDSP,GETANS,ANS1,ANS2,QAPTR
        XDEF    YES,NO,IDNO,ENTER,NOANS,QVALID
*
* This routine is called to ask the questions and save the answers in
* the two answer arrays (normal and complemented). A valid flag is used
* to ensure that all of the questions were answered and that the routine
* was terminated normally.
*
*List the externally used functions
*
        XREF CLR.SC,KY.HAN,OUTCHR
*
*List the externally defined memmory locations
*
        XREF    IARRAY,QARRAY
*
ARYSIZ  EQU     77+1
NBRNCH  EQU     1
BSTKSZ  EQU     ARYSIZ+ARYSIZ
*
        DSCT
*
QVALID  RMB     1
QNUM    RMB     1
ANS1    RMB     ARYSIZ
ANS2    RMB     ARYSIZ
PSTACK  RMB     BSTKSZ          *History (path) stack for backup
PTHSTK  RMB     2
SYSSTK  RMB     2
QAPTR   RMB     2
A1SUM   RMB     1
A2SUM   RMB     1
*
        PSCT
*
*******************************SUBROUTINE ASKQ
*
ASKQ:   PSH A                   *Save the A, B and X registers
        PSH B
        PSHX
*
* Set up the history stack to save the question path to be used
* by the BACKUP proceedure
*
        SEI                     *Disable interrupts
        LDX     #PSTACK         *Get Path stack address
        LDA B   #BSTKSZ         *Get Path stack length
        ABX                     *Set to top of stack
        STS     SYSSTK          *Save current system stack
        TXS                     *Set new stack address
        LDX     #0              *Set the top indicator on path stack
        PSHX
        STS     PTHSTK
        LDS     SYSSTK
        CLI                     *Enable interrupts
```

```
*
* This loop will display instruction messages in the address array
* IARRAY until the first character to display is 0.
*
        LDX     #IARRAY         *Get address of instruction array
IMSG:   JSR     CLR.SC          *Clear the display
        PSHX
        LDX     0,X             *Get address of string to display
        LDA B   0,X             *First byte = 0? Done.
        BEQ     IDONE
        JSR     STRDSP          *Display the message
        JSR     GETANS          *Wait for input
        PULX
        INX
        INX
        BRA     IMSG
*
IDONE:  PULX                    *Clean up the stack
*
        LDA A   #4
        STA A   QVALID          *Set first half of valid flag
*
* Fill the answer arrays with the NO ANSWER value
*
        LDX     #ANS1           *Initialize the positive array
        LDA A   ARYSIZ          *Get the size of the array
        LDA B   NOANS
IARY1:  STA B   0,X
        INX
        DEC A                   *Decrement the count
        BNE     IARY1           *Branch until finished LDX     #ANS2           *Initialize the negative array
        LDA A   ARYSIZ          *Get the size of the array
        LDA B   NOANS
        NEG B                   *Negate the value
IARY2:  STA B   0,X
        INX
        DEC A                   *Decrement the count
        BNE     IARY2           *Branch until finished
*
* This loop will display the questions and save the users answer in
* the two answer arrays. As above 0 is the terminator.
*
        LDX     #QARRAY         *Get question address array
        LDX     0,X             *Get address of the first question
        STX     QAPTR           *Seed the question pointer
*
NXTQ:   LDX     QAPTR           *Get current question address
        LDA B   0,X             *Read the question index (ACC-B)
        STA B   QNUM            *Save index
        BEQ     DONE            *End of questions? Exit.
        INX                     *Advance to question flag (skip over)
*
        INX                     *Set to address of question string
        INX
        JSR     CLR.SC          *Clear display screen
        JSR     STRDSP          *Display the question
        JSR     GETANS          *Get the users answer (Returned in ACC-A)
*
        SEI                     *Disable Interrupts
        PSHX                    *Save current X value
        STS     SYSSTK          *Save system stack
        LDS     PTHSTK          *Set up the path stack
        CMP A   BKUP            *BACKUP command?
        BNE     SVQST           *No, save current question on stack
        PULX                    *Yes, retrive previous question
        CPX     #0              *At top of stack?
        BNE     BOV1            *No
        PSHX                    *Yes, push indicator back on stack
        BRA     BOV2
```

```
BOV1:    STX     QAPTR           *Set to previous question
         LDA B   0,X             *Get question index
         LDX     #ANS1           *Clear answer in array 1 (NOANS)
         ABX
         LDA A   NOANS
         STA A   0,X
         LDX     #ANS2           *Clear answer in array 2 (NOANS)
         ABX
         NEG A
         STA A   0,X
         STS     PTHSTK          *Save path stack
BOV2:    LDS     SYSSTK          *Restore system stack
         PULX                    *Clean up stack
         CLI                     *Enable interrupts
         BRA     NXTQ            *Go ask the new question
*
SVQST:   LDX     QAPTR           *Get current question
         PSHX                    *Save on the path stack
         STS     PTHSTK          *Save the path stack
         LDS     SYSSTK          *Restore system stack
         PULX                    *Restore X value
         CLI                     *Enable interrupts
*
         INX                     *Move data pointer to flag
         LDA B   0,X             *Get the branch flag
         INX                     *Set to first pointer
         CMP B   #NBRNCH         *Conditional branch question?
         BEQ     SETNXT          *No, branch.
         CMP A   NO              *Paitent answer is NO?
         BNE     SETNXT
         INX                     *Skip to NO related question
         INX
SETNXT:  LDX     0,X             *Pick up next question address
         STX     QAPTR           *Save address
*
         LDA B   QNUM            *Get question address
         LDX     #ANS1           *Load address of first answer array
         ABX                     *Add question offset (Offset is in ACC-A)
         STA A   0,X             *Save the answer
         ADD A   A1SUM           *Add new answer to sum
*
         NEG A                   *Complement the answer
         LDX     #ANS2           *Load address of second answer array
         ABX                     *Add question offset (Offset is in ACC-A)
         STA A   0,X             *Save the complemented answer
         ADD A   A2SUM           *Add complement to sum
*
         JMP     NXTQ            *Ask next question
*
DONE:    LDA A   QVALID
         ADD A   #40H            *And in second half of valid flag
         STA A   QVALID          *Set the valid flag
         PULX                    *Restore the A, B, and X registers
         PUL B
         PUL A
         RTS
*
* This routine accepts a string pointed to by the X register. The
* string is output to the screen until an EOL is found. The
* "$" character is used to indicate CRLF and is replaced by those
* characters.
*
*****************************SUBROUTINE STRDSP
*
STRDSP:  PSH B
STR1:    LDA B   0,X
         BEQ     OUT
         CMP B   #'$'
         BNE     OV1
         LDA B   #13
         JSR     OUTCHR
```

```
            LDA B     #10
            JSR       OUTCHR
            INX
            BRA       STR1
*
OV1:        PSHX
            CMP B     #$61              *Convert to upper case
            BLO       OV2
            CMP B     #$7A
            BHI       OV2
            SUB B     #$20
*
OV2:        JSR       OUTCHR
            PULX
            INX
            BRA       STR1
*
OUT:        PUL B
            RTS
*
* This routine will accept input from the 4 keys and will echo
* the users response on the display. The response will not be
* returned until the user presses ENTER. The users response
* is returned in ACC A.
*
            DSCT
DVAL:       RMB       1
*
            PSCT
*
YESSTR: FCC     /  YES  /
        FCB     0
NOSTR:  FCC     /  NO   /
        FCB     0
IDNSTR: FCC     /NOT SURE/
        FCB     0
BKPSTR: FCC     / BACKUP /
        FCB     0
*
****************
* NOTE: If the declarations below are changed make sure you change PRTQST.ASM
****************
*
YES:    FCB     12
NO:     FCB     13
IDNO:   FCB     14
ENTER:  FCB     15
BKUP:   FCB     11
NOANS   FCB     20
*
*******************************************SUBROUTINE GETANS
*
GETANS: PSH B
        PSHX
        CLR A
        STA A     DVAL
*
GETCH:  JSR       KY.HAN                *Get input in ACC-B
        TST B
        BEQ       GETCH
        TBA
        CMP A     DVAL                  *Same key (debounce)
        BEQ       GETCH                 *Yes ignore the input
        CMP A     YES                   *YES Key?
        BEQ       YESHAN
        CMP A     NO                    *NO Key?
        BEQ       NOHAN
        CMP A     IDNO                  *NOT SURE Key?
        BEQ       IDNHAN
        CMP A     BKUP                  *BACKUP key?
```

```
        BEQ     BUPHAN
        CMP A   ENTER           *ENTER or NEXT QUESTION Key?
        BEQ     ENTHAN
        BRA     GETCH
*
YESHAN: LDX     #YESSTR         *Display YES
        BRA     DISP
*
NOHAN:  LDX     #NOSTR          *Display NO
        BRA     DISP
*
IDNHAN: LDX     #IDNSTR         *Display NOT SURE
        BRA     DISP
*
BUPHAN: LDX     #BKPSTR         *Display BACKUP
*
DISP:   STA A   DVAL            *Save input
        JSR     POSCRS          *Position the cursor
        JSR     STRDSP          *Display the key stroke
        BRA     GETCH
*
ENTHAN: TST     DVAL            *Check  for valid input
        BEQ     GETCH           *NO, Ignore input
*
        LDA A   DVAL            *YES, Return input in ACC-A
        PULX
        PUL B
        RTS
*
* This routine positions the cursor to line 4 column 30
*
POSREP  FCB     27,61,35,64,0
*
POSCRS: PSHX
        LDX     #POSREP
        JSR     STRDSP
        PULX
        RTS
*
        END
        TITLE   'MAIN'
*
        NAME    MAIN
        LIST    1
*
        XDEF    MAIN,BSTRNG,DBKEY
*
        XREF    CLR.SC,ASKQ,STRDSP,GETANS,GETK16,KY.HAN
        XREF    HEADER,ENTER,QVALID,RPTPRT,PRTQST,OUTCHR
        XREF    SYDIAG,SETCLK
        XREF    YES
*
        PSCT
*
ALT1:   FCC     /$         ENTER ACCESS CODE$/
        FCC     /                           /
        FCB     0
ALT2:   FCC     / 1) ASK QUESTIONS     4) SET TIME$/
        FCC     / 2) PRINT RESULTS     5) RUN DIAGNOSTICS$/
        FCC     / 3) PRINT RESPONSES  ->> /
        FCB     0
MES2:   FCC     /$   -- PRINTING ANALYSIS RESULTS --/
        FCB     0
MES3:   FCC     /$   -- PRINTING PATIENT RESPONSES --/
        FCB     0
MES4:   FCC     /     THIS COMPLETES THE QUESTIONAIRE.$/
        FCC     /          THANK YOU FOR YOUR TIME$$/
        FCC     /   PLEASE RETURN THIS UNIT FOR ANALYSIS/
        FCB     0
```

```
MES5:    FCC      /$QUESTIONARE COMPLETED ENTER ACCESS CODE$/
         FCC      /                       /
         FCB      0
ERROR1:  FCC      /$    ERROR: THERE IS NO DATA TO PRINT.$/
         FCC      /$         ENTER ANY KEY TO CONTINUE/
         FCB      0
ERROR2:  FCC      /$    ERROR: INVALID ACCESS CODE.$/
         FCC      /$         ENTER ANY KEY TO CONTINUE/
         FCB      0
ERROR3:  FCC      /$    ERROR: INVALID COMMAND.$/
         FCC      /$         ENTER ANY KEY TO CONTINUE/
         FCB      0
*
*************************************SUBROUTINE MAIN
*
MAIN:    CLR A
         STA A    QVALID
*        JSR      GETK16
*        BRA      MAIN
*
AGAIN:   JSR      CLR.SC
         LDX      #ALT1              *Prompt for access code
         JSR      STRDSP
*
*        LDA B    #2                 *Echo X for password entry
         LDA B    #1                 ***********DEBUG INPUT
         STA B    ECOFLG
*
         JSR      GETVAL             *Get Integer input (ACC-X)
         CPX      #9999              ***********DEBUG
*        CPX      #9360              *Check against password
         BEQ      OPTION             *Valid display options
*
         JSR      CLR.SC             *Invalid display error message
         LDX      #ERROR2
         JSR      STRDSP
         JSR      DBKEY
         BRA      AGAIN
*
OPTION:  JSR      CLR.SC             *Display user options
         LDX      #ALT2
         JSR      STRDSP
         LDA A    #1
         STA A    ECOFLG             *Enable echo.
         JSR      GETVAL             *Read option (ACC-X)
         CPX      #1
         BEQ      OPT1               *ASK QUESTIONS
         CPX      #2
         BEQ      OPT2               *PRINT REPORT
         CPX      #3
         BEQ      OPT3               *PRINT PATIENT RESPONSES
         CPX      #4
         BNE      OP5                *SET TIME/DATE
         JMP      OPT4
OP5:     CPX      #5
         BNE      OPE                *RUN DIAGNOSTICS
         JMP      OPT5
*
OPE:     LDX      #ERROR3            *Invalid command
         JSR      CLR.SC
         JSR      STRDSP
         JSR      DBKEY
         BRA      OPTION
*
OPT1:    JSR      BDAY               *Get paitents birthday
         JSR      ASKQ               *Ask the questions
         JSR      CLR.SC
         LDX      #MES4
         JSR      STRDSP
         JSR      GETANS
```

```
*
AG1:    JSR     CLR.SC
        LDX     #MES5               *Prompt for access code
        JSR     STRDSP
*
        LDA B   #2                  *Echo X for password entry
        STA B   ECOFLG
*
        JSR     GETVAL              *Get Integer input (ACC-X)
        CPX     #9360               *Check against password
        BEQ     OPTION              *Valid display options
*
        JSR     CLR.SC              *Invalid display error message
        LDX     #ERROR2
        JSR     STRDSP
        JSR     DBKEY
        BRA     AG1
*
OPT2:   LDA A   QVALID              *Check if valid patient data
        CMP A   #44H
        BNE     NODATA              *Invalid print error message
        JSR     CLR.SC              *Clear the screen
        LDX     #MES2               *Print current operation message
        JSR     STRDSP
        JSR     RPTPRT
        JMP     OPTION
*
OPT3:   LDA A   QVALID              *Check if valid patient data
        CMP A   #44H
        BNE     NODATA              *Invalid print error message
        JSR     CLR.SC              *Clear the screen
        LDX     #MES3               *Print current operation message
        JSR     STRDSP
        JSR     HEADER
        JSR     PRTQST
        JMP     OPTION
*
NODATA: JSR     CLR.SC              *Print invalid data mesage
        LDX     #ERROR1
        JSR     STRDSP
        JSR     DBKEY
        JMP     OPTION
*
OPT4:   JSR     SYDIAG              *Run the system diagnostics
        JMP     OPTION
*
OPT5:   JSR     SETCLK              *Set the system date and time
        JMP     OPTION
*
*
BMES1:  FCC     /    -- ENTER PAITENTS BIRTHDAY --$/
        FCC     /              DDMMYYYY$/
        FCC     /                       /
        FCB     0
BMES2:  FCC     /$ IS THIS CORRECT? /
        FCB     0
*
        DSCT
*
CCNT:   RMB     1
BSTRNG: RMB     10
*
        PSCT
*
*************************SUBROUTINE BDAY
*
BDAY:   PSH A                       *Save environment
        PSH B
        PSHX
```

```
*
NBDAY:  JSR     CLR.SC
        LDX     #BMES1          *Prompt for paitents birthday
        JSR     STRDSP
*
        LDA A   #8              *Set character count to 8
        STA A   CCNT
        LDX     #BSTRNG         *Get storage for birthday string
NCHR:   JSR     DBKEY           *Get input
        CMP B   #'0'            *Check if valid input (0-9)
        BLO     NCHR
        CMP B   #'9'
        BHI     NCHR
        STA B   0,X             *Save character
        INX                     *Set to next string element
        JSR     OUTCHR          *Echo the character
        DEC     CCNT            *Check if all characters read
        BNE     NCHR            *No, get next string
        CLR A
        STA A   0,X             *Yes, save EOS
*
        LDX     #BMES2          *Output check string
        JSR     STRDSP
        LDX     #BSTRNG         *Output birthday string
        JSR     STRDSP
        JSR     GETANS          *Get users answer
        CMP A   YES             *String OK?
        BNE     NBDAY           *No, start over
*
        PULX                    *Yes, restore environment
        PUL B
        PUL A
        RTS DSCT
*
NUMBER: RMB     2
NVAL1:  RMB     1
NVAL2:  RMB     1
NVAL3:  RMB     1
ECOFLG: RMB     1
*
* This routine accepts numeric input and will echo the input on the screen
* if the echo flag is set. The input is converted to an integer and returned
* in the INDEX register.
*
        PSCT
*********************************SUBROUTINE GETVAL
*
GETVAL: PSH A
        PSH B
        LDD     #0
        STD     NUMBER          *Clear the integer accumulator
        STD     NVAL1
*
NXTNUM: JSR     DBKEY           *Get input
        CMP B   ENTER           *Input terminated?
        BEQ     FIN
        SUB B   #48             *Convert from ASCI to Integer
        CMP B   #0              *Make sure input is a valid number
        BLT     NXTNUM
        CMP B   #9
        BGT     NXTNUM
*
        STA B   NVAL2           *Save the number
        TST     ECOFLG          *Echo flag on?
        BEQ     NOECO
        ADD B   #48             *Yes, convert to ASCI and display it
        LDA A   #2
```

```
            CMP A   ECOFLG          *Special password echo
            BNE     OV1
            LDA B   #'X'
*
OV1:        JSR     OUTCHR          *Echo input
*
NOECO:      LDD     NUMBER          *Get the previous value
            ASLD                    *Multiply by 10
            ASLD
            ADDD    NUMBER
            ASLD
            ADDD    NVAL1           *Add in the new value (16 bit)
            STD     NUMBER          *Save new sum
            BRA     NXTNUM          *Get next character
*
FIN:        LDX     NUMBER          *Load result in ACC-X
            PUL B
            PUL A
            RTS
*
* This routine is used to debounce the user input. The value will not be
* returned until the user releases the key.
*
**********************************SUBROUTINE DBKEY
*
DBKEY:      JSR     KY.HAN          *Get input
            TST B                   *Wait for some input > 0
            BEQ     DBKEY
            STA B   NVAL3           *Save the key
*
DEB:        JSR     KY.HAN          *Debounce by waiting for change
            CMP B   NVAL3
            BEQ     DEB
*
            LDA B   NVAL3
            RTS
*
            END
*
 TITLE 'INITIALIZE SYSTEM'
*
* THIS ROUTINE IS ENTERED APON POWER UP AND IT INITIALIZE THE FOLLOWING
* STACK POINTER
* PORT 1
* SERIAL PORT
* TIMER PORT
* PIA
* IT WILL FIND OUT FROM THE DIP SWITCH WHAT MODE WERE IN
* AND GOES TO THAT HANDLER
*
* OPT REL,LLE=120,Z01
 NAM SYSINT
 LIST 1
* IDNT SYSTEM INITIALIZATION 12-05-84
* ADDED TT.HAN DISPATCH     12-11-84
*
* EXTERNAL DEFINTION
*
 XDEF SY.INT
*
* EXTERNAL REFERENCES SUBROUTINE
*
 XREF TR.INT,DSPTCH,SD.INT
* XREF SL.INT
*
* EXTERNAL REFERENCES DATA&PORTS
*
 XREF PIACTA,PIACTB,PIADRB,PIADRA,DPSWTH
 XREF PR.FLG,CR.FLG,BD.RAT,PRASTR
```

```
*
 XREFB P1DDR,PORT1,P2DDR,P3DDR,TRSR,TCSR,RMCR,PORT4,P4DDR
* EXTERNAL REFERENCE EQUATES
*
 XREF P1DDRI,P2DDRI,P3DDRI,PRT1IN,MODSEL,BAUDMK
 XREF SWSLCL,SWSLST,PRT4IN,P4DDRI,SDMOD,TERMOD,PRCFLG,CRCFLG
 XREF RAMSTR,RAMEND,STKSTR,TMCTIN
*
 PSCT
*
SY.INT LDS #STKSTR
 LDAA #P1DDRI
 STAA P1DDR
 LDAA #PRT1IN
 STAA PORT1
 LDAA #P2DDRI
 STAA P2DDR
 LDAA #P3DDRI
 STAA P3DDR
 LDAA #P4DDRI
 STAA P4DDR
 LDAA PRT4IN
 STAA PORT4
 LDX #RAMSTR
 LDAA #$55
RAM.LP STAA X
 INX
 CPX #RAMEND+1
 BNE RAM.LP
RAM.L1 DEX
 CMPA X
 BNE RAM.FL
 CPX #RAMSTR
 BNE RAM.L1
 CMPA #$AA
 BEQ RAM.DN
 LDAA #$AA
 BRA RAM.LP
RAM.FL BRA RAM.FL
RAM.DN LDS #STKSTR
*JMP TT.INT
*
* INITIALIZE SERIAL & TIMER PORT
*
*LDAA #TMCTIN
*STAA TCSR
*
* INITIALIZE PIA
*
*CLR PIACTA
*CLR PIACTB
*CLR PIADRA
*LDAA #$FF
*STAA PIADRB
*LDAA #4
*STAA PIACTA
*STAA PIACTB
*
* INPUT THE SWITCHES AND SET THE BAUD RATE
* GO TO THE PROPER HANDLER
*
 CLR $F CLEAR CONTROL STATUS REGISTER
 LDAB PORT4
 ANDB #SWSLCL SELECT THE SWITCH
 STAB PORT4
 LDAA #BAUDMK
 ANDA DPSWTH
 LDAB PORT4
 ORAB #SWSLST
 STAB PORT4
 CLRB
```

```
  INCB  START OUT WITH 9600 BAUD
  CLC   PREPARE FOR ROTATE
  ROLA
  ROLA
  ROLA
  BEQ SYSIN0
  TAB 1-1 EQUAL 300
  EORA #3 INVERT A 300 BAUD WOULD BE 0
  BEQ SYSIN0
  TAB        0-1 9600 1-0 1200
SYSIN0 STAB BD.RAT
* BNE SYSIN1
* INCA ZERO SHOULD BE 9600 BAUD
SYSIN1 ORAB #4 OR IN NRZ INTERNAL CLOCK
  STAB RMCR
  LDAA PRASTR    *
  ANDA #PRCFLG   *
  ANDA #CRCFLG   *
  STAA PRASTR    *
  LDAA PORT4
  ANDA #SWSLCL SELECT THE SWITCH
  STAA PORT4
  LDAB #MODSEL  FIND OUT WHAT MODE WE'RE IN
  ANDB DPSWTH
  LDAA PORT4
  ORAA #SWSLST
  STAA PORT4
  LDX #MODROT
  JSR DSPTCH
END BRA END
*
* LIST OF MODE HANDLER
*
MODROT FCB TERMOD
  FDB TR.INT
  FCB SDMOD
  FDB SD.INT
  FCB $FF
* FDB SL.INT
  FCB $FF
  FDB $FFFF
  END
   TITLE ' SERIAL PORT DRIVER ROUTINE'
*
* FOR RIGHT NOW ANY TIME A KEY IS HIT THE THIS PROGRAM JUMPS
* TO THE SOFTWARE INTERRUPT ROUTINE
*
*
  XREF TRSR,REVDAT,TRNDAT,WR.QUE,RMCR,HL.HAN,PORT1
  XDEF SR.INT,REVCHR,SENCHR,PRTCHR
ESC    EQU  $1B
FEOE   EQU  $40
TRRDY  EQU  $20
  PSCT
SR.INT PSHA
  LDAA #$05
  STAA RMCR NRZ 9600 BAUD
  LDAA #$1A ENABLE REVCEIVE INTERRUPTS
  STAA TRSR
  PULA
  RTS
****************************************************************
*
* RECEIVE A BYTE OF DATA FROM THE LOCAL SERIAL PORT
*      IF ERROR THEN RETURN
*   ELSE IF ESC THEN GO TO DEBUGGER
*      END IF
*   ELSE RETURN WITH CHARACTER IN B
* ENDIF
```

```
*
REVCHR LDAA TRSR
   LDAB REVDAT
   ANDA #FEOE
   BNE  REVCH3
   CMPB #03
   BNE  REVCH1
   JMP  $F821
REVCH1 JSR  WR.QUE
*      JSR  HL.HAN
REVCH3 RTI
***********************************************************************
*
* TRANSMIT A CARACTER THE LOCAL SERIAL LINE
* CHARACTER IS IN A
SENCHR PSHB
SENCH1 LDAB TRSR
   ANDB #TRRDY
   BEQ  SENCH1
   STAA TRNDAT
   PULB
   RTS

***********************************************************************
*
* TRANSMIT A CARACTER THE LOCAL SERIAL LINE
* CHARACTER IS IN A
PRTCHR PSHA
PRTCH1 LDAA TRSR
   ANDA #TRRDY
   BEQ  PRTCH1
PRTCH2 LDAA PORT1
   ANDA #$10 DTR
   BNE  PRTCH2
   STAB TRNDAT
   PULA
   RTS

END
*
   TITLE 'ONE LINE SYSTEM EQUATES'
*  OPT REL,LLE=120,Z01
   NAME EQULIB
*  IDNT EQUATE LIBRARY 11-30-84
*
*
   XDEF P1DDR,P2DDR,PORT1,PORT2,TCSR,TIMREG,RMCR,TRSR,REVDAT
   XDEF TRNDAT,RDRF,ORFE,TDRE,RIE,RID,RE,RD,TIE,TID,TE,TD,TMCTIN
   XDEF P1DDRI,P2DDRI,PRT1IN,DTSTBT,DTRTBT,EXDTCL,SWIMSK,LINLGT,ROWMAX
   XDEF COLMAX,CURCHR,PRERCH,ORFECH,BAUDMK,MODSEL,ESC,CR,XON
   XDEF XOFF,PIASTR,PIADRA,DPSWTH,PIACTA,PIADRB,DSDTPT,PIACTB
   XDEF NORMAL,SPACE,OTCPRG,TIMCNT,FLASH,OTCPEN,COMFLG
   XDEF POSMAX,OLVL,P3DDR,P3DDRI,PORT4,SWSLST,SWSLCL,PORT3,P4DDRI,PRT4IN,P4DDR
   XDEF SDMOD,TERMOD
   XDEF RELSET,RELRST
*
* PERIPHERAL EQUATES
*
   BSCT
P1DDR RMB 1
P2DDR RMB 1
PORT1 RMB 1
PORT2 RMB 1
P3DDR RMB 1
P4DDR RMB 1
PORT3 RMB 1
PORT4 RMB 1
TCSR RMB 1 TIMER CONTROL AND STATUS REGISTER
TIMREG RMB 2
OTCPRG RMB 2
   RMB 3
```

```
RMCR   RMB 1 SCI RATE AND CONTROL REG
TRSR   RMB 1 TRANSMIT/RECEIVE CONTROL AND STATUS REG
REVDAT RMB 1 RECEIVE DATA REGISTER
TRNDAT RMB 1  TRANSMIT DATA REGISTER
RESVED RMB 12 RESERVED AREA
*
* TRANSMIT/RECEIVE CONTROL AND STATUS REGISTER
* BIT EQUATES
*
RDRF EQU $80
ORFE EQU $40
TDRE EQU $20
RIE EQU $10
RID EQU $EF RECEIVE INTERRUPT DISABLE MASK
RE EQU $8
RD EQU $F8 RECEIVE DISABLE
TIE EQU $4
TID EQU $FB TRANSMIT INTERRUPT DISABLES
TE EQU 2 TRANSMIT ENABLED
TD EQU $FD TR5NSMIT DISABLED
OLVL EQU 1
*
* TIMER INITIALIZE
*
TMCTIN EQU 0
TIMCNT EQU 120
OTCPEN EQU %0001000
*
* PORT 1 EQUATES
*
P1DDRI EQU %01111001
P2DDRI EQU %00000010
P3DDRI EQU 0
P4DDRI EQU %00111101
PRT1IN EQU %01000000
PRT4IN EQU $10
DTSTBT EQU $01 SET DTR
DTRTBT EQU $FE RESET DTR
EXDTCL EQU $F7 ENABLE EXTERNAL DATA RATE CLOCK
SWIMSK EQU 6 SWITCH MASK
COMFLG EQU   $40
*
* DISPLAY EQUATES
*
LINLGT EQU 40 LINE LENGHT
ROWMAX EQU 3
COLMAX EQU 39
CURCHR EQU $7F CURSOR CHARACTER
PRERCH EQU 0 PARITY
* ERROR CHARACTER
ORFECH EQU 0 OVERRUN PARITY ERROR CHARACTER
POSMAX EQU (LINLGT*ROWMAX)+COLMAX
*
* SWITCH EQUATES
*
BAUDMK EQU $C0
MODSEL EQU $30
SWSLST EQU $10
SWSLCL EQU SWSLST!X$FF
*
* MODE SELECT SWITCH SETTING EQUATES
* FOR 1 AND 2 LINER S/T VERSION
*
* MODE     SWITCH   8 7
*TERMINAL MODE     1 0
*SMART MODE        1 1
*SLAVE MODE        0 X   X=DON'T CARE
*
*
TERMOD EQU $20 TERMINAL MODE SWITCH SETTING
```

```
SDMOD  EQU  $30 SMART MODE SWITCH SETTING
SLMOD  EQU  $10 SLAVE MODE SWITCH SETTING
SLMOD1 EQU  $00 SLAVE MODE SWITCH SETTING
*
* ASCII EQUATES
*
ESC   EQU  $1B
CR    EQU  $0D
XON   EQU  $11
XOFF  EQU  $13
SPACE EQU  $20
*
*  PIA ADDRESS
*
PIASTR EQU $7000
PIADRA EQU PIASTR
DPSWTH EQU PORT3
PIACTA EQU PIASTR+1
PIADRB EQU PIASTR+2
DSDTPT EQU PORT3
PIACTB EQU PIASTR+3
*
* SERIAL RAM COMM EQUATES
*
RAMPRT EQU PORT4
RMWTST EQU 03
RMWTRT EQU RMWTST!X$FF
RMCLST EQU 01
RMCLRT EQU RMCLST!X$FF
RMSLST EQU 08
RMSLRT EQU RMSLST!X$FF
RMRDST EQU 02
RMRDRT EQU RMRDST!X$FF
*
* DISPLAY ATTRIBUTES EQUATES
*
FLASH  EQU '2
NORMAL EQU '0
*
*DIGTAL OUTPUT EQUATES
*
RELSET EQU $08
RELRST EQU RELSET!X$FF
 END
*
 TITLE 'TERMINAL HANDLER'
* TERMINAL HANDLER FOR THE 4 LINE TERMINAL MODE OF OPERATION
* UPON RESET OF THE PROCESSOR THE 4 LINER PROGRAMMING SWITCH
* STATE IS LOADED INTO THE PROCESSOR AND IF THE TERMINAL MODE
* IS SELECETED THEN THIS ROUTINE IS INVOKED AND WILL NEVER EXIT
* UNTIL THE PROCESSOR IS RESET
* THE FIRST OPERATION IS TO SET THE COMMUNICATION PARAMETERS
* CLEAR THE SCREEN AND STATUS FLAGS
*
* OPT REL,Z01,LLE=120
 NAM TERHAN
 LIST 1
* IDNT TERMINAL HANDLER
*
 XDEF TR.INT,TR.MAN
 XDEF SWTCNT
*
*EXTERNAL CONSTANTS AND DATA LOCATIONS
*
 XREFB ES.FLG,ESC
 XREFB FL.FLG,MN.FLG,PR.FLG,CR.FLG
 XREFB HF.FLG,CURSOR,SWSLCL,SWSLST
 XREFB PORT1,PORT4,TCSR,DPSWTH
 XREF PRASTR
```

```
*
*EXTERNAL ROUTINES
*
 XREF CN.HAN,DS.HAN,ES.INT,ES.HAN,RD.QUE
 XREF CLR.SC,IN.QUE,DS.INT,ENRVIN,SR.INT,SET.SC,WAIT
*
*EXTERNAL EQUATES ROUTINES
*
 XREFB OLVL,DTSTBT,SWIMSK
*
* LOCAL EQUATES
*
SWTCNT EQU 6
RSOLVL EQU $FE CLEAR OLVL
WAITTM EQU $32*$FF
*
* DATA COMMON FOR SWITCH PARAMETER
*
* PROGRAM STARTS HERE WITH TR.INT INITIALIZATION ROUTINE
*
 PSCT
TR.INT JSR CLR.SC
 JSR IN.QUE
 CLR ES.FLG
 CLR FL.FLG
 LDAB PORT4
 ANDB #SWSLCL
 STAB PORT4
 LDAA #$0F    GET THE CONTENTS OF THE DIPSWITCH
 ANDA DPSWTH
 LDAB PORT4
 ORAB #SWSLST
 STAB PORT4
 LSLA
 LSLA
 LDAB #SWIMSK
 ANDB PORT1
 LSRB
 ABA
 STAA PRASTR *
* LDX #PRASTR+2 SET THE PARAMETER FLAGS
* LDAB #SWTCNT GET THE SWITCH COUNT
*TR.IN1 CLR X CLEAR OUT THE FLAG FIRST
* RORA
* BCC TR.IN2
* INC X
*TR.IN2 INX
* DECB
* BNE TR.IN1
 LDAA TCSR
 ORAA #OLVL
 LDAB #HF.FLG  *
 ANDB PRASTR   *
* TST HF.FLG
 BEQ TR.IN3
 ANDA #RSOLVL
TR.IN3 STAA TCSR
 CLR MN.FLG
 JSR SR.INT
 JSR DS.INT INTIALIZE THE DISPLAY DRIVER
* JSR SET.SC
* CLI
* LDX #WAITTM
* JSR WAIT
* SEI
 JSR CLR.SC
 JSR ENRVIN ENABLE REV. INTERRPUPTS
 LDAA #DTSTBT
 ORAA PORT1
```

```
 STAA PORT1
 CLI
*
*
* THIS IS THE MAIN TERMINAL PROGRAM IT WILL RUN IN FOREGROUND
* IT WILL READ THE QUE AND DEPENDING ON THE STATUS OR CHARACTER
* IT WILL VECTOR OF TO THE APPROPIATE ROUTINE
*
*
TR.MAN JSR RD.QUE GET A CHARACTER FROM THE QUE
 BEQ TR.MAN
*TR.MAN BRA TR.MAN IF Z=1 THEN QUE IS EMPTY
*
* QUE IS NOT EMPTY WE GOT A CHARACTER
* CHARACTER IS IN B
*
 CMPB #ESC
 BNE TR.MA1
 JSR ES.INT
 BRA TR.MAN
TR.MA1 TST ES.FLG IS THE ES.FLG SET
 BEQ TR.MA2
 JSR ES.HAN IF SET THIS CHARACTER IS PART OF A ESCAPE SEQUENCE
 BRA TR.MAN
TR.MA2 CMPB #$20 IS IT A CONTROL CHARACTER?
 BGE TR.MA3
 JSR CN.HAN YES IT IS A CONTROL CHARACTER
 BRA TR.MAN
TR.MA3 JSR DS.HAN
 BRA TR.MAN
 END
*
 TITLE 'ONE LINE DISPLAY DRIVER'
*
* THIS ROUTINE WILL OUTPUT A ROW OF CHARACTERS TO THE DRIVER
* THATS POINTED TO BY COLCNT.
* THE ROW SEQUENCE IS DICTATED BY THE SEQUENCE OF ROW NUMBERS
* IN CHRPTN MEMORY BLOCK
*
* OPT REL,LLE=120,Z01
 NAME DISDRV
 LIST 1
*
 XDEF FLSHCT
*
*LOCAL MEMORY LOCATIONS
*
 DSCT
COLCNT RMB 1
FLSHCT RMB 2
ROWCNT RMB 1
FLSHST RMB 1
*
*LOCAL EQUATES
*
FLCTMX EQU $380 MAX FLASH RATE
STCLMK EQU $BF START CLEAR MASK
STSTMK EQU $40 START SET MASK
CLDTST EQU $20 CLOCK DATA SET
CLDTRT EQU $DF CLOCK DATA RESET
DSCLST EQU $10 CATHODE ENABLE DATA SET
DSCLRT EQU $EF CATHODE ENABLE DATA RESET
CLDSRT EQU $CF
DONE EQU $80 DONE BIT
*
*
* EXTERNAL ROUTINE DEFINTION
*
 XDEF DS.DRV,DS.INT
```

```
*
* EXTERNAL DATA DEFINITION
*
  XREFB CURSOR,DSDTPT,OTCPRG,TIMREG,CR.FLG
  XREFB WTEMP,PRASTR
*
  XREFB PORT1,TCSR,P3DDR
*
* EXTERNAL EQUATES REFERENCES
*
  XREF SCBFST,TIMCNT
  XREFB SPACE,ROWMAX,CURCHR,COLMAX,OTCPEN
*
* ROW SEQUENCE DATA
*
  PSCT
CHRPTN FCB 00
*
*
*
* DISPLAY DRIVER INIT
* INITIALIZE ALL THE DRIVERS VARIBLES
* AND ENABLE THE OUTPUT COMPARE REGISTER INTERRUPT
*
DS.INT CLRA
 STAA FLSHCT
 STAA FLSHCT+1
 STAA FLSHST
 STAA ROWCNT
 STAA WTEMP
 STAA WTEMP+1
 LDAA #COLMAX
 STAA COLCNT
 LDAA TCSR
 LDD TIMREG
 ADDD #TIMCNT
 STD OTCPRG
 LDAA #OTCPEN
 ORAA TCSR
 STAA TCSR
 LDAA #$FF
 STAA P3DDR
 RTS
*
* PROGRAM STARTS HERE
* THE FLASH COUNT IS INC
* IT CHECKS TO SEE IF THE FLASH COUNT IS AT IT'S MAX AND
* THEN IF IS THEN IT TOGGLES THE FLASH STATUS AND CLEARS THE COUNT
* THEN IT OUTPUT THE CHARACTERS AS SEQUENCE IN CHRPTN
* IT ALSO TAKES CARE OF THE CURSOR
* IT THEN ENABLE THE COLUMN DRIVERS
* THEN IT RE-ENTERS THE TIMER COUNT
* AND RTI
*
DS.DRV LDX FLSHCT INCREMENT THE FLASH COUNT
 INX
 CLR ROWCNT
 CPX #FLCTMX ARE WE AT OUR MAX
 BNE DISDR1
 COM FLSHST TOGGLE
 LDX #0
DISDR1 STX FLSHCT
 LDX WTEMP
 BEQ DISD11
 DEX
 STX WTEMP
DISD11 LDX #CHRPTN GET THE START OF THE SEQUENCE
 LDAB ROWCNT AND THE ROW COUNT
DISDR2 ABX POINT TO THE PROPER ROW
 LDAB X GET IT IN B
 LDAA COLCNT GET THE CURRENT COLUMN COUNT
```

```
 ABA GET THE RIGHT CHARACTER TO BE DISPLAYED
 TAB
 LDX #SCBFST
 ABX GET THE POINTER TO THE CHARACTER   C
 LDAB PRASTR  *
 ANDB #CR.FLG *
* TST CR.FLG SEE IF WE DISPLAY THE CURSOR
 BEQ DISDR3
 CPX CURSOR ARE WE AT THE CURSOR POSITION
 BNE DISDR3
 TST FLSHST ARE ON OR OF IN
 BEQ DISDR3
 LDAA #CURCHR GET THE CURSOR CHARACTER
 BRA DISDR4 GO OUTPUT THE CHARACTER
DISDR3 LDAA X GET THE CHARACTER
 LDAB #$80 IS IT A FLASHING CHARACTER
 ANDB X
 BEQ DISDR4
 TST FLSHST
 BEQ DISDR4
 LDAA #SPACE GET A SPACE
DISDR4 LDAB PORT1
 ANDB #DONE
 BNE DISDR4 IF NOT DONE GO CHECK AGAIN
 STAA DSDTPT OUTPUT THE CHARACTER
 LDAB #STCLMK OUTPUT THE START PULSE
 ANDB PORT1
 STAB PORT1
 ORAB #STSTMK NEGATE THE START PULSE
 STAB PORT1
 INC ROWCNT POINT TO THE NEXT ROWCNT
 LDX #CHRPTN GET THE POINTER TO THE SEQUENCE
 LDAB ROWCNT ARE WE DONE WITH THE COLUMN
 CMPB #ROWMAX+1
 BNE DISDR2
*
* DECREMENT THE COLUMN COUNTER IF ZERO THE SET THE DATA TO ONE BEFORE
* CLOCKING THE CATHODE DRIVERS
* BEFORE LATCHING IN DATA INTO BUFFERS TIME OUT ON DONE (OOPS!!!)
*
DISD41 LDAA PORT1
 ANDA #DONE
 BNE DISD41
 LDAA COLCNT
 CMPA #COLMAX
 BNE DISDR5 IN NOT ZERO
 LDAA #CLDTST SET THE DATA BIT TO A ONE
 ORAA PORT1
 STAA PORT1
DISDR5 LDAA #DSCLST TOGGLE THE CLOCK PORT
 ORAA PORT1
 STAA PORT1
 LDAA #CLDSRT
 ANDA PORT1
 STAA PORT1
*
* SET UP THE COLUMN COUNT
 DEC COLCNT
*INC COLCNT
 LDAA COLCNT
 CMPA #-1
*CMPA #COLMAX+1
 BNE DISDR6
 LDAA #COLMAX
* CLR COLCNT
 STAA COLCNT
DISDR6 LDAA TCSR
 LDD TIMREG
 ADDD #TIMCNT
```

```
    STD OTCPRG
    RTI
*
    TITLE 'TERMINAL UTILITY ROUTINES'
*
* OPT REL,Z01.LLE=120
    LIST 1
    NAM TERUTL
*
* THESE ROUTINES ARE UTILITY PROGRAMS THAT ARE USED THROUGH OUT THE
* THE TERMINAL HANDLER
*
* ADD'D RELAY ON AND RELAY OFF FOR GENERAL USE
*
*
* EXTERNAL SUBROUTINES DEFINITIONS
*
    XDEF CURPOS,MVBLFD,MVBLRV,DSPTCH,DIVIDE,ENRVIN,DSRVIN
    XDEF CLR.LN,DSPBLK,BINBCD,WAIT,REL.ON,REL.OF
*
* EXTERNAL DATA DEFINITION
*
    XDEF TO.PNT,FR.PNT,WTEMP
*
* EXTERNAL DATA REFERENCE
*
    XREF CURSOR
*
* EXTERNAL EQUATE REFERENCE
*
    XREFB LINLGT,RIE,RID,SPACE
    XREFB ROWMAX,RELSET,RELRST
    XREF SCBFST
    XREFB TRSR,PORT4
*
    DSCT
TO.PNT RMB 2
FR.PNT RMB 2
*
    PSCT
*
    TITLE 'CURSOR POSITION'
*
* GET THE CURSOR BUFFER LOCATION AND DIVIDE IT BY THE LINE LENGHT
* A=ROW
* B=COLUNM
*
    DSCT
CURSTR RMB 2
    PSCT
CNT EQU 0
COL EQU 1
CURPOS PSHX
    LDX #CURSTR
    LDAA #ROWMAX
    STAA CNT,X
    LDD CURSOR
    SUBD #SCBFST
    STAB COL,X
    LDAA #LINLGT
    LDAB #ROWMAX
    MUL
CURLOP LDAA COL,X
    SBA
    BEQ CURPO1
    BHI CURPO1
    SUBB #LINLGT
    DEC CNT,X
    BNE CURLOP
    LDAA COL,X
```

```
CURP01 TAB       B=COLUNM
CURP02 LDAA CNT,X    A=ROW
 PULX
 RTS
*
 TITLE 'MOVE BUFFER LOCATIONS FOWARD'
*
* TAKE CONTENT POINTED BY FR.BUF AND PUT IT TO.BUF
* NUMBER OF TIMES THAT IS IN B
* THE BUFFER POINTERS ARE INCREMENTED
*
MVBLFD PSHX
 PSHA
MVBLF1 LDX FR.PNT
 LDAA X GET THE DATA POINTED TO BY THE FR.BUF
 INX INCREMENT IT BY 1
 STX FR.PNT PUT IT AWAY
 LDX TO.PNT GET THE POINTER TI WHERE WE WANT IT
 STAA X
 INX
 STX TO.PNT
 DECB
 BNE MVBLF1
 PULA
 PULX
 RTS
*
 TITLE 'MOVE BLOCK REVERSE'
*
* THIS ROUTINE DOES THE SAME AS FOWARD PUT REVERSE
*
MVBLRV PSHX
 PSHA
MVBLR1 LDX FR.PNT
 LDAA X GET THE CHARACTER
 DEX
 STX FR.PNT
 LDX TO.PNT
 STAA X
 DEX
 STX TO.PNT
 DECB
 BNE MVBLR1
 PULA
 PULX
 RTS
*
 TITLE 'DISPATCH ROUTINE'
* THIS ROUTINE TAKES A BYTE THAT IN --B-- AND
* GOES THROUGH A LIST POINTED TO BY --X--
* EVERY THIRD BYTE UNTIL IT FINDS A MATCH OR FINDS --FF--
* IF A MATCH IS FOUND THEN THE NEXT TWO BYTES ARE THE SUBROUTINES
* THAT WILL GOTO THAT SUBROUTINE AND RETURN A 0 IN THE --A--
* OTHERWISE IT WILL RETURN A NON-ZERO
*
DSPTCH PSHB TRANSFER B TO A
 TBA
DSPLOP CMPA X IS THIS THE MATCH
 BEQ DSPSUB
 LDAB X IS THE CHARACTER FF
 CMPB #$FF
 BNE DSPLP1
 INX
 LDAB #$FF
 CMPB X
 BNE DSPDEF
 CMPB 1,X
 BNE DSPDEF
 TBA PUT IT A
 BRA DSPEXT
```

```
DSPLP1 LDAB #3
 ABX POINT TO THE NEXT
 BRA DSPLOP
DSPSUB INX
DSPDEF LDX X
 JSR X
 CLRA SET ZERO BIT
DSPEXT PULB
 RTS
*
 TITLE 'DIVIDE ROUTINE'
*
* 8 BIT DIVIDE ROUTINE
* A=DIVIDEND
* B=DIVISOR
* RETURNS
* A=QUOTIENT
* B=REMIANDER
*
* LOCAL EQUATES
*
COUNT EQU 0
DIV EQU 1
QUO EQU 2
*
* LOCAL STORAGE
*
 DSCT
LOCSTO RMB 3
*
* PROGRAM STARTS HERE
*
 PSCT
DIVIDE PSHX
 LDX #LOCSTO
 CLR COUNT,X
 INC COUNT,X
 TSTB IS THE DIVSOR ZERO
 BEQ DIVEXT
 BMI DIV002
DIV001 INC COUNT,X
 ASLB DO IT UNTIL WE FIND A BIT
 BPL DIV001
 CLR QUO,X
 STAB DIV,X
DIV002 SUBA DIV,X
 BCC DIV003
 ADDA DIV,X
 CLC
 BRA DIV004
DIV003 SEC
DIV004 ROL QUO,X
 ROR DIV,X
 DEC COUNT,X
 BNE DIV002
 TAB
 LDAA QUO,X
DIVEXT PULX
 RTS
*
* ENABLE REVCEIVE INTERRUPTS
*
ENRVIN PSHA
 LDAA #RIE
 ORAA TRSR
 STAA TRSR
 PULA
 RTS
*
* DISABLE REVCEIVE INTERRUPT
```

```
*
DSRVIN PSHA
 LDAA #RID
 ANDA TRSR
 STAA TRSR
 PULA
 RTS
*
 TITLE 'CLEAR LINE'
*
* D=BUFFER POINTER
*
CLR.LN PSHB
 PSHA
 PSHX
 LDAB #LINLGT
 LDAA #SPACE
CLOOP STAA X
 INX
 DECB
 BNE CLOOP
 PULX
 PULA
 PULB
 RTS
*
* DISPLAY BLOCK OF CHARCTERS POINTED TO BY D AND
* PUT IT AT X INX X AND CHECK FOR A END OF FILE
* RETURN X POINTED TO THE NEXT SPOT
*
 DSCT
TEMP RMB 2
TEMP1 RMB 2
 PSCT
DSPBLK STD TEMP
DSPBL1 STX TEMP1
 LDX TEMP
 LDAA X GET THE CHARACTER TO BE DISPLAYED
 CMPA #$FF IS IT A END OF FILE
 BEQ DSPBEX
 INX
 STX TEMP SET UP FOR THE NEXT CHARACTER TO BE GOTTEN
 LDX TEMP1 GET WHERE WE ARE TO PUT THE CHARACTER
 STAA X
 INX SET UP FOR NEXT STORAGE LOCATION
 BRA DSPBL1
DSPBEX LDX TEMP1
 RTS
*
* BINARY TO BCD CONVERSION
* A = EQUAL BINARY NUMBER
* X POINTS TO STORAGE OF THREE DIGITS
* X=LSB
* X+2=MSB
*
BINBCD PSHB
 CLR X
 CLR 1,X
 CLR 2,X
BINBC1 TSTA
 BEQ BINBCE
 LDAB #10
 JSR DIVIDE
 STAB X
 INX
 BRA BINBC1
BINBCE PULB
 RTS
*
* WAIT FOR B*$FF OF INTERRUPT
```

```
*
 DSCT
WTEMP RMB 2
 PSCT
WAIT PSHA
 LDAA #$FF
 MUL
 STD WTEMP
WAIT1 LDD WTEMP
 BNE WAIT1
 PULA
 RTS
*
* TURN RELAY ON
*
REL.ON PSHA
 LDAA PORT4
 ORAA #RELSET
 STAA PORT4
 PULA
 RTS
*
* TURN RELAY OFF
*
REL.OF PSHA
 LDAA PORT4
 ANDA #RELRST
 STAA PORT4
 PULA
 RTS
 END
*
*
 TITLE 'CONTROL HANDLER'
*
* THIS ROUTINE TAKES THE CHARACTER THAT IS CONROL CODE
* AND COMPARES IT TO THE DISPATCH LIST IN THIS ROUTINE
* BUT IF THE WE ARE IN MONITOR MODE THEN THE CONTROL
* CODE IS THEN SENT TO THE DISPLAYABLE CHARACTER HANDLER
*
* OPT REL,Z01,LLE=120
 NAME CNTHAN
 LIST 1
*
*  EXTERNAL SUBROUTINE DEFINITIONS
*
 XDEF CN.HAN,CN.SUB
*
* EXTERNAL SUBROUTINES REFERENCES
*
 XREF DS.HAN,DSPTCH,LIN.FD,CAR.RT,CUR.UP,CUR.DN,CUR.LT,CUR.RT,CUR.HM
 XREF CRG.LF,XON.DS,XON.EN
*
* EXTERNAL DATA REFERENCES
*
 XREF MN.FLG
*
*
 PSCT
CN.HAN PSHX
 TST MN.FLG
 BEQ CN.HA1 IS THE MONITOR FLAG MODE SET
 JMP DS.HAN IS SO THEN GO TO DISPLAY HANDLER
CN.HA1 LDX #CN.SUB GET THE START OF THE SUBROUTINE LIST
 JSR DSPTCH
 PULX
 RTS
*
* SUBROUTINE LIST
```

```
*
CN.SUB FCB $0A ^J
 FDB LIN.FD
 FCB $0D ^M
 FDB CAR.RT
 FCB $0B ^K
 FDB CUR.UP
 FCB $16 ^V
 FDB CUR.DN
 FCB $08 ^H
 FDB CUR.LT
 FCB $0C ^L
 FDB CUR.RT
 FCB $14 ^^
 FDB CUR.HM
 FCB $1F ^_
 FDB CRG.LF
 FCB $0E ^N
 FDB XON.DS
 FCB $0F ^O
 FDB XON.DS
 FCB $FF EOF
 FDB $FFFF
 END
 TITLE 'ESCAPE HANDLER ROUTINE'
*
* THIS ROUTINE IS ENTER AT TWO PLACES
* ES.INT - WHEN A ESC CHARACTER IS FIRST FOUND
* ES.HAN - WHEN THE ESC FLAG IS SET THE ROUTINE IS ENTERED
*
* ALL ESCAPE SEQUENCES ARE INITIATED HERE
*
* EXTERAL DEFINITIONS SUBROUTINES
*
* OPT REL,Z01,LLE=120
 NAME ESCHAN
 LIST 1
*
 XDEF ES.INT,ES.HAN
*
* EXTERNAL REFERENCE DATA
*
 XREF ES.FLG,AT.FLG,DS.FLG,PS.FLG,CU.FLG
*
* EXTERNAL REFERENCES SUBROUTINES
*
 XREF DSPTCH,AT.HAN,PS.HAN,MON.MD,CAN.MD,DIS.ST,REV.LF,CLR.SC,SET.PS,SEN.CU
 XREF LIN.IN,LIN.DE,CLR.ES,AT.INT,CU.INT,CU.HAN
*
 PSCT
*
* PROGRAM STARTS HERE
*
ES.INT TST ES.FLG IS THE FLAG SET ALREADY
 BNE ES.IN1
 INC ES.FLG NOT SET SO SET IT
ES.IN1 CLR AT.FLG CLEAR OUT THE ATTRIBUTE FLAG
 CLR PS.FLG AND THE CURSOR POSITION FLAG
 CLR CU.FLG
ES.IN2 RTS
*
* THE MAIN ESCAPE ROUTINE THAT CALLS THE ESCAPE SEQUENCE ROUTINES
* VIA A DISPATCH ROUTINE AND SUBROUTINES LIST
*
ES.HAN TST CU.FLG
 BEQ ES.H1N
 JSR CU.HAN
 RTS
ES.H1N TST AT.FLG ARE WE IN CHARACTER ATTRIBUTE CHANGE MODE
 BEQ ES.HA1
```

```
 JSR AT.HAN ITS SET THE GO TO THE HANDLER
 RTS
ES.HA1 TST PS.FLG ARE WE IN CURSOR POSITION MODE
 BEQ ES.HA2
 JSR PS.HAN ITS SET GO TO THE HANDLER
 RTS
ES.HA2 PSHX
 LDX #ES.SUB GET THE BEGINNING OF THE SUBROUTINE LIST
 JSR DSPTCH
 PULX
 RTS
*
* ESCAPE SEQUENCE SUBROUTINES LISTS
*
ES.SUB FCC 'U'
 FDB MON.MD
 FCC 'u'
 FDB CAN.MD
 FCC 'X'
 FDB CAN.MD
* FCC 'h'
* FDB DIS.ST
 FCC 'J'
 FDB REV.LF
 FCC '*'
 FDB CLR.SC
 FCC '='
 FDB SET.PS
 FCC '?'
 FDB SEN.CU
 FCC 'G'
 FDB AT.INT
 FCC 'E'
 FDB LIN.IN
 FCC 'R'
 FDB LIN.DE
 FCC '.'
 FDB CU.INT
 FCB $FF
 FDB CLR.ES
 END
*
*
 TITLE 'CONTROL CODE SUBROUTINES'
* OPT REL,Z01,LLE=120
 NAME CNTSUB
 LIST 1
*
* THIS ROUTINE PERFORMS A LINE FEED
* IT DETERMINE WHAT LINE THE CURSORS ON AND
* SHIFTS THE LINES ACCORDINGLY IF NEEDED
*
* EXTERNAL SUBROUTINE DEFINTIONS
*
 XDEF LIN.FD,CUR.UP,CUR.DN,CUR.LT,CUR.RT,CAR.RT,CRG.LF,XON.DS,XON.EN,CUR.HM
*
* EXTERNAL SUBROUTINES REFERENCES
*
 XREF CURPOS,MVBLFD,CLR.LN,DISBUF,DISCUR
*
* EXTENAL DATA REFERENCES
*
 XREF CURSOR,TO.PNT,FR.PNT

XREFB XO.FLG,XOCFLG,PRASTR
*
* EXTERNAL EQUATE REFERENCES
*
 XREFB LINLGT,ROWMAX
 XREF SCBFST,SCBFED
```

```
 XREF SCBLGT SCBFST-SCBFED
 XREF SCBLG1 SCBFST-SCBFED-LINLGT
 XREF SCBLG2 SCBFST+LINLGT
*
* PROGRAM STARTS HERE
*
 PSCT
*
LIN.FD PSHX
 PSHB
 PSHA
 JSR CURPOS GET CURRENT CURSOR POSITION
 CMPA #ROWMAX ARE WE AT THE LAST ROW
 BLT LN.FE1
 LDD #SCBLG1+1
 LDX #SCBFST GET THE AMOUNT OF CHARACTERS AND START AND TO POINTER
 STX TO.PNT
 LDX #SCBLG2 FROM PIONTER
 STX FR.PNT
 JSR MVBLFD MOVE THE BUFFER FOWARD
 LDX TO.PNT
 JSR CLR.LN GO CLEAR THE LINE
 JSR DISBUF GO RE DISPLAY THE WHOLE SCREEN
 JSR DISCUR
 BRA LN.FEX GO AWAY
LN.FE1 JSR CUR.DN MOVE THE CURSOR DOWN
LN.FEX PULA
 PULB
 PULX
 RTS
*
   TITLE 'CURSOR UP'
*
* THIS ROUTINE PUT THE CURSOR UP ONE LINE
* IF THE CURSOR'S ON THE LAST LINE THEN GO TO THE BEGINNING LINE
*
CUR.UP PSHA
 PSHB
 PSHX
 LDD CURSOR
 SUBD #LINLGT SUBSTRACT THE A LINE LENGHT
 STD CURSOR
 LDX CURSOR
 CPX #SCBFST ARE WE BEFORE BEGINNING OF THE BUFFER
 BGE CUR.UE
 ADDD #SCBLGT+1
 STD CURSOR
CUR.UE JSR  DISCUR
 PULX
 PULB
 PULA
 RTS
*
  TITLE 'CURSOR DOWN'
*
* THIS ROUTINE MOVES THE CURSOR THE DOWN BY ONE LINE
* UNTIL THE END OF THE SCREEN THEN IT WILL PUT ON THE TOP
* THE SCREEN
*
CUR.DN PSHA
 PSHB
 PSHX
 LDX CURSOR
 LDAB #LINLGT ADD THE LINE LENGHT TO THE CURSOR
 ABX
 STX CURSOR
 CPX #SCBFED ARE PASS THE BOUNDARY
 BLE CUR.DE
 LDD CURSOR SUBTRACT THE WHOLE SCREEN WORTH
```

```
        SUBD #SCBLGT+1
        STD CURSOR PUT IT AWAY
CUR.DE  JSR DISCUR
        PULX
        PULB
        PULA
        RTS
*
*
 TITLE 'CURSOR LEFT'
*
* MOVE THE CURSOR LEFT BY ONE POSITION
* UNTIL BEGINNIG OF LINE THEN PUT AT THE NEXT LINE
* SAME WITH TOP OF PAGE TO END OF PAGE
*
CUR.LT  PSHX
        LDX CURSOR
        DEX
        CPX #SCBFST-1 ARE WE PAST THE BEGINNING OF THE BUFFER
        BNE CUR.LE
        LDX #SCBFED GET THE END OF SCREEN
CUR.LE  STX CURSOR
        JSR DISCUR
        PULX
        RTS
*
 TITLE 'CARRIAGE RETURN'
*
* THE ROUTINE PUTS THE CURSOR AT THE BEGINNING OF THE LINE
* THAT THE CURSOR'S ON
*
* CALL CURPOS
CAR.RT  PSHA
        PSHB
        PSHX
        JSR CURPOS GET THE CURRENT ROW POSITION IN A
        LDAB #LINLGT
        MUL MULTIPLY IN THE LINE LENGHT
        ADDD #SCBFST
        STD CURSOR
        JSR DISCUR
        PULX
        PULB
        PULA
        RTS
*
 TITLE 'CURSOR RIGHT'
*
* CURSOR IS MOVED RIGHT ONE POSITION IF AUTO CR LF SET
* THEN AT THE END OF LINE THE CURSOR IS PROGRESSED THE NEXT LINE
* AND IF AT END OF SCREEN THEN IT GOES TO THE BEGINNING
* ELSE THE CURSOR IS KEPT AT THE SAME POSITION
*
CUR.RT  PSHX
        LDX CURSOR
        INX
        CPX #SCBFED+1
        BNE CUR.R1
        LDX #SCBFST
CUR.R1  STX CURSOR
        JSR DISCUR
        PULX
        RTS
*
 TITLE 'CURSOR HOME'
*
CUR.HM  LDX #SCBFST
        STX CURSOR
        JSR DISCUR
        RTS
```

```
*
 TITLE 'CARRIAGE RETURN LINE FEED'
*
CRG.LF JSR LIN.FD
 JSR CAR.RT
 RTS
*
 TITLE 'XON.EN'
*
XON.EN PSHA   *
 LDAA PRASTR *
 ORAA #XO.FLG *
 STAA PRASTR *
* INC XO.FLG
 PULA         *
 RTS
*
 TITLE 'XON.DS'
*
XON.DS PSHA   *
 LDAA PRASTR *
 ANDA #XOCFLG *
 STAA PRASTR *
* CLR XO.FLG
 PULA         *
 RTS
 END
*  AND THE LAST LINE IS LOST
*
REV.LF PSHA
 PSHB
 PSHX
 LDX CURSOR GET THE CURSOR POSITION
 CPX #SCBLG2 IS IT ON THE TOP LINE
 BLT REV.L1
 JSR CUR.UP
 BRA REV.FE
REV.L1 LDD #SCBFED GET THE END OF THE BUFFER
 STD TO.PNT
 SUBD #LINLGT GET THE NEXT TO LAST LINE
 STD FR.PNT
 LDD #SCBLG1+1 GET THE AMOUNT OF CHARACTERS TO BE MOVE
 JSR MVBLRV
 LDX #SCBFST CLEAR THE TOP THE LINE
 JSR CLR.LN
 JSR DISBUF
 JSR DISCUR
REV.FE PULX
 CLR ES.FLG
 PULB
 PULA
 RTS
*
 TITLE 'INSERT LINE'
*
* IF LAST LINE JUST CLEAR THE LINE
* ELSE DO A REVERSE LINE FEED AT THE CURSOR POSTION
*
LIN.IN PSHA
 PSHB
 PSHX
 JSR CURPOS FIND OUT WHAT ROW OUR THE CURSORS ON
 CMPA #ROWMAX
 BEQ LIN.I1
 PSHA SAVE THE ROW NUMBER
 LDD #SCBFED
 STD TO.PNT
 SUBD #LINLGT THE START OF NEXT LINE DOWN
 STD FR.PNT
 PULB
 PSHB
```

```
   LDAA #ROWMAX
   SBA
   LDAB #LINLGT
   MUL
   JSR MVBLRV
   PULA GET THE ROW NUMBER
LIN.I1 LDAB #LINLGT GET THE LOCATION TO CLEAR OUT THE LINE
   MUL
   LDX #SCBFST
   ABX
   JSR CLR.LN CLEAR THE LINE
   JSR DISBUF
   JSR DISCUR
   CLR ES.FLG
   PULX
   PULB
   PULA
   RTS
*
   TITLE 'LINE DELETE'
*
* THIS ROUTINE DELETES THE LINE THE CURSORS ON
*
LIN.DE PSHA
   PSHB
   JSR CURPOS FIND OUT WHERES THE CURSOR
   LDAB #LINLGT
   MUL
   LDX #SCBFST
   ABX
   JSR CLR.LN
   JSR DISBUF
   JSR DISCUR
   CLR ES.FLG
   PULB
   PULA
   RTS
*
   TITLE 'SEND CURSOR INFORMATION'
*
* CURPOS IS CALLED AND THE CURPOSITION BOTH ROW AND COL
* ARE ADDED THE BASE AND SENT OUT TO THE SERIAL PORT
* FOLLOW BY A CARRIAGE RETURN
*
SEN.CU JSR CURPOS
   ADDA #BASE
*  JSR SD.DRV
   TBA
   ADDA #BASE
*  JSR SD.DRV
   LDAA #CR
*  JSR SD.DRV
   CLR ES.FLG
   RTS
*
   TITLE 'CLEAR SCREEN'
*
* CLEAR THE SCREEN AND INITIALIZE THE CURSOR
*
CLR.SC PSHX
*
   TITLE 'ECSAPE SEQUENCE SUBROUTINES'
*  OPT REL,Z01,LLE=120
   NAME ESCSUB
   LIST 1
*
* EXTERNAL SUBROUTINE DEFINITIONS
*
   XDEF MON.MD,CAN.MD,REV.LF,CLR.SC,SET.PS,SEN.CU,AT.INT,AT.HAN
   XDEF LIN.IN,LIN.DE,PS.HAN,CLR.ES,CU.HAN,CU.INT
   XDEF SET.SC
```

```
*XDEF DIS.ST,DSPBUD   NOT USED ON 1 AND 2 LINER
*
* EXTERNAL DATA DEFINITIONS
*
 XDEF CU.FLG
*
* EXTERNAL SUBROUTINE REFERENCES
*
 XREF MVBLFD,MVBLRV,CLR.LN,CURPOS,CUR.UP
 XREF DSPBLK,WAIT,DISBUF,DISCUR,DISCLC,DISSTC,DISCLR
*
* EXTERNAL DATA REFERENCES
*
 XREF TO.PNT,FR.PNT,CURSOR
 XREF AT.FLG,DS.FLG,PS.FLG,FL.FLG
 XREF ES.FLG,CR.FLG,BD.RAT,PR.FLG,ODEVPR,ATCRLF,HF.FLG
 XREFB XO.FLG,MN.FLG,CRCFLG,PRASTR
*
* EXTERNAL EQUATES MEMORY POINTERS
*
 XREF SCBFST,SCBFED,AUXSBF,AUXSBE
 XREF SCBLGT SCBFST-SCBFED
 XREF SCBLG1 SCBFST-SCBFED-LINLGT
 XREF SCBLG2 SCBFST+LINLGT
*
* EXTERNAL EQUATES
*
 XREFB LINLGT,CR,ROWMAX,FLASH,NORMAL,COLMAX,SPACE
 XREFB POSMAX
*
* LOCAL EQUATES
*
BASE EQU $20
*
 PSCT
*
 TITLE 'REVERSE LINE FEED'
*
* THE REVERSE LINE FEED
* THIS ROUTINE IF THE CURSOR NOT ON THE TOP THE IT IS MOVED UP ONE
*   ELSE THE SCREEN IS SCROLLED DOWN
 PSHA
 LDX #SCBFST
 STX CURSOR
 LDAA #SPACE
CLRLOP STAA X
 INX
 CPX #SCBFED+1
 BNE CLRLOP
 JSR DISCLR
 JSR DISCUR
 CLR ES.FLG
 PULA
 PULX
 RTS
*
* SET SCREEN TO ALL $7F
*
SET.SC PSHX
 PSHA
 LDX #SCBFST
 LDAA #$FF
SETLOP STAA X
 INX
 CPX #SCBFED+1
 BNE SETLOP
 JSR DISBUF
 JSR DISCUR
 CLR ES.FLG
 PULA
```

```
    PULX
    RTS
*
    TITLE 'CURSOR POSITION HANDLER'
*
* THERE ARE TWO ENTRY POINTS TO THIS ROUTINE
*    ONE SETS THE PS.FLG
*    THE SECOND TAKES IN TWO CHARACTER
*    THEN SETS THE CURSOR TO THE CHARACTER-BASE
*
    DSCT
ROWPOS RMB 1
COLPOS RMB 1
    PSCT
*
*
SET.PS INC PS.FLG SET THE POSITION FLAG
    LDAA #1
    RTS
*
* DEPENDING ON THE PS.FLG
* EITHER STORE THE ROW POSITION
* OR IF LAST CHARACTER ITS THE COLUMN
* REPOSITON CHARACTER
*
PS.HAN SUBB #BASE
    BMI PS.EXT
    LDAA PS.FLG
    DECA
    BNE PS.HA2 IS PS.FLG 1
    CMPB #ROWMAX
    BLE PS.HA1
    LDAB #ROWMAX GREATER THAN THE MAXIMUM THEN PUT THE MAX INTO THE BUFFER
PS.HA1 INC PS.FLG
    STAB ROWPOS
    RTS
PS.HA2 CMPB #COLMAX IS IT GREATER THAN COLUMN MAX
    BLE PS.HA3
    LDAB #COLMAX
PS.HA3 STAB COLPOS
    LDAB #LINLGT
    LDAA ROWPOS GET THE ROW POSITION SAVE
    MUL
    ADDB COLPOS
    ADDD #SCBFST
    STD CURSOR
    JSR DISCUR
PS.EXT CLR PS.FLG ALL DONE CLR THE FLAG
    CLR ES.FLG
    RTS
*
    TITLE 'DISPLAY ATTRIBUTE HANDLER'
*
* TWO ENTRY POINTS
* AT.INT INITIALIZES THE ATTRIBUTE FLAG
* AT.HAN SET OR RESET THE FLASH FLAG
* DEPENDING ON THE WHATS IN B
* IF THE CHARACTER IS NOT THE A ATTRIBUTE CHARACTER
* NO ACTION IS TAKEN ECCEPT THE AT.FLG IS RESET
*
AT.INT INC AT.FLG
    LDAA #1
    RTS
AT.HAN CMPB #FLASH
    BNE AT.HA1 IS IT FLASH
    INC FL.FLG
    BRA AT.HAE
AT.HA1 CMPB #NORMAL
    BNE AT.HAE
    CLR FL.FLG CLEAR THE FLASH FLAG
```

```
AT.HAE CLR AT.FLG
CLR.ES CLR ES.FLG
 RTS
*
* SET CURSOR ON OR OFF 0=OFF 1=ON
*
 DSCT
CU.FLG RMB 1
 PSCT
CU.INT INC CU.FLG
 RTS
CU.HAN PSHB    *
 CMPB #'0
 BNE CU.HA1
* LDAB PRASTR  *
* ANDB #CRCFLG *
* STAB PRASTR  *
* CLR CR.FLG
 JSR DISCLC
 BRA CU.HA2
CU.HA1 CMPB #'1
 BNE CU.HA2
* LDAB PRASTR  *
* ORAB #CR.FLG *
* STAB PRASTR  *
 JSR DISSTC
* INC CR.FLG
CU.HA2 CLR CU.FLG
 CLR ES.FLG
 PULB          *
 RTS
MON.MD INC MN.FLG
 CLR ES.FLG
 RTS
CAN.MD CLR MN.FLG
 CLR ES.FLG
 RTS
 END
*
 TITLE 'DISPLAY CHARACTER ROUTINE'
*
* THIS ROUTINE TAKES A CHARACTER IN B AND TEST'S THE FLASH BIT
* IT ALSO DETECT END OF LINE AND IF THE AUTO CR-LF FLAG IS SET
* IT GOES TO THE NEXT LINE
*
* EXTERNAL SUBROUTINE DEFINITIONS
*
 LIST 1
* OPT REL,Z01,LEE=120
 NAME DISHAN
*
* EXTERNAL REFERENCES
*
 XDEF DS.HAN
*
* EXTERNAL SUBROUTINE REFERENCES
*
 XREF CURPOS,LCDWRT
*
* EXTERNAL DATA POSITION REFERENCES
*
 XREF FL.FLG,CURSOR
 XREFB ATCRLF,PRASTR
*
* EXTERNAL EQUATE REFERENCE
*
 XREF SCBFST,SCBFED,SCBFHF,LCDMD1,LCDMD2,AUTOFF,DISCUR
 XREFB ROWMAX,COLMAX
*
* LOCAL EQUATES
```

```
*
FLHBIT EQU $80
*
* PROGRAM STARTS HERE
* B=CHARACTER
*
 PSCT
DS.HAN PSHX
* TST FL.FLG ARE WE IN FLASH MODE
* BEQ DS.HA1
* ORAB #FLHBIT SET THE FLASH ATTRIBUTE BIT
DS.HA1 LDX CURSOR
 STAB 0,X
 CPX #SCBFHF
 BHS DS.HA2
 LDX #LCDMD1
 INX
 BRA DS.HA3
DS.HA2 LDX #LCDMD2
 INX
DS.HA3 JSR LCDWRT
 JSR CURPOS GET THE CURRENT ROW AND COLUNM NUMBER
 CMPB #COLMAX
 BLO DS.HA4 IF AT THE END OF THE LINE
 JSR DISCUR
 BRA DS.HAE
* LDAB PRASTR *
* ANDB #ATCRLF *
* TST ATCRLF ARE WE IN AUTO CR-LF MODE
* BEQ DS.HA3
* CMPA #ROWMAX ARE WE AT THE LAST ROW
* BNE DS.HA2
DS.HA4 LDX CURSOR
 INX
* CPX #SCBFED+1
* BLO DS.HAE
* LDX #SCBFST
 STX CURSOR PUT THE NEW CURSOR AWAY
DS.HAE PULX
 RTS
 END
* OPT REL,Z01,LLE=120
 TITLE 'QUEUE HANDLER'
 NAME QUEHAN
 LIST 1
*
* THIS SECTION WILL HANDLE THE QUE READING AND WRITING FROM THE QUE
*
* EXTERNAL SUBROUTINE DEFINITIONS
*
 XDEF IN.QUE,WR.QUE,RD.QUE
*
* EXTERNAL DATA STORAGE DEFINITIONS
*
 XDEF QUETOP,QUEBEG,QUEEND,QUEROM
*
* EXTERNAL EQUATES DEFINITION
*
* LOCAL EQUATE
*
QUEEMT EQU 60
QUEDOF EQU QUEEMT/5
QUEDON EQU QUEEMT/2
*
* LOCAL STORAGE AREA
*
 DSCT
QUETOP RMB 60
QUEBOT EQU *-1
QUEBEG RMB 2
```

```
QUEEND RMB 2
QUEROM RMB 2
*
 XREF SENCHR,ENRVIN,DSRVIN
 XREFB XO.FLG,DTSTBT,XON,PRASTR
 XREFB PORT1
*
 PSCT
*
* INITIALIZE THE QUE VARIBLES
*
IN.QUE PSHX
 LDX #QUETOP
 STX QUEBEG
 STX QUEEND
 LDX #QUEEMT
 STX QUEROM
 PULX
 RTS
*
* WRITE TO THE QUE
* ENTERS B=CHARACTER
* EXITS A=00 FOR SUCCESS
*       01 FOR SUCCESS BUT REACH MINIMUM ROOM
*       10 FOR FAILURE
*
WRFAIL EQU 2
WR.QUE PSHB
 PSHX
 LDAA #WRFAIL
 LDX QUEROM IS THERE ANY ROOM
 BEQ WR.EXT
 LDX QUEEND
 STAB X STORE THE DATA
 INX SEE IF AT WE OUR WITS ENDS
 CPX #QUEBOT+1
 BNE WR.QU1
 LDX #QUETOP
WR.QU1 STX QUEEND
 DECA WE HAVE SUCCESS SO SET IT TO
 LDX QUEROM DECREMENT ROOM
 DEX
 CPX #QUEDOF
 BEQ WR.EXT
 DECA
WR.EXT STX QUEROM
 PULX
 PULB
 RTS
*
* THIS READ ROUTINE WILL GET THE CHARACTER OUT OF THE QUE AT
* QUE BEG AND DEC IT IF NOT AT ZERO
*
RD.QUE PSHX
 LDX QUEROM FIND OUT IF THERE IS ANY ROOM
 CPX #QUEEMT
 BEQ RD.EXT
 LDX QUEBEG GET THE POINTER TO CHARACTER TO BE
 LDAB X GET THE CHARACTER
 INX MAKE UP A NEW POINTER
 CPX #QUEBOT+1
 BNE RD.QU1
 LDX #QUETOP
RD.QU1 STX QUEBEG
 JSR DSRVIN
 LDX QUEROM
 INX
 CPX #QUEDON
 BNE RD.EX1
*BHI RD.EX1
```

```
*LDAA XO.FLG ARE WE IN X/DTR MODE
 LDAA PRASTR
 ANDA #XO.FLG
 BNE RD.XON
 LDAA #DTSTBT SET /DTR
 ORAA PORT1
 STAA PORT1
RD.EX1 STX QUEROM
 JSR ENRVIN
 LDAA #$FF
RD.EXT PULX
 RTS
RD.XON LDAA #XON SEND A XON
 JSR SENCHR
 BRA RD.EX1
 END
*
 TITLE 'ONE LINE RAM SEGMENTS'
 NAM RAMSCT
 LIST 1
*
* THIS SECTION WILL DEFINE THE RAM DATA LOCATIONS
*
* OPT REL,Z01,LLE=120
*
*
 XDEF SCBFST,SCBFED,CURSOR,FL.FLG,FLSHST,PRASTR,SL.FLG,DS.FLG,PR.FLG,ODEVPR
 XDEF XO.FLG,ATCRLF,ES.FLG,AT.FLG,PS.FLG,MN.FLG,STKSTR,CR.FLG
 XDEF BD.RAT,AUXSBF,HF.FLG,AUXSBE,SCBFHF,SCBLGT,SCBLG1,SCBLG2
 XDEF RAMSTR,RAMEND,HFCFLG,CRCFLG,PRCFLG,XOCFLG
*Q
* EXTERNAL VECTOR REFERENCES
*
 XREF SY.INT,DS.DRV
 XREF REVCHR
*
LINLGT EQU  40
 DSCT
SCBFEQ EQU *
SCBFST RMB 160
SCBFED EQU *-1
SCBFHF EQU SCBFEQ+80
SCBLGT EQU  SCBFED-SCBFST
SCBLG1 EQU  SCBFED-SCBFST-LINLGT
SCBLG2 EQU  SCBFST+LINLGT

AUXSBF RMB 0
AUXSBE EQU *-1
CURSOR RMB 2
FL.FLG RMB 1
FLSHST RMB 1
BD.RAT RMB 1
*
* SWITCH FLAGS
*
PRASTR RMB 1
SL.FLG EQU $80 SLAVE TERMIAL
DS.FLG EQU $40 DISPLAY FLAG
HF.FLG EQU $02 HALF/FULL DUPLEX FLAG
CR.FLG EQU $01 CURSOR STATUS FLAG ROUTINE
PR.FLG EQU $20 PARITY FLAG
ODEVPR EQU $10 ODD EVEN FLAG
XO.FLG EQU $08 DTR/XON-XOFF
ATCRLF EQU $04 AUTO CARRIAGE RETURN LINE FEED
HFCFLG EQU HF.FLG!X$FF
CRCFLG EQU CR.FLG!X$FF
PRCFLG EQU PR.FLG!X$FF
XOCFLG EQU XO.FLG!X$FF
*
*ROUTINE FLAGS
```

```
*
ES.FLG RMB 1 ESCAPE IN PROGRESS FLAG
AT.FLG RMB 1 DISPLAY ATTRIBUTE CHANGE IN PROGRESS
PS.FLG RMB 1 POSITION CURSOR IN PROGRESS
MN.FLG RMB 1 MONITOR MODE IN PROGRESS
*
* QUE DATA AREA
*
*QUETOP RMB 255
*QUEBOT EQU *-1
*QUEBEG RMB 2
*QUEEND RMB 2
*QUECNT RMB 1
*
RAMSTR EQU $100
RAMEND EQU $2FF
STKSTR EQU $2FF
* ASCT
* ORG $FFEE
*TRAP FDB SY.INT
*SERINT FDB RV.DRV
*TIMOVR FDB SY.INT
*OUTCAP FDB DS.DRV
*INPCAP FDB SY.INT
*IRQ FDB SY.INT
*SWI FDB SY.INT
*NMI FDB SY.INT
*RESET FDB SY.INT
 END
 TITLE 'TERMINAL HANDLER'
* TERMINAL HANDLER FOR THE 4 LINE TERMINAL MODE OF OPERATION
* UPON RESET OF THE PROCESSOR THE 4 LINER PROGRAMMING SWITCH
* STATE IS LOADED INTO THE PROCESSOR AND IF THE TERMINAL MODE
* IS SELECETED THEN THIS ROUTINE IS INVOKED AND WILL NEVER EXIT
* UNTIL THE PROCESSOR IS RESET
* THE FIRST OPERATION IS TO SET THE COMMUNICATION PARAMETERS
* CLEAR THE SCREEN AND STATUS FLAGS
*
* OPT REL,Z01,LLE=120
 NAM TERHAN
 LIST 1
*
 XDEF TR.INT,OUTCHR
 XDEF SWTCNT
*
*EXTERNAL CONSTANTS AND DATA LOCATIONS
*
 XREF ES.FLG
 XREF FL.FLG,MN.FLG,PR.FLG,CR.FLG
 XREF HF.FLG,CURSOR,SWSLCL,SWSLST
 XREFB PORT1,PORT4,TCSR,DPSWTH,ESC
 XREF PRASTR
*
*EXTERNAL ROUTINES
*
 XREF CN.HAN,DS.HAN,ES.INT,ES.HAN,RD.QUE
 XREF CLR.SC,IN.QUE,DS.INT,ENRVIN,SR.INT,SET.SC,WAIT,LCDINT
*
*EXTERNAL EQUATES ROUTINES
*
 XREFB OLVL,DTSTBT,SWIMSK
*
* LOCAL EQUATES
*
SWTCNT EQU 6
RSOLVL EQU $FE CLEAR OLVL
WAITTM EQU $32*$FF
*
* DATA COMMON FOR SWITCH PARAMETER
*
* PROGRAM STARTS HERE WITH TR.INT INITIALIZATION ROUTINE
```

```
*
 PSCT
TR.INT JSR  LCDINT
 JSR CLR.SC
 JSR IN.QUE
 CLR ES.FLG
 CLR FL.FLG
 LDAA TCSR
 ORAA #OLVL
 ANDA #RSOLVL
TR.IN3 STAA TCSR
 CLR MN.FLG
 JSR SR.INT
* JSR DS.INT INTIALIZE THE DISPLAY DRIVER
* JSR SET.SC
* CLI
* LDX #WAITTM
* JSR WAIT
* SEI
* JSR CLR.SC
 JSR ENRVIN ENABLE REV. INTERRPUPTS
 CLI
 RTS
*
*
* THIS IS THE MAIN TERMINAL PROGRAM IT WILL RUN IN FOREGROUND
* IT WILL READ THE QUE AND DEPENDING ON THE STATUS OR CHARACTER
* IT WILL VECTOR OF TO THE APPROPIATE ROUTINE
*
*
*TR.MAN JSR RD.QUE GET A CHARACTER FROM THE QUE
* BEQ TR.MAN
*TR.MAN BRA TR.MAN IF Z=1 THEN QUE IS EMPTY
*
* QUE IS NOT EMPTY WE GOT A CHARACTER
* CHARACTER IS IN B
*
*TR.MAN
OUTCHR CMPB #ESC
 BNE TR.MA1
 JSR ES.INT
 BRA TR.EXT
TR.MA1 TST ES.FLG IS THE ES.FLG SET
 BEQ TR.MA2
 JSR ES.HAN IF SET THIS CHARACTER IS PART OF A ESCAPE SEQUENCE
 BRA TR.EXT
TR.MA2 CMPB #$20 IS IT A CONTROL CHARACTER?
 BGE TR.MA3
 JSR CN.HAN YES IT IS A CONTROL CHARACTER
 BRA TR.EXT
TR.MA3 JSR DS.HAN
TR.EXT RTS
 END
 TITLE     'LCD HANDLER '
*******************************************************************
*
*
* LCD HANDLER -- THESE ARE THE ROUTINES THAT HANDLE THE LCD DISPLAY
*
*
 NAME LCD
 LIST 1
 XREF CURSOR,SCBFST,SCBFED,SCBFHF
 XDEF LCDINT,LCDWRT,DISBUF,DISCUR,DISCLR,DISSTC,DISCLC
 XDEF LCDMD1,LCDMD2,FNDCUR
LCDMD1 EQU $2000
LCDMD2 EQU $2004
 PSCT
LCDINT LDX #LCDMD1
```

```
LCDLOP  LDAA  #$30
        STAA  0,X
        LDD   #$3FF
LCDIN1  SUBD  #1
        BNE   LCDIN1
        LDAA  #$30
        STAA  0,X
        LDAB  #$40
LCDIN2  DECB
        BNE   LCDIN2
        STAA  0,X
        BSR   LCDWT
        LDAA  #$38
        STAA  0,X
        BSR   LCDWT
        LDAA  #$08
        STAA  0,X
        BSR   LCDWT
        LDAA  #$01
        STAA  0,X
        BSR   LCDWT
        LDAA  #$06
        STAA  0,X
        BSR   LCDWT
        LDAA  #$0C
        STAA  0,X
        BSR   LCDWT
        LDAA  #$14
        STAA  0,X
        BSR   LCDWT
        LDAA  #$80
        STAA  0,X
        BSR   LCDWT
        CPX   #LCDMD2
        BEQ   LCDINE
        LDAB  #04
        ABX
        BRA   LCDLOP
LCDINE  RTS
**********************************************************************
*
*DISBUF -- THIS PROGRAM WILL TAKE THE SCREEN BUFFER AND DISPLAY IT THE
* LCD MODULE
*
DISBUF  PSHX
        PSHA
        LDAA  #01
        LDX   #LCDMD1
        BSR   LCDWT
        STAA  0,X
        LDX   #LCDMD2
        BSR   LCDWT
        STAA  0,X
        LDX   #SCBFST
DISLOP  LDAA  0,X
        PSHX
        CPX   #SCBFHF
        BHS   DISLO1
        LDX   #LCDMD1
        BSR   LCDWT
        STAA  1,X
        BRA   DISLO2
DISLO1  LDX   #LCDMD2
        BSR   LCDWT
        STAA  1,X
DISLO2  PULX
        INX
        CPX   #SCBFED+1
        BNE   DISLOP
        PULA
```

```
        PULX
        RTS
LCDWT   PSHB
LCDWT1  LDAB 0,X
        ANDB #$80
        BNE  LCDWT1
        PULB
        RTS
****************************************************************************
*
* DISCUR -- THIS ROUTINE WILL WRITE TO THE DISPLAY A NEW CURSOR POSITON
*
*
DISCUR  PSHX
        PSHA
        PSHB
        JSR  FNDCUR     GET THE DISCRETE CURSOR POSITION AND ADDRESS
        BSR  LCDWT
        CMPB #$28
        BLO  DISCU3
        ADDB #$18
DISCU3  ORAB #$80
        STAB 0,X
        PULB
        PULA
        PULX
        RTS
****************************************************************************
*
* DISCLR- CLEARS THE LCD DISPLAY
*
DISCLR  PSHA
        LDAA #01
        LDX  #LCDMD1
        BSR  LCDWT
        STAA 0,X
        LDX  #LCDMD2
        JSR  LCDWT
        STAA 0,X
        PULA
        RTS
****************************************************************************
*
*DISCLC--CLEAR THE CURSOR OFF THE SCREEN
*
DISCLC  PSHA
        JSR  FNDCUR
        LDAA #$0C
        BSR  LCDWT
        STAA 0,X
        PULA
        RTS
****************************************************************************
*
*DISSTC--SET THE CURSOR ON THE DISPLAY
*
DISSTC  PSHA
        JSR  FNDCUR
        LDAA #$0F
        BSR  LCDWT
        STAA 0,X
        PULA
        RTS
****************************************************************************
*
* LCDWRT-WRITE THE CONTENTS OF B TO WHERE X POINTS AFTER WAITING
*
LCDWRT  DEX
BSR     LCDWT
INX
```

```
   STAB 0,X
   RTS
***********************************************************************
*
* FNDCUR --THIS ROUTINE WILL LOCATE I=ON WHAT ADDRESS IS THE CURSOR
* X=ADDRESS TO THTE MODULE
* B=DISCRETE CURSOR POSITION
FNDCUR
   LDD   CURSOR
   SUBD  #SCBFST
   LDX   CURSOR      GET THE NEW CURSOR
   CPX   #SCBFHF
     BLO     FNDCU1
   LDD   CURSOR
   SUBD  #SCBFHF
   LDX   #LCDMD2
   BRA   FNDCU2
FNDCU1 LDX   #LCDMD1
FNDCU2 RTS
   END
   TITLE 'SYSTEM INIT FOR THE LCD DISPLAY'
***********************************************************************
*
*
   LIST 1
   NAME SYSINT1
   XDEF SY.RIN,SY.INT
   XREF TR.INT,SR.INT,STKSTR,REVCHR,KY.INT,MAIN
   XREFB     P1DDRI,P1DDR
   PSCT

; THIS INTIALATION IS USED WHEN USED WITH LILBUG
SY.RIN LDX   #TABLE
   STX   $FE
   BRA   SY.INT
;
; PROGRAM INTERRUPT VECTOR
;
NMI    EQU   $F803
TABLE  FDB   REVCHR
   FDB   NMI
   FDB   NMI
   FDB   NMI
   FDB   $F821
   FDB   $F821      LIL BUG SWI
   FDB   $F803
;
; OUR SYS INT
;
SY.INT LDS #STKSTR   INITIALIZE THE STACK POINTER
   JSR   SR.INT
   LDAA  #P1DDRI
   STAA  P1DDR
   JSR   KY.INT
   JSR   TR.INT
   JMP   MAIN
   END
   TITLE 'KEY BOARD HANDLER'
***********************************************************************
*
* KEYHAN-THIS SECTION WILL HANDLE THE PUSH BUTTONS ON THE QESTION BOX
*
* IT IS CALLED AND IT READ THE BUTTONS AND IF THERE IS A CLOSURE
* THEN IT WILL SET UP A TIMER AND THEN WAITS THERE UNTIL IT REACHES
* 0 THEN IT IS READ AGAIN IF THE KEYS ARE THE SAME THEN THE BUTTON
* NUMBER WILL BE SENT BACK IN B
*
   NAME KEYHAN
   LIST 1
   XREFB     COMFLG
```

```
    XREFB     TCSR,PORT1,P1DDR,OTCPRG,TIMREG
    XDEF KY.INT,KY.HAN
    PSCT
KEYDDR EQU  0
KEY    EQU  $0F
DEBNDL EQU  $07FF
KY.INT LDAA #KEYDDR
  STAA P1DDR
  RTS
*
KY.HAN PSHA
KY.LOP BSR KEYSCN
  BEQ  KY.LOP
  PSHB
  BSR  SETTIM
KEYHA1 BSR   KEYSCN
  BEQ  KEYHA1
  PULA
  CBA
  BNE  KY.LOP
  TAB
  PULA
  RTS
KEYSCN LDAB PORT1
  COMB
  ANDB #KEY
  BEQ KEYSCN
  RTS
SETTIM PSHB
  PSHA
  LDD #DEBNDL
SETTI1 SUBD #1
  BNE  SETTI1
  PULA
  PULB
  RTS
  END
        NAME    HEADER
*
        LIST    1
*
        XDEF    HEADER,DISCLM,SPCHN1,SPCHN2,SPCHN3
        XREF    PRTCHR,PRTSTR,ANS1,NO,YES,IDNO,NOANS,BSTRNG
        XREF    W55,W57
        XREF    W62,W63,W64,W67,W68,W69
        XREF    Q54,Q55,Q57,Q58,Q59
        XREF    Q60,Q61,Q62,Q63,Q64,Q67,Q68,Q69
        XREF    Q70,Q71,Q72,Q73,Q74,Q75,Q76,Q77
        XREF    W55Y,W58Y,W59Y
        XREF    W60Y,W61Y,W62Y,W63Y,W64Y,W67Y,W67N,W68Y,W68N,W69Y,W69N
        XREF    W70Y,W70N,W71Y,W71N,W72Y,W72N,W73Y,W74Y,W75Y,W76Y,W77Y
*
        PSCT
*
FF:     FCB     12
LINE1:  FCC     /$$/
        FCC     /CCSQI HealthQuiz results :$$/
        FCC     /(areas with a line need to be completed)$$/
        FCC     /PATIENT NAME: _____ DATE:$$
LINE2:  FCC     /BIRTHDATE: /____
        FCB     0
LINE3:  FCC     /$$/
        FCC     /UNIT NUMBER:  CCSQI-00001    VALID UNTIL -- JUNE 30, 1988 --$
        FCC     /PERSON ADMINISTERING: _____$$/
LINE4:  FCC     /PHYSICIAN: _____$$/
        FCC     /SCHEDULED OPERATION _____$$$/
        FCB     0
*
*This routine prints the above header.
```

```
*
*****************************************SUBROUTINE HEADER
*
HEADER:  PSHX
         PSH B
         LDA B    FF                *Send a form feed to align the paper
         JSR      PRTCHR
         LDX      #LINE1            *Print out the header
         JSR      PRTSTR
         LDX      #BSTRNG
         JSR      PRTSTR
         LDX      #LINE3
         JSR      PRTSTR
         PUL B
         PULX
         RTS
*
*
DISC1:   FCC  /$ Based on the response of the patient to the CCSQI$/
         FCC  /HealthQuiz, the following laboratory tests would be indicated
         FCC  /preoperatively based on the literature cited below** which$/
         FCC  /indicates the likelihood of the test finding disease or$/
         FCC  /optimizing patient care, versus the result of that test $/
         FCC  /leading to a false positive tests and subsequent hazard$/
         FCC  /to the Patient. This Guideline is valid to June 30, 1988.$/
         FCB  0
*
DISC2:   FCC  /$ These responses to the questionnaire are to be an aid to$/
         FCC  /the physician and and should NOT be considered as a substitut
         FCC  /to the physician's history, physical, and any test(s) the$/
         FCC  /physician deem(s) clinically indicated. Such routine screenin
         FCC  /tests as stool guiac or hemoccult, Pap smears, etcetera are$/
         FCC  /not suggested as indicated. Such may be indicated based on th
         FCC  /physician's judgement of them; the indicated laboratory tests
         FCC  /above are only tests thought appropriate for the perioperativ
         FCC  /care of the patient.$$/
         FCB  0
*
DISC3:   FCC  /$** Based on the response of the patient to the CCSQI$/
         FCC  /HealthQuiz, the following laboratory tests would be indicated
         FCC  /preoperatively considering the likelihood of the test finding
         FCC  /disease or optimizing patient care, versus the result of that
         FCC  /test leading to a false positive tests and subsequent hazard$,
         FCC  /to the Patient.$/
         FCC  / This guideline is valid to JUNE 30, 1988, and is based on
         FCC  /literature and reviews published by Roizen in Miller's$
         FCC  /ANESTHESIA, 1986 edition; by Mckee and Scott in ANNALS OF THE
         FCC  /ROYAL COLLEGE OF SURGEONS, 1987; by Robins and Rose in MEDICA
         FCC  /CLINICS OF NORTH AMERICA, 1979 and 1986; by Blery et al in$
         FCC  /LANCET, January 1986; by numerous authors in ANNALS OF$
         FCC  /INTERNAL MEDICINE (May 1985 through December 1986). Similar$
         FCC  /guidelines for radiology studies have been endorsed by an$
         FCC  /FDA panel (1984), the American College of Surgeons, and$
         FCC  /American College of Physicians (not an all inclusive list).$
         FCC  /Guidelines for all tests are similar to those presented at$
         FCC  /an NIH consensus panel on Anesthesia for Dental Patients$,
         FCC  /endorsed in the Blue Cross-Blue Shield Medical Necessity$,
         FCC  /Guidelines by the American College of Physicians (and$,
         FCC  /published in ANNALS OF INTERNAL MEDICINE), and by the$,
         FCC  /American Society of Anesthesiology.$/
         FCB  0
*
*****************************************SUBROUTINE DISCLM
* There are three different sections which this routine may output the optio
* is selected by passing the integer 1-3 in ACC-B.
*
DISOPT:  FDB   DISC1,DISC2,DISC3
*
DISCLM:  PSHX
         LDX   #DISOPT
         DEC B                      *Fix the offset
```

```
            LSL    B                      *Multiply by two
            ABX                           *Add in offset
            LDX    0,X                    *Get start address of section
            JSR    PRTSTR                 *Print section.
            PULX
            RTS
*
CRLF:       FCC    /$/
            FCB    0
LINE:       FCC    /$_____$$/
            FCB    0
*
*
*This routine handles all of the special questions, those which require
*additional output. If the answer to the question is YES or NOT SURE the
*string associated with that question is printed. There are three entry
*points SPCHN1 is for printing the general health statements while SPCHN2
*is used to print the additional questions. SPCHN3 is used to print statment:
*related to Anesthesia care.
*
*****************************************SUBROUTINE SPCHN1
*
SPCHN1:     PSH    A
            PSH    B
            PSHX
            LDX    #STMT
            CLR    A
            STA    A    LFLAG
            JMP    NXTTST
*
*****************************************SUBROUTINE SPCHN2
*
SPCHN2:     PSH    A
            PSH    B
            PSHX
            LDA    A    #1              *Enable the line flag
            STA    A    LFLAG
            LDX    #SPCQST              *Get address of special questions
            JMP    NXTTST
*
*****************************************SUBROUTINE SPCHN3
*
SPCHN3:     PSH    A
            PSH    B
            PSHX
            LDX    #STMT1
            CLR    A
            STA    A    LFLAG
            JMP    NXTTST

*
*Process the pairs of values to check if any of the additional questions
*need to be printed. The array SPCQST contains a pointer to the question
*followed by a pointer to the additional question. If the answer to the
*question is a YES print the first additional question, if the answer is
*NO print the second string if the answer is NOT SURE print the third string
*
            DSCT
*
LFLAG:      RMB    1
TSTPTR:     RMB    2
*
            PSCT
NPRT:       FCB    0
DONE        FCB    0
*
*Data Format:    <Question> <YES string> <NO string> <NOT SURE string>
*
SPCQST:     FDB    Q54,W55,NPRT,W55,Q57,W57,NPRT,W57
            FDB    Q62,W62,NPRT,W62,Q63,W63,NPRT,W63,Q64,W64,NPRT,W64
```

```
        FDB     Q67,W67,NPRT,W67,Q68,W68,NPRT,W68,Q69,W69,NPRT,W69
        FDB     DONE
*                          *                      *
STMT:   FDB     Q67,W67Y,W67N,W67N,Q68,W68Y,W68N,W68N,Q69,W69Y,W69N,W69N
        FDB     Q70,W70Y,W70N,W70N,Q71,W71Y,W71N,W71N,Q72,W72Y,W72N,W72N
        FDB     DONE
*
STMT1:  FDB     Q55,W55Y,NPRT,NPRT
        FDB     Q58,W58Y,NPRT,NPRT,Q59,W59Y,NPRT,NPRT,Q60,W60Y,NPRT,NPRT
        FDB     Q61,W61Y,NPRT,NPRT,Q62,W62Y,NPRT,NPRT,Q63,W63Y,NPRT,NPRT
        FDB     Q64,W64Y,NPRT,NPRT
        FDB     Q73,W73Y,NPRT,NPRT,Q74,W74Y,NPRT,NPRT,Q75,W75Y,NPRT,NPRT
        FDB     Q76,W76Y,NPRT,NPRT,Q77,W77Y,NPRT,NPRT
        FDB     DONE
*
*
NXTTST: STX     TSTPTR          *Save pointer to structure
        PSHX                    *Save copy of pointer on stack
        LDX     0,X             *Get address of question
        LDA B   0,X             *Load the offset index
        BEQ     OUT             *Done? branch to end
        LDX     #ANS1           *Get address of answer array
        ABX                     *Add offset to base address
        LDA B   0,X             *Get a copy of the answer
        CMP B   NOANS           *No answer don't print
        BEQ     NOPRNT
        CMP B   NO              *If the answer is NO add 2
        BNE     OV1
        LDA B   #2
        PULX
        ABX
        PSHX
        BRA     OV2
*
OV1:    CMP B   IDNO            *If the answer is NOT SURE add 4
        BNE     OV2
        LDA B   #4
        PULX
        ABX
        PSHX
*
OV2:    PULX                    *Get pointer address
        PSHX
        INX                     *Add two to the pointer
        INX
        LDX     0,X             *Load the address of the string
        LDA B   0,X             *Print the string?
        BEQ     NOPRNT
        JSR     PRTSTR          *Print the string
        TST     LFLAG           *Line flag set? print the line.
        BEQ     NOPRNT
        LDX     #LINE
        JSR     PRTSTR
*
*Add 8 to the current pointer to advance to the next test trio and branch
*back to the top to process the pair.
*
NOPRNT: PULX                    *Clean up stack
        LDA B   #8
        LDX     TSTPTR
        ABX                     *Add offset and get next structure
        BRA     NXTTST
*
OUT:    PULX                    *Clean up the stack
        PULX                    *Restore environment
        PUL B
        PUL A
        RTS
*
        END
```

```
            NAM     LABTESTS
            LIST    1                          *Use 6801 Instruction Set
*
            XDEF    IARRAY,QARRAY,QCOUNT,TARRAY,TCOUNT
            XDEF    W55,W57
            XDEF    W62,W63,W64,W67,W68,W69
            XDEF    Q54,Q55,Q57,Q58,Q59
            XDEF    Q60,Q61,Q62,Q63,Q64,Q67,Q68,Q69
            XDEF    Q70,Q71,Q72,Q73,Q74,Q75,Q76,Q77
            XDEF    W55Y,W58Y,W59Y
            XDEF    W60Y,W61Y,W62Y,W63Y,W64Y,W67Y,W67N,W68Y,W68N,W69Y,W69N
            XDEF    W70Y,W70N,W71Y,W71N,W72Y,W72N,W73Y,W74Y,W75Y,W76Y,W77Y
*
BRANCH: EQU     0                          *Indicate 3 pointers for branch
NBRNCH: EQU     1                          *Indicate 1 pointer (NO BRANCH)
*
            PSCT
*
INTRO1: FCC     /Please answer the following questions.$/
        FCC     /To proceed, press your answer and then$/
        FCC     /the next question button.$/
        FCC     /Are you ready to continue?/
        FCB     0
INTRO2: FCC     /Your answers to the following questions$/
        FCC     /will be used to assist your doctor in$/
        FCC     /taking care of you.$/
        FCC     /Are you ready to continue?/
        FCB     0
INTRO3: FCC     /If you make a mistake you can change$/
        FCC     /your answer until you press the next$/
        FCC     /question button. Try it - Press yes then$/
        FCC     /no then yes then next question./
        FCB     0
INTRO4: FCC     /If you make a mistake and have already$/
        FCC     /pressed the next question button. Please$/
        FCC     /return this machine so it may be reset.$/
        FCC     /Are you ready to continue?/
        FCB     0
INTRO5: FCC     /Take your time and answer each question$/
        FCC     /to the best of your knowledge.$/
        FCC     /There are 75 questions.$/
        FCC     /Are you ready to begin?/
        FCB     0
*
IARRAY: FDB     INTRO1,INTRO2,INTRO3,INTRO4,INTRO5,QEND
*
*The following data is a list of the questions which will be asked to
*each person using the device. If there is additional output in the form
*of another question or a statement associated with the question that data
*will appear after the question. The format of each question is as follows:
*
*<label>    <index><flag><class>
*           <string>
*           <branch flag>
*           <yes,not sure ptr> [<no ptr>]
*[<label>   <string>]
*[<label>   <yes string>]
*[<label>   <no string>]
*
*label : The label is the reference to the question entry. Lables begin with
*         either a Q for question of W for associated string. The number is
*         the question number. If the label is an associated string (begins
*         with a W) the last character will be either a Y for the yes response
*         a N for the no response or a blank indicating a question to be
*         printed for additional information.
*
*index : This value is the question number and the offset into the answer
*         array.
```

```
*
*flag  : This is a general purpose flag an currently has 3 possible values.
*              0 is the default (no meaning)
*              1 indicates the question has an associated string
*              2 indicates the question should only be asked to females
*
*class : This value classifies the question into one of the three classes
*              1 questions for lab tests
*              2 questions for anesthesia
*              3 questions for general health
*
*string: The string is the text of the question. Each line may be no longer
*        than 40 characters (excluding the $ symbol). Only 4 lines are
*        allowed and the fourth line may only be 30 characters. The $ symbol
*        is used to indicate a CRLF to the output routine and is not displaye
*
*branch flag: This flag is used to indicate weather the paitents answer is t
*        be used for a conditional branch. 0 indicates there are two possibl
*        locations to branch to one for YES and NOT SURE and the other for
*        NO. 1 indicates no conditional branch (only one pointer).
*
*                 /----------1----------2----------3----------4/
*
Q01:    FCB     1,0,1       ****** LAB TEST QUESTION ******
*
        FCC     /Have you taken Asprin, Excedrin, Anacin,$/
        FCC     /Bufferin, Alka Seltzer or any similar$/
        FCC     /medications in the last week?/
        FCB     0,NBRNCH
        FDB     Q02
Q02:    FCB     2,0,1       ****** LAB TEST QUESTION ******
*
        FCC     /Do you currently take drugs to suppress$/
        FCC     /your immune system such as cyclosporin,$/
        FCC     /azathioprine, imuran, cyclophosphamide,$/
        FCC     /or 6-mercaptopurine?/
        FCB     0,NBRNCH
        FDB     Q03
Q03:    FCB     3,0,1       ****** LAB TEST QUESTION ******
*
        FCC     /Have you ever had cancer or been treated$/
        FCC     /for cancer with chemotherapy or x-ray$/
        FCC     /radiation therapy?/
        FCB     0,NBRNCH
        FDB     Q04
Q04:    FCB     4,0,1       ****** LAB TEST QUESTION ******
*
        FCC     /Do you have or have you had problems$/
        FCC     /with your blood such as anemia,$/
        FCC     /leukemia, or sickle cell disease?/
        FCB     0,NBRNCH
        FDB     Q05
Q05:    FCB     5,0,1       ****** LAB TEST QUESTION ******
*
        FCC     /Have you ever had a bleeding problem or$/
        FCC     /a blood clotting problem?/
        FCB     0,NBRNCH
        FDB     Q06
Q06:    FCB     6,0,1       ****** LAB TEST QUESTION ******
*
        FCC     /Are your stools ever bloody or black$/
        FCC     /and tarry?/
        FCB     0,NBRNCH
        FDB     Q07
Q07:    FCB     7,0,1       ****** LAB TEST QUESTION ******
*
        FCC     /Have you vomited blood or material that$/
        FCC     /looks like coffee grounds in the last$/
        FCC     /6 months?/
        FCB     0,NBRNCH
        FDB     Q08
```

```
Q08:    FCB    8,0,1       ****** LAB TEST QUESTION ******
  *
        FCC    /Did you receive a blood transfusion$/
        FCC    /within the last six months?/
        FCB    0,NBRNCH
        FDB    Q09
Q09:    FCB    9,0,1       ****** LAB TEST QUESTION ******
  *
        FCC    /Did you receive a blood transfusion$/
        FCC    /after 1979?/
        FCB    0,NBRNCH
        FDB    Q10
Q10:    FCB    10,0,1      ****** LAB TEST QUESTION ******
  *
        FCC    /Have you ever required a blood$/
        FCC    /transfusion for excessive bleeding?/
        FCB    0,NBRNCH
        FDB    Q11
Q11:    FCB    11,0,1      ****** LAB TEST QUESTION ******
  *
        FCC    /Have you lost more than 5% of your usual$/
        FCC    /body weight in the last year?/
        FCB    0,NBRNCH
        FDB    Q12
Q12:    FCB    12,0,3      *** GENERAL HEALTH QUESTION ***
  *
        FCC    /Has your appetite for food changed in$/
        FCC    /the last year?/
        FCB    0,NBRNCH
        FDB    Q13
Q13:    FCB    13,0,3      *** GENERAL HEALTH QUESTION ***
  *
        FCC    /Are you eating the same foods as you$/
        FCC    /were a year ago?/
        FCB    0,BRANCH
        FDB    Q14,Q18
Q14:    FCB    14,0,1      ****** LAB TEST QUESTION ******
  *
        FCC    /Have you ever smoked half a pack or more$/
        FCC    /cigarettes per day on a regular basis?/
        FCB    0,BRANCH
        FDB    Q15,Q18
Q15:    FCB    15,0,1      ****** LAB TEST QUESTION ******
  *
        FCC    /Have you smoked half a pack or more$/
        FCC    /cigarettes per day within the last$/
        FCC    /two weeks?/
        FCB    0,BRANCH
        FDB    Q18,Q16
Q16:    FCB    16,0,1      ****** LAB TEST QUESTION ******
  *
        FCC    /Have you quit smoking and continued$/
        FCC    /without cigarettes for 4 weeks?/
        FCB    0,BRANCH
        FDB    Q17,Q18
Q17:    FCB    17,0,1      ****** LAB TEST QUESTION ******
  *
        FCC    /Have you quit smoking and continued$/
        FCC    /without cigarettes for 5 years?/
        FCB    0,NBRNCH
        FDB    Q18
Q18:    FCB    18,0,1      ****** LAB TEST QUESTION ******
  *
        FCC    /Do you suffer from shortness of breath,$/
        FCC    /chest pain, emphysema, asthma, or$/
        FCC    /bronchitis?/
        FCB    0,NBRNCH
        FDB    Q19
```

```
Q19:    FCB     19,0,1      ****** LAB TEST QUESTION ******
*
        FCC     /Do you cough regulary or frequently?/
        FCB     0,NBRNCH
        FDB     Q20
Q20:    FCB     20,0,1      ****** LAB TEST QUESTION ******
*
        FCC     /Do you cough up sputum?/
        FCB     0,NBRNCH
        FDB     Q21
Q21:    FCB     21,0,1      ****** LAB TEST QUESTION ******
*
        FCC     /In the last month have you noticed a$/
        FCC     /change in the color or consistency of$/
        FCC     /the sputum?/
        FCB     0,NBRNCH
        FDB     Q22
Q22:    FCB     22,0,1      ****** LAB TEST QUESTION ******
*
        FCC     /In the last 4 weeks have you had a$/
        FCC     /fever, chills, cold, or flu?/
        FCB     0,NBRNCH
        FDB     Q23
Q23:    FCB     23,0,1      ****** LAB TEST QUESTION ******
*
        FCC     /Have you ever had a heart attack or been$/
        FCC     /treated for a possible heart attack?/
        FCB     0,NBRNCH
        FDB     Q24
Q24:    FCB     24,0,1      ****** LAB TEST QUESTION ******
*
        FCC     /Do you have heart problems such as$/
        FCC     /skipped heart beats, angina or$/
        FCC     /chest pain?/
        FCB     0,NBRNCH
        FDB     Q25
Q25:    FCB     25,0,1      ****** LAB TEST QUESTION ******
*
        FCC     /Do you currently take quinidine, inderal$/
        FCC     /diltiazem, verapramil, nifedipine,$/
        FCC     /nitroglycerine, or propranolol, digoxin$/
        FCC     /lanoxin, digitoxin or digitalis?/
        FCB     0,NBRNCH
        FDB     Q26
Q26:    FCB     26,0,1      ****** LAB TEST QUESTION ******
*
        FCC     /Do you currently take any medication$/
        FCC     /for high blood pressure?/
        FCB     0,NBRNCH
        FDB     Q27
Q27:    FCB     27,0,1      ****** LAB TEST QUESTION ******
*
        FCC     /Have you been told by your doctor to$/
        FCC     /exercise and diet to control high blood$/
        FCC     /pressure?/
        FCB     0,NBRNCH
        FDB     Q28
Q28:    FCB     28,0,1      ****** LAB TEST QUESTION ******
*
        FCC     /Have you ever woken up at night and felt$/
        FCC     /short of breath or been told you have$/
        FCC     /rheumatic fever?/
        FCB     0,NBRNCH
        FDB     Q29
Q29:    FCB     29,0,1      ****** LAB TEST QUESTION ******
*
        FCC     /Do you become short of breath after$/
        FCC     /climbing one flight of stairs or after$/
        FCC     /walking a short distance?/
        FCB     0,NBRNCH
        FDB     Q30
```

```
Q30:    FCB     30,0,3     *** GENERAL HEALTH QUESTION ***
*
        FCC     /Are you able to walk up stairs at the$/
        FCC     /same rate you could 5 years ago?/
        FCB     0,NBRNCH
        FDB     Q31
Q31:    FCB     31,0,1     ****** LAB TEST QUESTION ******
*
        FCC     /Do you currently take water pills or$/
        FCC     /diuretics?/
        FCB     0,NBRNCH
        FDB     Q32
Q32:    FCB     32,0,1     ****** LAB TEST QUESTION ******
*
        FCC     /Do you currently take potassium pills$/
        FCC     /or powder?/
        FCB     0,NBRNCH
        FDB     Q33
Q33:    FCB     33,0,3     *** GENERAL HEALTH QUESTION ***
*
        FCC     /Have your bowel or bladder functions$/
        FCC     /changed in the last year?/
        FCB     0,NBRNCH
        FDB     Q34
Q34:    FCB     34,0,1     ****** LAB TEST QUESTION ******
*
        FCC     /Do you have any problems with your$/
        FCC     /kidneys?/
        FCB     0,NBRNCH
        FDB     Q35
Q35:    FCB     35,0,1     ****** LAB TEST QUESTION ******
*
        FCC     /Have you ever been told you have$/
        FCC     /diabetes or sugar diabetes?/
        FCB     0,NBRNCH
        FDB     Q36
Q36:    FCB     36,0,1     ****** LAB TEST QUESTION ******
*
        FCC     /Do you often wake up to urinate more$/
        FCC     /than once a night?/
        FCB     0,NBRNCH
        FDB     Q37
Q37:    FCB     37,0,3     *** GENERAL HEALTH QUESTION ***
*
        FCC     /Have you engaged in sex (intercourse)$/
        FCC     /within the last 2 weeks?/
        FCB     0,NBRNCH
        FDB     Q38
Q38:    FCB     38,0,3     *** GENERAL HEALTH QUESTION ***
*
        FCC     /Is your level of sexual desire and$/
        FCC     /activity normal for you?/
        FCB     0,NBRNCH
        FDB     Q39
Q39:    FCB     39,0,1     ****** LAB TEST QUESTION ******
*
        FCC     /Do you currently take anti-coagulents or$/
        FCC     /blood thinning medicine?/
        FCB     0,NBRNCH
        FDB     Q40
Q40:    FCB     40,0,1     ****** LAB TEST QUESTION ******
*
        FCC     /Have you ever had prolonged or unusual$/
        FCC     /bleeding from nosebleeds, tooth$/
        FCC     /extractions, cuts or surgery?/
        FCB     0,NBRNCH
        FDB     Q41
```

```
Q41:    FCB     41,0,1      ****** LAB TEST QUESTION ******
*
        FCC     /Do you bleed from your gums when you$/
        FCC     /brush your teeth?/
        FCB     0,NBRNCH
        FDB     Q42
Q42:    FCB     42,0,1      ****** LAB TEST QUESTION ******
*
        FCC     /Have you ever been diagnosed as having a$/
        FCC     /serious bleeding problem?/
        FCB     0,NBRNCH
        FDB     Q43
Q43:    FCB     43,0,1      ****** LAB TEST QUESTION ******
*
        FCC     /Has a family member or blood relative$/
        FCC     /ever been diagnosed as having a serious$/
        FCC     /bleeding disorder?/
        FCB     0,NBRNCH
        FDB     Q44
Q44:    FCB     44,0,1      ****** LAB TEST QUESTION ******
*
        FCC     /Have you ever had kidney stones, kidney$/
        FCC     /failure, dialysis, or infection of the$/
        FCC     /kidney?/
        FCB     0,NBRNCH
        FDB     Q45
Q45:    FCB     45,0,1      ****** LAB TEST QUESTION ******
*
        FCC     /Have you ever had hepatitis, yellow$/
        FCC     /jaundice, liver disease or malaria?/
        FCB     0,BRANCH
        FDB     Q48,Q46
Q46:    FCB     46,0,1      ****** LAB TEST QUESTION ******
*
        FCC     /Have you ever been exposed to anyone$/
        FCC     /with yellow jaundice or hepatitis?/
        FCB     0,BRANCH
        FDB     Q47,Q48
Q47:    FCB     47,0,1      ****** LAB TEST QUESTION ******
*
        FCC     /Have you ever been exposed to anyone$/
        FCC     /with yellow jaundice or hepatitis within$/
        FCC     /the last 6 months?/
        FCB     0,NBRNCH
        FDB     Q48
Q48:    FCB     48,0,1      ****** LAB TEST QUESTION ******
*
        FCC     /Do you often drink more than three$/
        FCC     /alcoholic drinks per day? (Three shots,$/
        FCC     /three beers, or three glasses of wine?)/
        FCB     0,NBRNCH
        FDB     Q49
Q49:    FCB     49,0,1      ****** LAB TEST QUESTION ******
*
        FCC     /Within the last 2 years have you taken,$/
        FCC     /injected or smoked any non-prescription$/
        FCC     /drugs such as cocaine, marijuana, LSD,$/
        FCC     /herion, etc./
        FCB     0,NBRNCH
        FDB     Q50
Q50:    FCB     50,0,1      ****** LAB TEST QUESTION ******
*
        FCC     /Have you been exposed to the body$/
        FCC     /secretions (blood, urine, saliva, etc.)$/
        FCC     /of anyone likely to have the AIDS virus?/
        FCB     0,NBRNCH
        FDB     Q51
Q51:    FCB     51,0,1      ****** LAB TEST QUESTION ******
*
        FCC     /Are you in a high risk group for AIDS?$/
```

```
            FCC     /(Homosexual, Bisexual, had sex with a$/
            FCC     /prostitute in the last 6 years or have$/
            FCC     /Hemophilia.)/
            FCB     0,NBRNCH
            FDB     Q52
Q52:        FCB     52,0,1      ****** LAB TEST QUESTION ******
*
            FCC     /Would you like to receive a test to find$/
            FCC     /out if you have been exposed to the$/
            FCC     /AIDS virus?/
            FCB     0,NBRNCH
            FDB     Q53
Q53:        FCB     53,0,1      ****** LAB TEST QUESTION ******
*
            FCC     /Do you have any pain or discomfort with$/
            FCC     /urination, or have you noticed any$/
            FCC     /blood in your urine?/
            FCB     0,NBRNCH
            FDB     Q54
Q54:        FCB     54,0,1      ****** LAB TEST QUESTION ******
*
            FCC     /Are you female?/
            FCB     0,BRANCH
            FDB     Q55,Q56
Q55:        FCB     55,2,1      ****** LAB TEST QUESTION ******
*
            FCC     /Do you have any reason to believe you$/
            FCC     /are pregnant or that you may possably$/
            FCC     /be pregnant?/
            FCB     0,NBRNCH
            FDB     Q71
*
W55:        FCC     /Date of your last normal menstrual period?$/
            FCB     0
W55Y:       FCC     /Patient believes that she may be pregnant.$/
            FCB     0
*
Q56:        FCB     56,0,1      ****** LAB TEST QUESTION ******
*
            FCC     /Do you have muscle cramps or spasms in$/
            FCC     /your legs more than three times$/
            FCC     /per year?/
            FCB     0,NBRNCH
            FDB     Q57
Q57:        FCB     57,1,1      ****** LAB TEST QUESTION ******
*
            FCC     /Are you going to have an operation?/
            FCB     0,NBRNCH
            FDB     Q58
*
W57:        FCC     /What operation are you going to have?$/
            FCB     0
Q58:        FCB     58,0,2      ***** ANESTHESIA QUESTION *****
*
            FCC     /Do you wear dentures, partial or a$/
            FCC     /bridge?/
            FCB     0,NBRNCH
            FDB     Q59
*
W58Y:       FCC     /Patient wears dentures.$/
            FCB     0
*
Q59:        FCB     59,0,2      ***** ANESTHESIA QUESTION *****
*
            FCC     /Do you have any capped teeth?/
            FCB     0,NBRNCH
            FDB     Q60
*
W59Y:       FCC     /Patient has capped teeth.$/
            FCB     0
```

```
*
Q60:    FCB     60,0,2      ***** ANESTHESIA QUESTION *****
*
        FCC     /Do you wear contact lenses?/
        FCB     0,NBRNCH
        FDB     Q61
*
W60Y:   FCC     /Patient wears contact lenses.$/
        FCB     0
*
Q61:    FCB     61,0,2      ***** ANESTHESIA QUESTION *****
*
        FCC     /Do you have any teeth loose?/
        FCB     0,NBRNCH
        FDB     Q62
*
W61Y:   FCC     /Patient has loose teeth.$/
        FCB     0
*
Q62:    FCB     62,1,2      ***** ANESTHESIA QUESTION *****
*
        FCC     /Do you have any allergies?/
        FCB     0,NBRNCH
        FDB     Q63
*
W62:    FCC     /What are you allergic to?$/
        FCB     0
W62Y:   FCC     /Paitent has allergies.$/
        FCB     0
*
Q63:    FCB     63,1,2      ***** ANESTHESIA QUESTION *****
*
        FCC     /Have you had anesthesia in the past?/
        FCB     0,NBRNCH
        FDB     Q64
*
W63:    FCC     /When did you previously have anesthesia?$/
        FCB     0
W63Y:   FCC     /Patient has previously had anesthesia.$/
        FCB     0
*
Q64:    FCB     64,1,2      ***** ANESTHESIA QUESTION *****
*
        FCC     /Have you or any other member of your$/
        FCC     /family or blood relatives had any$/
        FCC     /problems with anesthesia in the past?/
        FCB     0,NBRNCH
        FDB     Q65
*
W64:    FCC     /What problems have you or any member of your family had$/
        FCC     /with anesthesia?$/
        FCB     0
W64Y:   FCC     /Patient or a family member had problems with anesthesia.$/
        FCB     0
*
Q65:    FCB     65,0,1      ****** LAB TEST QUESTION ******
*
        FCC     /Are you older than 59?/
        FCB     0,BRANCH
        FDB     Q67,Q66
Q66:    FCB     66,0,1      ****** LAB TEST QUESTION ******
*
        FCC     /Are you older than 39?/
        FCB     0,NBRNCH
        FDB     Q67
Q67:    FCB     67,0,1      ****** LAB TEST QUESTION ******
*
        FCC     /Have you had blood tests in the last$/
        FCC     /6 months?$/
        FCB     0,NBRNCH
        FDB     Q68
```

```
*
W67:    FCC     /Where did you have a blood test in the /
        FCC     /last 6 months?$/
        FCB     0
W67Y:   FCC     /Patient has had a blood test in the last 6 months.$/
        FCB     0
W67N:   FCC     /Patient may not have had a blood test in the last 6 months.
        FCB     0
*
Q68:    FCB     68,0,1    ****** LAB TEST QUESTION ******
*
        FCC     /Have you had a chest X-ray in the last$/
        FCC     /2 months?/
        FCB     0,NBRNCH
        FDB     Q69
*
W68:    FCC     /Where did you have a chest X-RAY in the /
        FCC     /last 2 months?$/
        FCB     0
W68Y:   FCC     /Patient has had a chest X-RAY in the last 2 months.$/
        FCB     0
W68N:   FCC     /Patient may not have had a chest X-RAY in the last 2 months
        FCB     0
*
Q69:    FCB     69,0,1    ****** LAB TEST QUESTION ******
*
        FCC     /Have you had an EKG in the last$/
        FCC     /2 months?/
        FCB     0,NBRNCH
        FDB     Q70
*
W69:    FCC     /Where did you have an EKG in the last 2 months?$/
        FCB     0
W69Y:   FCC     /Patient has had an EKG in the last 2 months.$/
        FCB     0
W69N:   FCC     /Patient may not have had an EKG in the last 2 months.$/
        FCB     0
*
Q70:    FCB     70,0,1    ****** LAB TEST QUESTION ******
*
        FCC     /Has your stool been checked for blood in$/
        FCC     /the last year?/
        FCB     0,NBRNCH
        FDB     Q73
*
W70Y:   FCC     /Patients stool has been checked for /
        FCC     /blood in the last year.$/
        FCB     0
W70N:   FCC     /Patients stool may not have been checked /
        FCC     /for blood in the last year.$/
        FCB     0
*
Q71:    FCB     71,2,1    ****** LAB TEST QUESTION ******
*
        FCC     /Have you had a pap smear in the last$/
        FCC     /year?/
        FCB     0,NBRNCH
        FDB     Q72
*
W71Y:   FCC     /Patient has had a pap smear in the last year.$/
        FCB     0
W71N    FCC     /Patient may not have had a pap smear in the last year.$/
        FCB     0
*
Q72:    FCB     72,2,1    ****** LAB TEST QUESTION ******
        FCC     /Have you had a mammogram (X-Rays of your$/
        FCC     /breasts) in the last year?/
        FCB     0,NBRNCH
        FDB     Q56
```

```
*
W72Y:   FCC     /Patient has had a mammogram in the last year.$/
        FCB     0
W72N    FCC     /Patient may not have had a mammogram in the last year.$/
        FCB     0
*
Q73:    FCB     73,0,3    *** GENERAL HEALTH QUESTION ***
*
        FCC     /Have you been diagnosed as having a$/
        FCC     /hiatus hernia?/
        FCB     0,NBRNCH
        FDB     Q74
*
W73Y:   FCC     /Patient has been diagnosed as having a hiatus hernia.$/
        FCB     0
*
Q74:    FCB     74,0,3    *** GENERAL HEALTH QUESTION ***
*
        FCC     /Have you had heartburn within the last$/
        FCC     /month?/
        FCB     0,NBRNCH
        FDB     Q75
*
W74Y:   FCC     /Patient has heartburn.$/
        FCB     0
*
Q75:    FCB     75,0,3    *** GENERAL HEALTH QUESTION ***
*
        FCC     /Do you take Cimetidine, Ranitidine$/
        FCC     /Tagamet, or Zantac?/
        FCB     0,NBRNCH
        FDB     Q76
*
W75Y:   FCC     /Patient takes Cimetidine or a similar drug.$/
        FCB     0
*
Q76:    FCB     76,0,3    *** GENERAL HEALTH QUESTION ***
*
        FCC     /Do you take or have you taken medicine$/
        FCC     /for thyroid disease?/
        FCB     0,NBRNCH
        FDB     Q77
*
W76Y:   FCC     /Patient takes medicine for thyroid disease.$/
        FCB     0
*
Q77:    FCB     77,0,3    *** GENERAL HEALTH QUESTION ***
*
        FCC     /Have you ever had a seizure, convulsion,$/
        FCC     /fit, stroke or been paralyzed?/
        FCB     0,NBRNCH
        FDB     QEND
*
W77Y:   FCC     /Patient has had a seizure, stroke or been paralyzed.$/
        FCB     0
*
QEND:   FCB     0
*
*
QCOUNT: FCB     77
*
* The following array of pointers contains the address of the first
* character in each of the question strings.
```

```
*
QARRAY: FDB         Q01,Q02,Q03,Q04,Q05,Q06,Q07,Q08,Q09
        FDB         Q10,Q11,Q12,Q13,Q14,Q15,Q16,Q17,Q18,Q19
        FDB         Q20,Q21,Q22,Q23,Q24,Q25,Q26,Q27,Q28,Q29
        FDB         Q30,Q31,Q32,Q33,Q34,Q35,Q36,Q37,Q38,Q39
        FDB         Q40,Q41,Q42,Q43,Q44,Q45,Q46,Q47,Q48,Q49
        FDB         Q50,Q51,Q52,Q53,Q54,Q55,Q56,Q57,Q58,Q59
        FDB         Q60,Q61,Q62,Q63,Q64,Q65,Q66,Q67,Q68,Q69
        FDB         Q70,Q71,Q72,Q73,Q74,Q75,Q76,Q77
        FDB         QEND
*
* This section of the data contains the various tests. An array of question
* pointers corresponding to the question number is stored here. A positive
* or don't know will result in the associated test being performed.
* The data format is:
*
*       byte 1      <tval> test index
*       byte 2      <icnt> Number of pointers in the following array
*       byte 3      <idx1>
*       byte N      <idxN> N = 3 + idx1
*       byte N+1    Test name string
*
TEST01:     FCB     1,13
            FDB     Q01,Q02,Q03,Q04,Q05,Q06,Q07,Q08,Q10,Q11,Q12,Q54,Q65
TSTR01:     FCC     /CBC$/
            FCB     0
*
TEST02:     FCB     2,2
            FDB     Q21,Q22
TSTR02:     FCC     /DIFF$/
            FCB     0
*
TEST03:     FCB     3,5
            FDB     Q39,Q40,Q41,Q42,Q43
TSTR03:     FCC     /PLATELETS$/
            FCB     0
*
TEST04:     FCB     4,1
            FDB     Q53
TSTR04:     FCC     /URINALYSIS$/
            FCB     0
*
TEST05:     FCB     5,1
            FDB     Q55
TSTR05:     FCC     /BHCG$/
            FCB     0
*
TEST06:     FCB     6,5
            FDB     Q39,Q40,Q41,Q42,Q43
TSTR06:     FCC     /PT$/
            FCB     0
*
TEST07:     FCB     7,5
            FDB     Q39,Q40,Q41,Q42,Q43
TSTR07:     FCC     /PTT$/
            FCB     0
*
TEST08:     FCB     8,4
            FDB     Q11,Q12,Q48,Q56
TSTR08:     FCC     /CALCIUM$/
            FCB     0
*
TEST09:     FCB     9,3
            FDB     Q11,Q12,Q48
TSTR09:     FCC     /MAGNESIUM$/
            FCB     0
```

```
*
TEST10:   FCB       10,1
          FDB       Q65
TSTR10:   FCC       /CHEM 17$/
          FCB       0
*
TEST11:   FCB       11,6
          FDB       Q12,Q25,Q31,Q32,Q34,Q44
TSTR11:   FCC       /POTASSIUM$/
          FCB       0
*
TEST12:   FCB       12,3
          FDB       Q11,Q12,Q48
TSTR12:   FCC       /PHOSPHORUS$/
          FCB       0
*
TEST13:   FCB       13,6
          FDB       Q12,Q45,Q46,Q47,Q48,Q49
TSTR13:   FCC       /SGPT$/
          FCB       0
*
TEST14:   FCB       14,3
          FDB       Q11,Q12,Q48
TSTR14:   FCC       /ALBUMIN$/
          FCB       0
*
TEST15:   FCB       15,3
          FDB       Q12,Q34,Q44
TSTR15:   FCC       /BUN$/
          FCB       0
*
TEST16:   FCB       16,3
          FDB       Q12,Q34,Q44
TSTR16:   FCC       /CREAT$/
          FCB       0
*
TEST17:   FCB       17,2
          FDB       Q35,Q36
TSTR17:   FCC       /GLUCOSE$/
          FCB       0
*
TEST18:   FCB       18,7
          FDB       Q03,Q15,Q18,Q19,Q20,Q21,Q65
TSTR18:   FCC       \CHEST XRAY PA/LAT$\
          FCB       0
*
TEST19:   FCB       19,10
          FDB       Q23,Q24,Q25,Q26,Q27,Q28,Q29,Q31,Q65,Q66
TSTR19:   FCC       /EKG$/
          FCB       0
*
TEST20:   FCB       20,5
          FDB       Q09,Q49,Q50,Q51,Q52
TSTR20:   FCC       /Suggest HIV$/
          FCB       0
*
TEND:     FCB       0
*
TCOUNT:   FCB       20
*
TARRAY:        FDB       TEST01,TEST02,TEST03,TEST04,TEST05
          FDB       TEST06,TEST07,TEST08,TEST09,TEST10
          FDB       TEST11,TEST12,TEST13,TEST14,TEST15
          FDB       TEST16,TEST17,TEST18,TEST19,TEST20
          FDB       TEND
*
          END
```

```
        TITLE     'SHIFT REGISTER KEYBOARD HANDLER'
*********************************************************************
*
* KEYHAN1--THIS ROUTINE WILL ACCESS THE KEYBOARD VIA A 16 BIT SHIFT REG
* IT WILL HAVE TWO ACCESS POINTS
* 1-4 KEY SCAN
* 2-16 KEY SCAN
* IT WILL RETURN A CHARACTER POINTED TO BY KEY LIST IN ACCB
*
*
   NAME KEYHAN1
   LIST 1
   XREFB     TCSR,PORT1,P1DDR,OTCPRG,TIMREG
   XDEF KY.INT,GETK4,GETK16,KY.HAN
   DSCT
TEMP   RMB  1
DATA   RMB  1
COUNT  RMB  1
   PSCT
KEYDDR EQU  $E0
KEYDAT EQU  $10   SHIFT REGISTER INPUT DATA
KEYSHS EQU  $20   SHIFT/LOAD SET
KEYSHC EQU  $DF   SHIFT/LOAD CLEAR
KEYLHS EQU  $40   LATCH CLOCK SET
KEYLHC EQU  $BF   LATCH CLOCK CLEAR
KEYCLS EQU  $80   CLOCK SET
KEYCLC EQU  $7F   CLOCK CLEAR
DEBNDL EQU  $7FF  DEBOUNCE CONSTANT
*
KY.INT LDAA #KEYDDR
   STAA P1DDR
   RTS
KY.HAN
GETK16 PSHX
   PSHA
   LDAB #16
   BRA  GETKEY
GETK4  PSHX
   PSHA
   LDAB #4
GETKEY CLR  TEMP
   CLR  COUNT
   PSHB
GETLOP PULB
   PSHB
   BSR  KEYSCN    GET KEY IN A
   TSTA
   BEQ  GETLOP
   TST COUNT
   BNE  GETLO1
   INC  COUNT
   STAA TEMP
   BSR  DEBOUC
   BRA  GETLOP
GETLO1 PULB
   CMPA TEMP
   BNE  GETKEY
   TAB
   DECB
   LDX  #KEYLST
   ABX
   LDAB 0,X
   PULA
   PULX
   RTS

KEYSCN     LDAA PORT1
   ORAA #KEYCLS
   ANDA #KEYSHC          LATCH INPUT DATA
   ANDA #KEYLHC
```

```
       STAA PORT1           LOAD THE DATA
       LDAA PORT1
       ORAA #KEYLHS         LOAD THE DATA
       STAA PORT1
       ORAA #KEYSHS         REVERT TO THE SHIFT MODE
       STAA PORT1
*      LDAA PORT1
*      ANDA #KEYCLC         SET THE SHIFT CLOCK TO LOW
*      STAA PORT1
       CLR     DATA
       INC     DATA
SCNLOP LDAA PORT1
       ANDA #KEYDAT
       BEQ  SCNLO2
       DECB
       BEQ  SCNLO0
SCNLO1 INC DATA
       LDAA PORT1
       ANDA #KEYCLC
       STAA PORT1
       ORAA #KEYCLS
       STAA PORT1
       BRA  SCNLOP
SCNLO0 CLR  DATA
SCNLO2 LDAA DATA
       RTS
*
* DEBOUNCE DELAY
*
DEBOUC PSHX
       LDX  #DEBNDL
DEBOLP DEX
       BNE  DEBOLP
       PULX
       RTS
*
* KEY LIST
*
KEYLST FCB  12
       FCB  13
       FCB  14
       FCB  15
       FCB  52
       FCB  57
       FCB  11
       FCB  50
       FCB  53
       FCB  56
       FCB  48
       FCB  49
       FCB  52
       FCB  55
       FCB  10
       FCB  51

NAME    PRTQST
*
       LIST    1              *Use the 6801 Instruction set
*
       XDEF    PRTQST,CHKQST
*
*List the externally defined memmory locations
*
       XREF    QARRAY,QAPTR,ANS1,PRTCHR,PRTSTR,SPCHN2
*
```

```
         DSCT
*
CLASS:   RMB     1
ANSWR:   RMB     1
PFLAG:   RMB     1
CNTR:    RMB     1
*
         PSCT
*
*
* NOTE: If the declarations below are changed make sure you change ASKQ.ASM
*
YES:     FCB     12
EQYES:   EQU     12
*
NO:      FCB     13
EQNO     EQU     13
*
IDNO:    FCB     14
EQIDNO:  EQU     14
*
NOTE1:   FCC     /$Please review your answers to make sure that /
         FCC     /they are correct.$$/
         FCB     0
NOTE2:   FCC     /$$The above answers are correct as typed$$$/
         FCC     /Signed _____/
         FCC     /  Date _____$/
         FCB     0
TITLE1:  FCC     /$$      ********* LAB TEST QUESTIONS ********$$/
         FCB     0
TITLE2:  FCC     /$$      ******** ANETHESIA QUESTIONS ********$$/
         FCB     0
TITLE3:  FCC     /$$      ****** GENERAL HEALTH QUESTIONS *****$$/
         FCB     0
*
CKARY1:  FCB     1,EQYES,1,EQIDNO,1,EQNO,0    *Lab Test Questions
CKARY2:  FCB     2,EQYES,2,EQIDNO,2,EQNO,0    *Anethesia Questions
CKARY3:  FCB     3,EQYES,3,EQIDNO,3,EQNO,0    *General Health Questions
*
* This subroutine is used to print out the questions and the patients answers
* The report is sorted by class and answer. The sorting is controlled by the
* data array CHKARY above.
*
PRTQST:  PSH A                        *Save environment
         PSH B
         PSHX
*
         LDX     #NOTE1               *Print the review string
         JSR     PRTSTR
*
         JSR     SPCHN2               *Print special questions
*
         LDX     #TITLE1              *Print title for section
         JSR     PRTSTR
         LDX     #CKARY1              *Get data array
         JSR     DOLIST               *Sort and print Q&A
*
         LDX     #TITLE2              *Print title for section
         JSR     PRTSTR
         LDX     #CKARY2              *Get data array
         JSR     DOLIST               *Sort and print Q&A
*
         LDX     #TITLE3              *Print title for section
         JSR     PRTSTR
         LDX     #CKARY3              *Get data array
         JSR     DOLIST               *Sort and print Q&A
*
         LDX     #NOTE2               *Print signature line
         JSR     PRTSTR
```

```
        PULX                            *Restore environment
        PUL B
        PUL A
        RTS
*
*
DOLIST: LDA A   0,X             *Get the class
        BEQ     FIN             *Data exhausted?
        INX
        LDA B   0,X             *Get answer
        INX
        JSR     CHKQST                  *Check and print the Q&A
        BRA     DOLIST                  *Process next pair
*
FIN:    RTS
*
* This routine scans the question array searching for a particular class
* of question (ACC-A). If the class matches and the answer (ACC-B) is a
* match the question and answer are printed.
*
* THIS ROUTINE USES THE A AND B ACCUMULATORS:
*
*   ACC-A = CLASS
*   ACC-B = ANSWER
*
CHKQST: STA A   CLASS
        STA B   ANSWR
        PSHX
        LDX     #QARRAY
*
NXTONE: STX     QAPTR                   *Save the question arry pointer
        LDX     0,X                     *Get question pointer
        LDA B   0,X                     *Get the question offset
        BEQ     DONE                    *Finished?
        INX                             *Position to class
        INX
        LDA A   0,X                     *Load the question class
        CMP A   CLASS                   *Is it the right class
        BNE     NOTONE
        INX                             *Save string address on stack
        PSHX
        LDX     #ANS1                   *Get answer array
        ABX                             *Add in the offset
        LDA A   0,X                     *Read the patient answer
        CMP A   ANSWR                   *Does it match?
        BNE     NOTANS
        PULX                            *Yes, get address of string
        JSR     SPPRT                   *Print the question
        BRA     NOTONE
*
NOTANS: PULX                            *Clean up stack
*
NOTONE: LDX     #QAPTR                  *Get question pointer
        LDX     0,X
        LDA B   #2                      *Set to next question
        ABX
        BRA     NXTONE                  *Process next question
*
DONE:   PULX                            *Restore index register
        RTS
*
*
*
YESSTR: FCC     /YES/
        FCB     0
NOSTR:  FCC     /NO/
        FCB     0
IDNSTR: FCC     /NOT SURE/
        FCB     0
```

```
ERROR:   FCC     /** ERROR **/
         FCB     0
*
* This is a special print routine used to print out the questions and
* associated answers. The first line is extended to include the patients
* answer. The address of the question string is expected in the INDEX
* register while the patients answer is in ACC-A
*
SPPRT:   PSH B
         CLR B
         STA B   PFLAG            *Clear the print flag
         STA B   CNTR                    *Clear the char counter
*
NXTCHR:  LDA B   0,X              *Get next character to print
         INX
         TST     PFLAG                   *If print flag set branch
         BNE     PRTCH
         INC     CNTR                    *Increment char counter
         CMP B   #'$'                    *Is char reserved character
         BEQ     PRTANS                  *Yes, print answer
         TST B                           *Is char EOS
         BNE     PRTCH                   *Yes, print answer
*
PRTANS:  INC     PFLAG                   *Set the print flag
         PSH B                           *Save Accumulators
         PSH A
         LDA A   #60                     *Calculate blank pads
         SUB A   CNTR
         LDA B   #' '
BLANK:   JSR     PRTCHR                  *Pad out to column 60
         DEC A
         BNE     BLANK
*
         PUL A                           *Get paitents answer
         PSHX
         CMP A   YES                     *YES, Print string
         BNE     OV1
         LDX     #YESSTR
         BRA     OV4
*
OV1:     CMP A   NO                      *NO, Print string
         BNE     OV2
         LDX     #NOSTR
         BRA     OV4
*
OV2:     CMP A   IDNO                    *NOT SURE, Print string
         BNE     OV3
         LDX     #IDNSTR
         BRA     OV4
*
OV3:     LDX     #ERROR                  *ERROR, Print string
OV4:     JSR     PRTSTR
         PULX
         PULB
*
PRTCH:   TST B                           *EOS?
         BEQ     STDONE                  *Yes, branch to exit
         CMP B   #'$'                    *Special character?
         BNE     OV5                     *No, branch and print
         LDA B   #13                     *CR
         JSR     PRTCHR
         LDA B   #10                     *LF
OV5:     JSR     PRTCHR                  *Print the character
         BRA     NXTCHR
*
```

```
STDONE: LDA B    #13                   *CR
        JSR      PRTCHR
        LDA B    #10                   *LF
        JSR      PRTCHR
        LDA B    #10                   *LF
        JSR      PRTCHR                *Print the character
*
        PUL B
        RTS
*
        END NAME     REPPRT
        LIST     1
*
        XDEF     RPTPRT,PRTSTR
        XREF     HEADER,DISCLM,SPCHN1,SPCHN2,SPCHN3
        XREF     TARRAY,TCOUNT,NO,NOANS,ANS1
*
        DSCT
*
NXTTST: RMB      2
OFFSET: RMB      2
NUMIDX: RMB      1
PFLAG:  RMB      1
CURTST: RMB      1
TSTPRT: RMB      20+1        *Must change if new tests are added
*
        PSCT
*
TITLE1: FCC      /$             INDICATED LABORATORY TESTS$$/
        FCB      0
TITLE2: FCC      \$$THE PATIENT REPORTS THAT HE/SHE HAS HAD THE \
        FCC      /FOLLOWING $TESTS RECENTLY:$$/
        FCB      0
TITLE3: FCC      /$$SOME ITEMS PERTINENT TO ANESTHESIA CARE ARE:$$/
        FCB      0
*
STMT1:  FCC      /$$PLEASE REVIEW THE PATIENT'S RESPONSES TO THE HEALTHQUIZ$/
        FCC      /FOR MORE DETAILED INFORMATION:$$/
        FCB      0
STMT2:  FCC      /$$If operation is associated with significant blood loss,$/
        FCC      /obtain Hgb or HCT.$/
        FCB      0
STMT3:  FCC      /$$If operation involves insertion of a prosthesis or foreig
        FCC      / material,$obtain a URINALYSIS to rule out a urinary tract/
        FCC      / infection.$$/
        FCB      0
*
* This routine is responsible for printing the primary report generated by
* this device. A header is printed along with the special additional
* questions. This routine also determines if one of the tests is called
* for, if it is, it is printed. This routine also calls another routine
* which prints out the anethesia results and patient history info.
*
RPTPRT: PSH A                  *Save the environment
        PSH B
        PSHX
*
        LDX      #TSTPRT      *Clear the test printed array
        LDA A    TCOUNT
        INC A
        CLR B
CLRTAY: STA B    0,X
```

```
        INX
        DEC A
        BNE     CLRTAY

JSR     HEADER      *Print the header
        JSR     SPCHN2      *Process special case questions
        LDA B   #1
        JSR     DISCLM      *Print the disclaimer
*
        LDX     #TITLE1     *Print the title
        JSR     PRTSTR
*
        LDX     #TARRAY     *Get address of test array
        STX     NXTTST
*
NXTQ:   LDX     0,X         *Get address of question data
        CLR A
        STA A   PFLAG       *Clear the print flag
        LDA A   0,X         *Get the test number
        BEQ     DONE
        STA A   CURTST      *Save test index
        INX                 *Advance to index count
        LDA A   0,X         *Get the number of indexes
        BEQ     NOQST       *No indexes? branch.
        STA A   NUMIDX      *Save the index count
        INX                 *Position to first entry
*
NXTANS: STX     OFFSET      *Save the index address
        LDX     0,X
        LDA B   0,X         *Get the index value
        LDX     #ANS1       *Get base address of answer array
        ABX                 *Add the index to the base
        LDA A   0,X         *Get question answer
        CMP A   NOANS       *NO ANSWER do not print
        BEQ     OV1
        CMP A   NO          *If no, do not print test
        BEQ     OV1
        INC     PFLAG       *Yes or Don't know? Set print flag
OV1:    LDA A   NUMIDX      *Get index counter
        DEC A               *Decrement counter
        BEQ     NOQST       *Testing done? Branch.
        STA A   NUMIDX      *Save counter value
        LDX     OFFSET      *Get index address
        LDA B   #2          *Move pointer to next entry
        ABX
        BRA     NXTANS      *Check next answer
*
NOQST:  LDX     OFFSET
        INX                 *Advance to test string
        INX
        TST     PFLAG       *If print flag set print test
        BEQ     OV2
        JSR     PRTSTR
        LDX     #TSTPRT     *Get test print array
        LDA B   CURTST      *Get test index
        ABX                 *Add offset
        STA B   0,X         *Set print true
*
OV2:    LDX     NXTTST      *Get the address of the array
        INX                 *Advance to next element
        INX
        STX     NXTTST      *Save address of new element
        BRA     NXTQ        *Check the new entry
*
DONE:   LDX     #TSTPRT     *Print message related to test 1?
        LDA A   1,X
        BNE     TST4
        LDX     #STMT2
        JSR     PRTSTR
```

```
TST4:    LDX     #TSTPRT     *Print message related to test 4?
         LDA A   4,X
         BNE     PRTD2
         LDX     #STMT3
         JSR     PRTSTR
*
PRTD2:   LDA B   #2
         JSR     DISCLM
         LDX     #TITLE2
         JSR     PRTSTR
         JSR     SPCHN1      *Print information about previous tests
         LDX     #TITLE3
         JSR     PRTSTR
         JSR     SPCHN3      *Print anesthesia information
         LDX     #STMT1
         JSR     PRTSTR
         LDA B   #3
         JSR     DISCLM
*
         PULX                *Restore the environment
         PUL B
         PUL A
         RTS
*
         XREF    PRTCHR
*
PRTSTR:  PSH B
LOOP:    LDA B   0,X
         BEQ     OUT
         CMP B   #'$'
         BNE     PCHR
         LDA B   #13
         JSR     PRTCHR
         LDA B   #10
         JSR     PRTCHR
         INX
         BRA     LOOP
*
PCHR     JSR     PRTCHR
         INX
         BRA     LOOP
*
OUT      PUL B
         RTS
         END
         NAME STUBS
*
         LIST    1
*
         XDEF    SYDIAG,SETCLK
         XREF    CLR.SC,STRDSP,DBKEY
*
         PSCT
*
MES:     FCC     /$  -- FUNCTION NOT YET IMPLEMENTED --$/
         FCC     /$        ENTER ANY KEY TO CONTINUE/
         FCB     0
*
SYDIAG:  NOP
SETCLK:  PSHX
         JSR     CLR.SC
         LDX     #MES
         JSR     STRDSP
         JSR     DBKEY
*
         PULX
         RTS
*
         END
```

The invention claimed is:

1. A portable patient-operable pre-operative test selector especially for use by bed-ridden pre-operative patients, said selector comprising:
power supply means for accepting a battery, electronic circuitry connected to derive operating power exclusively from a battery when installed in said power supply means, said electronic circuitry including data-storage means for storing a series of pre-operative questions directed to the determination of which pre-operative diagnostic tests should be undergone by a patient before surgery, reflective display means, programmable data-processing means, control program storage means for storing a program for controlling said data-processing means, a special-purpose control program stored therein, said control program being arranged for displaying said pre-operative questions serially on said display means, means operable by an unskilled patient to answer "yes" and "no" to each such question in turn, means for storing such answers, said control program being further arranged for analyzing said answers and determining therefrom which pre-operative diagnostic tests are indicated, and output means for revealing the results of such determination.

2. A portable test selector for use by an untrained patient to complete a medical questionnaire, comprising:
read-only memory means for storing (i) a series of preselected medical questions related to determining which tests among a set of preselected tests the patient should undergo, and (ii) a decision table indicating for each of the tests which answers to which questions should cause that test to be determined as one the patient should undergo;
scratchpad memory means for storing data; means for reading said data from said scratchpad memory means
display means for displaying information to the patient;
interrogation means for causing the medical questions stored in said read-only memory means to be displayed to the patient by the display means;
manual input means for enabling the patient to indicate an answer to a displayed question; and
tabulating means for enabling the patient to indicate an answer to a displayed question; and
tabulating means for causing the corresponding answer indicated by the patient via the manual input means to be stored as data in the scratchpad memory means;
wherein the read-only memory means is easily removable from the test selector and replaceable to enable updating of the medical questions and decision table.

3. A portable test selector for use by an untrained patient to complete a medical questionnaire, comprising:
read-only memory means for storing (i) a series of preselected medical questions related to determining which test among a set of preselected test the patient should undergo, and (ii) a decision table indicating for each of the tests which answers to which questions should cause that test to be determined as one the patient should undergo;
scratchpad memory means for storing data; means for reading said data from said scratchpad memory means
display means for displaying information to the patient;
interrogation means for causing the medical questions stored in said read-only memory means to be displayed to the patient by the display means;
manual input means for enabling the patient to indicate an answer to a displayed question; and
tabulating means for causing the corresponding answer indicated by the patient via the manual input means to be stored as data in the scratchpad memory means;
wherein the medical questions are those requiring an answer of YES or NO or NOT SURE, and the manual input means enables the patient to indicate YES, NO, or NOT SURE as the answer.

4. A portable test selector for use by an untrained patient to complete a medical questionnaire, comprising:
read-only memory means for storing (i) a series of preselected medical questions related to determining which tests among a set of preselected tests the patient should undergo, and (ii) a decision table indicating for each of the test which answers to which questions should cause that test to be determined as one the patient should undergo;
scratchpad memory means for storing data; means for reading said data from said scratchpad memory means
display means for displaying information to the patient;
interrogation means for causing the medical questions stored in said read-only memory means to be displayed to the patient by the display means;
manual input means for enabling the patient to indicate an answer to a displayed question;
tabulating means for causing the corresponding answer indicated by the patient via the manual input means to be stored as data in the scratchpad memory means;
and reporting means responsive to the answers stored in the scratchpad memory and the decision table stored in the read-only memory means for determining for each test if the patient's answers to one or more questions should cause that test to be determined as one the patient should undergo.

5. The device of claim 4 and further including printer interface means to which a data input line to a printer can be coupled; and report generator means, responsive to the reporting means, for sending as output to the printer interface a list of only the tests which the reporting means has determined are ones the patient should undergo.

6. A portable test selector for use by an untrained patient to complete a medical questionnaire, comprising:
read-only memory means for storing (i) a series of preselected medical questions related to determining which tests among a set of preselected tests the patient should undergo, and (ii) a decision table indicating for each of the tests which answers to which questions should cause that test to be determined as one the patient should undergo;

scratchpad memory means for storing data; means for reading said data from said scratchpad memory means display means for displaying information to the patient;

interrogation means for causing the medical questions stored in said read-only memory means to be displayed to the patient by the display means;

manual input means for enabling the patient to indicate an answer to a displayed question;

tabulating means for causing the corresponding answer indicated by the patient via the manual input means to be stored as data in the scratchpad memory means;

and questionnaire printout preparation means responsive to the medical questions stored in the read-only memory means and the answers stored in the scratchpad memory means for determining, for each possible patient answer, to which questions the patient gave that answer.

7. The device of claim 6 and further including printer interface means to which the data input line to a printer can be coupled; and list generator means, responsive to the questionnaire printout preparation means, for sending as output to the printer interface a list of the questions and the patient's answers.

8. The device of claim 7 wherein the list generator means is arranged for sending the questions and the patient's answers to the printer interface with each question sorted according to the answer given to that question by the patient.

* * * * *

UNITED STATES PATENT AND TRADEMARK OFFICE
CERTIFICATE OF CORRECTION

PATENT NO.      : 5,025,374
APPLICATION NO. : 07/130934
DATED           : June 18, 1991
INVENTOR(S)     : Roizen et al.

It is certified that error appears in the above-identified patent and that said Letters Patent is hereby corrected as shown below:

Column 207, lines 47 and 48, delete beginning with "tabulating means for" to and including "a displayed question; and".

In Appendix II, columns 27 and 28, lines 59-70, delete the following questions and answers beginning with "Do you wear dentures, partial, or a bridge? No" to and including "Have you or any other member of your family or blood relatives had any problems with anesthesia in the past? No".

In Appendix II, columns 29 and 30, lines 1-32, delete beginning with "******GENERAL HEALTH" to and including "Do you take Cimetidine, Ranitidine Tagamet or Zantac? No".

In Appendix II, columns 27 and 28, line 1, insert

| | | |
|---|---|---|
| -- | Do you wear dentures, partial or a bridge | NO |
| | Do you have any capped teeth? | NO |
| | Do you wear contact lenses? | NO |
| | Do you have any teeth loose? | NO |
| | Have your or any other member of your family or blood relatives had any problems with anesthesia in the past? | NO |

****GENERAL HEALTH QUESTIONS****

| | |
|---|---|
| Have you engaged in sex (intercourse) within the last two weeks? | YES |
| Is your level of sexual desire and activity normal for you? | YES |
| Has your appetite for food changed in the last year? | NO |

UNITED STATES PATENT AND TRADEMARK OFFICE
CERTIFICATE OF CORRECTION

PATENT NO.       : 5,025,374
APPLICATION NO.  : 07/130934
DATED            : June 18, 1991
INVENTOR(S)      : Roizen et al.

It is certified that error appears in the above-identified patent and that said Letters Patent is hereby corrected as shown below:

| | |
|---|---|
| Are you eating the same foods as you were a year ago? | NO |
| Are you able to walk up stairs at the same rate you could 5 years ago? | NO |
| Have your bowel or bladder functions changed in the last year? | NO |
| Have you been diagnosed as having a hiatus hernia? | NO |
| Have you had heartburn within the last month? | NO |
| Do you take Cimetidine, Ranitidine Tagamet, or Zantac? | NO -- |

In Appendix III, Columns 57 and 58, line 52 after LDA*B #10, insert

```
--      JSR     PRTCHR
        INX
        BRA     LOOP

*
PCHR    JSR     PRTCHR
        INX
        BRA     LOOP

*
OUT     PUL B
        RTS
        END--
```

In Appendix IV, columns 133 and 134, lines 28-71, delete beginning with "* AND THE LAST LINE IS LOST" to and including "PSHB".

In Appendix IV, columns 135 and 136, lines 1-60, delete beginning with "LDAA #ROWMAX" to and including "CLR.SC  PSHX".

UNITED STATES PATENT AND TRADEMARK OFFICE
CERTIFICATE OF CORRECTION

PATENT NO. : 5,025,374
APPLICATION NO. : 07/130934
DATED : June 18, 1991
INVENTOR(S) : Roizen et al.

It is certified that error appears in the above-identified patent and that said Letters Patent is hereby corrected as shown below:

In Appendix IV, columns 137 and 138, line 42 after *ELSE THE SCREEN IS SCROLLED DOWN, insert

```
--       * AND THE LAST LINE IS LOST
         *
         REV.LF PSHA
           PSHB
           PSHX
           LDX CURSOR GET THE CURSOR POSITION
           CPX #SCBLG2 IS IT ON THE TOP LINE
           BLT REV. L1
           JSR CUR.UP
           BRA REV.FE
         REV. L1 LDD #SCBFED GET THE END OF THE BUFFER
           STD TO.PNT
           SUBD #LINLGT GET THE NEXT TO LAST LINE
           STD FR.PNT
           LDD #SCBLG1+1 GET THE AMOUNT OF CHARACTERS TO BE MOVE
           JSR MVBLRV
           LDX #SCBFST CLEAR THE TOP THE LINE
           JSR CLR.LN
           JSR DISBUF
           JSR DISCUR
         REV.FE PULX
           CLR ES.FLG
           PULB
           PULA
           RTS         --
         *
```

UNITED STATES PATENT AND TRADEMARK OFFICE
CERTIFICATE OF CORRECTION

| | |
|---|---|
| PATENT NO. | : 5,025,374 |
| APPLICATION NO. | : 07/130934 |
| DATED | : June 18, 1991 |
| INVENTOR(S) | : Roizen et al. |

It is certified that error appears in the above-identified patent and that said Letters Patent is hereby corrected as shown below:

```
--      TITLE 'INSERT LINE'
      *
      * IF LAST LINE JUST CLEAR THE LINE
      * ELSE DO A REVERSE LINE FEED AT THE CURSOR POSTION
      *
      LIN.IN PSHA
        PSHB
        PSHX
        JSR CURPOS FIND OUT WHAT ROW OUR THE CURSORS ON
        CMPA #ROWMAX
        BEQ LIN.I1
        PSHA SAVE THE ROW NUMBER
        LDD #SCBFED
        STD TO.PNT
        SUBD #LINLGT THE START OF NEXT LINE DOWN
        STD FR.PNT
        PULB
        PSHB
        LDAA #ROWMAX
        SBA
        LDAB #LINLGT
        MUL
        JSR MVBLRV
        PULA GET THE ROW NUMBER
      LIN.I1 LDAB #LINLGT GET THE LOCATION TO CLEAR OUT THE LINE
        MUL
              --
```

UNITED STATES PATENT AND TRADEMARK OFFICE
CERTIFICATE OF CORRECTION

| | | |
|---|---|---|
| PATENT NO. | : 5,025,374 | Page 5 of 6 |
| APPLICATION NO. | : 07/130934 | |
| DATED | : June 18, 1991 | |
| INVENTOR(S) | : Roizen et al. | |

It is certified that error appears in the above-identified patent and that said Letters Patent is hereby corrected as shown below:

```
--      LDX #SCBFST
        ABX
        JSR CLR. LN CLEAR THE LINE
        JSR DISBUF
        JSR DISCUR
        CLR ES.FLG
        PULX
        PULB
        PULA
        RTS
      *
        TITLE 'LINE DELETE'
      *
      * THIS ROUTINE DELETES THE LINE THE CURSORS ON
      *
        LIN.DE PSHA
          PSHB
          JSR CURPOS FIND OUT WHERES THE CURSOR
          LDAB #LINLGT
          MUL
          LDX #SCBFST
          ABX
          JSR CLR.LN
          JSR DISBUF
          JSR DISCUR
          CLR ES.FLG
          PULB
          PULA
          RTS
        *
               --
```

UNITED STATES PATENT AND TRADEMARK OFFICE
CERTIFICATE OF CORRECTION

PATENT NO. : 5,025,374  
APPLICATION NO. : 07/130934  
DATED : June 18, 1991  
INVENTOR(S) : Roizen et al.

Page 6 of 6

It is certified that error appears in the above-identified patent and that said Letters Patent is hereby corrected as shown below:

```
--      TITLE 'SEND CURSOR INFORMATION'
      *
      * CURPOS IS CALLED AND THE CURPOSITION BOTH ROW AND COL
      * ARE ADDED THE BASE AND SENT OUT TO THE SERIAL PORT
      * FOLLOW BY A CARRIAGE RETURN
      *
      SEN. CU JSR CURPOS
        ADDA #BASE
      * JSR SD.DRV
        TBA
        ADDA #BASE
      * JSR SD.DRV
        LDAA #CR
      * JSR SD.DRV
        CLR ES.FLG
        RTS
      *
        TITLE 'CLEAR SCREEN'
      *
      * CLEAR THE SCREEN AND INITIALIZE THE CURSOR
      *
      CLR.SC PSHX
                   --
```

Signed and Sealed this

Nineteenth Day of September, 2006

JON W. DUDAS  
*Director of the United States Patent and Trademark Office*